(12) United States Patent
Evnin et al.

(10) Patent No.: US 10,738,118 B2
(45) Date of Patent: *Aug. 11, 2020

(54) METHODS OF USING BISPECIFIC CD33 AND CD3 BINDING PROTEINS

(71) Applicant: Amphivena Therapeutics, Inc., South San Francisco, CA (US)

(72) Inventors: Luke Evnin, San Francisco, CA (US); Jeanmarie Guenot, San Francisco, CA (US); Lori Kunkel, San Francisco, CA (US)

(73) Assignee: Amphivena Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/578,185

(22) PCT Filed: May 26, 2016

(86) PCT No.: PCT/US2016/034479
§ 371 (c)(1),
(2) Date: Nov. 29, 2017

(87) PCT Pub. No.: WO2016/196230
PCT Pub. Date: Dec. 8, 2016

(65) Prior Publication Data
US 2018/0148507 A1    May 31, 2018

Related U.S. Application Data

(60) Provisional application No. 62/266,438, filed on Dec. 11, 2015, provisional application No. 62/168,641, filed on May 29, 2015.

(51) Int. Cl.
| A61K 39/395 | (2006.01) |
| C07K 16/28 | (2006.01) |
| A61P 35/02 | (2006.01) |
| A61K 51/10 | (2006.01) |
| A61K 39/00 | (2006.01) |

(52) U.S. Cl.
CPC .......... *C07K 16/2809* (2013.01); *A61K 51/10* (2013.01); *A61P 35/02* (2018.01); *C07K 16/2803* (2013.01); *A61K 2039/505* (2013.01); *C07K 2317/31* (2013.01); *C07K 2317/33* (2013.01); *C07K 2317/34* (2013.01); *C07K 2317/622* (2013.01); *C07K 2317/626* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| 7,129,330 B1 | 10/2006 | Little et al. |
| 7,258,986 B2 | 8/2007 | Maur et al. |
| 7,612,181 B2 | 11/2009 | Wu et al. |
| 7,820,166 B2 | 10/2010 | Lanzavecchia |
| 8,076,459 B2 | 12/2011 | Hofmeister et al. |
| 8,101,722 B2 | 1/2012 | Kufer et al. |
| 8,236,308 B2 | 8/2012 | Kischel et al. |
| 8,258,268 B2 | 9/2012 | Wu et al. |
| 8,409,577 B2 | 4/2013 | Thompson et al. |
| 8,518,403 B2 | 8/2013 | Hoffmann et al. |
| 8,652,466 B2 | 2/2014 | Stavenhagen et al. |
| 8,759,494 B2 | 6/2014 | Bachmann et al. |
| 8,846,042 B2 | 9/2014 | Zhou |
| 9,212,225 B1 | 12/2015 | Ellwanger et al. |
| 9,803,029 B2 | 10/2017 | Ellwanger et al. |
| 2010/0150918 A1 | 6/2010 | Kufer et al. |
| 2010/0174053 A1 | 7/2010 | Johnson et al. |
| 2011/0110852 A1 | 5/2011 | Miller et al. |
| 2011/0206672 A1 | 8/2011 | Little et al. |
| 2011/0262439 A1 | 10/2011 | Kufer et al. |
| 2011/0287009 A1 | 11/2011 | Scheer et al. |
| 2011/0293619 A1 | 12/2011 | Kufer et al. |
| 2012/0195900 A1 | 8/2012 | Ghayur et al. |
| 2012/0251554 A1 | 10/2012 | Bachmann et al. |
| 2013/0017200 A1 | 1/2013 | Scheer et al. |
| 2013/0129730 A1 | 5/2013 | Kufer et al. |
| 2013/0189263 A1 | 7/2013 | Little et al. |
| 2013/0224205 A1 | 8/2013 | Hofmeister et al. |
| 2013/0295121 A1 | 11/2013 | Johnson et al. |
| 2014/0056897 A1 | 2/2014 | Buelow et al. |
| 2014/0099318 A1 | 4/2014 | Huang et al. |
| 2014/0127210 A1 | 5/2014 | Kim et al. |

(Continued)

FOREIGN PATENT DOCUMENTS

| EP | 2480574 | 8/2012 |
| EP | 2155783 B1 | 7/2013 |

(Continued)

OTHER PUBLICATIONS

Acute Myeloid Leukemia definition. American Cancer Society (pp. 1-5) (Nov. 1, 2016).

(Continued)

*Primary Examiner* — Meera Natarajan

(74) *Attorney, Agent, or Firm* — Fish & Richardson P.C.

(57) ABSTRACT

Described herein are binding proteins that specifically bind to human CD33, and in particular to bispecific binding proteins that specifically bind to human CD33 and human CD3. Also described herein are bispecific tandem diabodies that bind to CD33 and CD33, and their uses for immunotherapy of CD33+ cancers, diseases and conditions such as acute myeloid leukemia (AML).

21 Claims, 28 Drawing Sheets

Specification includes a Sequence Listing.

(56) References Cited

U.S. PATENT DOCUMENTS

| | | |
|---|---|---|
| 2014/0134162 A1 | 5/2014 | Stavenhagen et al. |
| 2014/0213771 A1 | 7/2014 | Ghayur et al. |
| 2014/0221622 A1 | 8/2014 | Ghayur et al. |
| 2014/0242077 A1 | 8/2014 | Choi et al. |
| 2014/0242079 A1 | 8/2014 | Bacac et al. |
| 2014/0271582 A1 | 9/2014 | Forman et al. |
| 2014/0377270 A1 | 12/2014 | Moore et al. |
| 2015/0056159 A1 | 2/2015 | Kontermann et al. |
| 2016/0002333 A1 | 1/2016 | Ellwanger |
| 2018/0148507 A1 | 5/2018 | Evnin |

FOREIGN PATENT DOCUMENTS

| | | |
|---|---|---|
| JP | 2006506119 | 2/2006 |
| JP | 2010509234 | 3/2010 |
| JP | 2010524851 | 7/2010 |
| JP | 2012518646 | 8/2010 |
| TW | 201605473 | 2/2016 |
| WO | WO-03025018 A2 | 3/2003 |
| WO | WO-2007048186 A1 | 5/2007 |
| WO | WO-2008119565 A2 | 10/2008 |
| WO | WO-2012045752 A1 | 4/2012 |
| WO | WO 2012162067 | 11/2012 |
| WO | WO 2013013700 | 1/2013 |
| WO | WO-2013013700 A1 | 1/2013 |
| WO | WO-2013026837 A1 | 2/2013 |
| WO | WO-2013113615 A1 | 8/2013 |
| WO | WO-2013190555 A1 | 12/2013 |
| WO | WO-2014012085 A2 | 1/2014 |
| WO | WO 2014151910 | 9/2014 |
| WO | WO-2015036583 A2 | 3/2015 |
| WO | WO 2016004108 | 1/2016 |
| WO | WO-2016196230 A1 | 12/2016 |

OTHER PUBLICATIONS

Aigner et al. T lymphocytes can be effectively recruited for ex vivo and in vivo lysis of AML blasts by a novel CD33/CD3-bispecific BiTE antibody construct. Leukemia 27(5):1107-1115 (Apr. 2013; Epub Nov. 26, 2012).
Cochlovis et al. Cure of Burkitt's lymphoma in severe combined immunodeficiency mice by T cells, tetravalent CD3×CD19 tandem diabody, and CD28 costimulation. Cancer Research 60:4336-4341 (2000).
Co-pending U.S. Appl. No. 15/796,556, filed Oct. 27, 2017.
Friedrich et al. Preclinical Characterization of AMG 330, a CD3/CD33-Bispecific T-Cell-Engaging Antibody with Potential for Treatment of Acute Myelogenous Leukemia. Molecular Cancer Therapeutics 13(6):1549-1557 (2014).
Grimwade et al. Refinement of cytogenetic classification in acute myeloid leukemia: determination of prognostic significance of rare recurring chromosomal abnormalities among 5876 younger adult patients treated in the United Kingdom Medical Research Council trials. Blood. 116(3):354-365 (2010).
Hu et al. Immunoglobulin Mu Heavy Chain. Partial. GenBank AFR53885.1 (Sep. 16, 2012).
Hussaini et al. Targeting CD123 in Leukemic Stem Cells Using Dual Affinity Re-Targeting Molecules (DARTs®). Blood: 122 (21):Abstract (2013).
Kao et al. Genetics of somatic mammalian cells, VII. Induction and isolation of nutritional mutants in Chinese hamster cells. PNAS USA 60(4):1275-1281 (1968).
Kipriyanov. Generation and characterization of bispecific tandem diabodies for tumor therapy. Methods Mol Biol 207:323-333 (2003).
Kipriyanov. Generation of bispecific and tandem diabodies. Methods Mol Biol. 562:177-193 (2009).
Laszlo et al. The past and future of CD33 as therapeutic target in acute myeloid leukemia. Blood Rev. 28(4):143-153 (2014).
Le Gall et al. Di-, tri- and tetrameric single chain Fv antibody fragments against human CD19: effect of valency on cell binding. FEBS Letts 453:164-168 (1999).
Le Gall et al. Effect of linker sequences between the antibody variable domains on the formation, stability and biological activity of a bispecific tandem diabody. Protein Eng Des Sel. 17(4):357-366. (2004).
Le Gall et al. Immunosuppressive properties of anti-CD3 single-chain Fv and diabody. J Immunol Methods 285(1):111-127 (2004).
Li et al. Cytosine arabinoside promotes cytotoxic effect of T cells on leukemia cells mediated by bispecific antibody. Hum Gene Ther 24:751-760 (2013).
Mcaleese et al. Recruit—TandAbs: harnessing the immune system to kill cancer cells. Future Oncol. 8(6):687-695 (2012).
PCT/US2015/38666 International Preliminary Report on Patentability dated Jan. 12, 2017.
PCT/US2015/38666 International Search Report and Written Opinion dated Dec. 22, 2015.
PCT/US2016/034479 International Search Report and Written Opinion dated Oct. 26, 2016.
Perera et al. V(D)J germline gene repertoire analysis of monoclonal D antibodies and the implications for D epitope specificity. Transfusions 40(7):846-855 (2000).
Reusch et al. A novel tetravalent bispecific TandAb (CD30/CD16A) efficiently recruits NK cells for the lysis of CD30+ tumor cells. MAbs. 6(3):728-739 (2014).
Reusch et al. Characterization of CD33/CD3 Tetravalent Bispecific Tandem Diabodies (TandAbs) for the Treatment of Acute Myeloid Leukemia. Clin Cancer Res 22(23):5829-5838 (2016).
Reusch et al. Characterization of CD33/CD3 Tetravalent Bispecific Tandem Diabodies (TandAbs) for the Treatment of Acute Myeloid Leukemia. Clinical Cancer Research (pp. 1-30) (2016).
Reusch et al. Effect of tetravalent bispecific CD19×CD3 recombinant antibody construct and CD28 costimulation on lysis of malignant B cells from patients with chronic lymphocytic leukemia by autologous T cells. Int J Cancer 112(3):509-518 (2004).
Reusch et al. Journal of Clinical Oncology, (May 20, 2015) vol. 33, No. 15, Supp. Suppl. 1. Abstract No. 7067. Meeting Info: 2015 Annual Meeting of the American Society of Clinical Oncology, ASCO. Chicago, IL, United States. May 29, 2015 (3 pgs.).
Riethmuller. Symmetry breaking: bispecific antibodies, the beginnings, and 50 years on. Cancer Immun. 12:12 (2012).
Stamova et al. Unexpected recombinations in single chain bispecific anti-CD3-anti-CD33 antibodies can be avoided by a novel linker module. Mol Immunol. 49(3):474-482 (2011).
Sutherland et al. SGN-CD33A: a novel CD33-targeting antibody-drug conjugate using a pyrrolobenzodiazepine dimer is active in models of drug-resistant AML. Blood 122:1455-1463 (2013).
Sutherland et al. SGN-CD33A: A Novel CD33-Targeting Antibody-Drug Conjugate Utilizing a Pyrrolobenzodiazepine Dimer is Active in Models of Drug-resistant AML. Blood Journal pp. 1-35 (2013).
Vardiman et al. The 2008 revision of the World Health Organization (WHO) classification of myeloid neoplasms and acute leukemia: rationale and important changes. Blood. 114(5):937-951 (2009).
Kipriyanov et al. Bispecific tandem diabody for tumor therapy with improved antigen binding and pharmacokinetics. J Mol Biol 293:41-56 (1999).
Ando et al., "Gemtuzumab ozogamicin therapy for isolated extramedullary AML relapse after allogeneic hematopoietic stem-cell transplantation," Tohoku Journal of Experimental Medicine, 2010, 220(2):121-126.
Arndt et al., "Redirection of T cells with a first fully humanized bispecific CD33-CD3 antibody efficiently eliminates AML blasts without harming hematopoietic stem cells," Leukemia, 2013, 27(4):964-967.
European Office Action in European Application No. 16804079, dated Sep. 17, 2019, 8 pages.
Kirpriyanov et al., "Bispecific tandem diabody for tumor therapy with improved antigen binding pharmacokinetics," J Mol Biol., 2019, 293:41-56.
PCT/US2016/034479 International Preliminary Report on Patentability dated Dec. 14, 2017.
Rettig et al., "CiTE antibody for AML," Blood, 2018, 132(23):2425-2427.

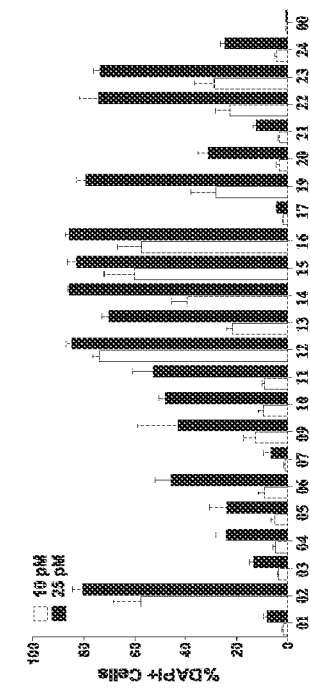
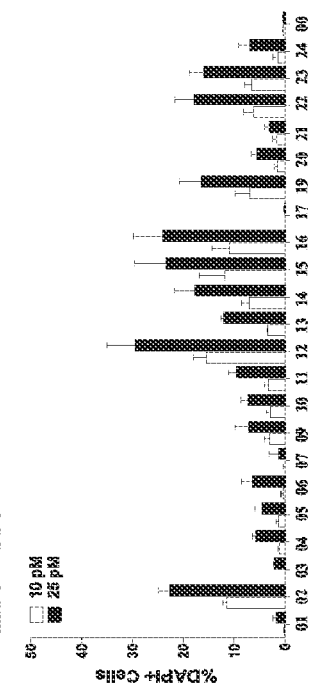
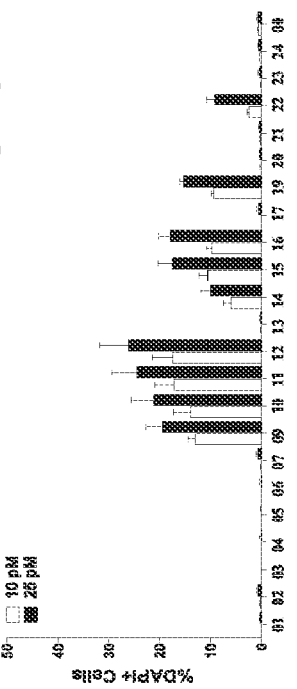
FIG. 6A, FIG. 6B, FIG. 6C, FIG. 6D

```
DPNFWLQVQE SVTVQEGLCV LVPCTFFHPI PYYDKNSPVH GYWFREGAII SRDSPVATNK    60
LDQEVQEETQ GRFRLLGDPS RNNCSLSIVD ARRRDNGSYF FRMERGSTKY SYKSPQLSVH   120
VTDLTHRPKI LIPGTLEPGH SKNLTCSVSW ACEQGTPPIF SWLSAAPTSL GPRTTHSSVL   180
IITPRPQDHG TNLTCQVKFA GAGVTTERTI QLNVTYVPQN PTTGIFPGDG SGKQETRAGV   240
VH                                                                 242
```

SEQ ID NO:93

FIG. 9

DIQMTQSPSSLSASVGDRVTITCRSSTGAVTTSNYANWVQQKPGKAPKGLIGGTNKRAPGVPARFSGSGSGTDFTLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDFSYGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSSAAAGSHHHHHH

SEQ ID NO:98

FIG. 10A

DIQMTQSPSSLSASVGDRVTITCRSSTGAVTTSNYANWVQQKPGKAPKGLIGGTNKRAPGVPARFSGSGSGTDFTLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRAVTDYYYGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSSAAAGSHHHHHH

SEQ ID NO:99

FIG. 10B

DIQMTQSPSSLSASVGDRVTITCRSSTGAVTTSNYANWVQQKPGKAPKGLIGGTNKRAPGVPARFSGSGSGTDFTLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSFGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSSAAAGSHHHHHH

SEQ ID NO:100

FIG. 10C

DIQMTQSPSSLSASVGDRVTITCRSSTGAVTTSNYANWVQQKPGKAPKGLIGGTNKRAPGVPARFSGSGSGTDFTLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSLGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSSAAAGSHHHHHH

SEQ ID NO:101

FIG. 10D

DIQMTQSPSSLSASVGDRVTITCRSSTGAVTTSNYANWVQQKPGKAPKGLIGGTNKRAPGVPARFSGSGSGTDFTLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSFGMDVWGQGTLVTVSSGG
SGGQSVLTQPPSASGTPGQRVTISCSGSRSNIGSNTVNWYQQLPGTAPKLLIYGNNQRPSGVPDRFSGSKSGTSASLAIS
GLQSEDEADYYCATWDDSLIGWVFGGGTKLTVLGGSGGSEVQLVESGGGLVQPGGSLRLSCAASGFTFSTYAMNWVRQAP
GKGLEWVGRIRSKYNNYATYYADSVKDRFTISRDDKNSLYLQMNSLKTEDTAVYYCARHGNFGNSYVSWFAYWGQGTLV
TVSSAAAGSHHHHHH

SEQ ID NO:102

FIG. 10E

DIQMTQSPSSLSASVGDRVTITCRSSTGAVTTSNYANWVQQKPGKAPKGLIGGTNKRAPGVPARFSGSGSGTDFTLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSLGMDVWGQGTLVTVSSGG
SGGQSVLTQPPSASGTPGQRVTISCSGSRSNIGSNTVNWYQQLPGTAPKLLIYGNNQRPSGVPDRFSGSKSGTSASLAIS
GLQSEDEADYYCATWDDSLIGWVFGGGTKLTVLGGSGGSEVQLVESGGGLVQPGGSLRLSCAASGFTFSTYAMNWVRQAP
GKGLEWVGRIRSKYNNYATYYADSVKDRFTISRDDKNSLYLQMNSLKTEDTAVYYCARHGNFGNSYVSWFAYWGQGTLV
TVSSAAAGSHHHHHH

SEQ ID NO:103

FIG. 10F

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLQESGGGVVQPGRSLRLSCAASGFSFSNYGIHWVRQAPGKG
LEWVALISYDGNKKFYADSVKGRFAISRDTSKNTVDLQMTSLRPEDTAVYYCAKDRLESAAFDYWGQGTLVTVSSGGSGG
SSYELTQPPSVSVAPGQTAMITCGGNNIGSTTVHWYQQKPGQAPVLVVYDDNERPSGIPERFSGSNSGSTATLTINRVEA
GDEADYYCQVWDSGSDHVVFGGGTKLTVLGGSGGSEVQLVESGGGLVQPGGSLRLSCAASGFTFSTYAMNWVRQAPGKGL
EWVGRIRSKYNNYATYYADSVKDRFTISRDDKNSLYLQMNSLKTEDTAVYYCARHGNFGNSYVSYFAYWGQGTLVTVSS
AAAGSHHHHHH

SEQ ID NO:104

FIG. 10G

QSVLTQPPSASGTPGQRVTISCSGSRSNIGSNTVNWYQQLPGTAPKLLIYGNNQRPSGVPDRFSGSKSGTSASLAISGLQ
SEDEADYYCATWDDSLIGWVFGGGTKLTVLGGSGGSEVQLVESGGGLVQPGGSLRLSCAASGFTFSTYAMNWVRQAPGKG
LEWVGRIRSKYNNYATYYADSVKDRFTISRDDSKNSLYLQMNSLKTEDTAVYYCARHGNFGNSYVSYFAYWGQGTLVTVS
SGGSGGSDIQMTQSPSSLSASVGDRVTITCRSSTGAVTTSNYANWVQQKPGKAPKALIGGTNKRAPGVPSRFSGSLIGDK
ATLTISSLQPEDFATYYCALWYSNLWVFGQGTKVEIKGGSGGSQVQLVQSGAEVKKPGASVKVSCKASGYTFTSYDINWV
RQAPGQGLEWMGWMNPNSGNTGFAQKFQGRVTMTRDTSTSTVYMELSSLRSEDTAVYYCARDRANTDFSYGMDVWGQGTL
VTVSSAAAGSHHHHHH

SEQ ID NO:105

FIG. 10H

DIQMTQSPSSLSASVGDRVTITCRSSTGAVTTSNYANWVQQKPGKAPKGLIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDFSYGMDVWGQGTLVTVSS**GG
SG**QSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSSAAAGSHHHHHH

SEQ ID NO:106

FIG. 10I

DIQMTQSPSSLSASVGDRVTITCRSSTGAVTTSNYANWVQQKPGKAPKGLIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSFGMDVWGQGTLVTVSS**GG
SG**QSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSSAAAGSHHHHHH

SEQ ID NO:107

FIG. 10J

DIQMTQSPSSLSASVGDRVTITCRSSTGAVTTSNYANWVQQKPGKAPKGLIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSLGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSSAAAGSHHHHHH

SEQ ID NO:108

FIG. 10K

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRAVTDYYYGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSYFAYWGQGTLVT
VSSAAAGSHHHHHH

SEQ ID NO:109

FIG. 10L

DIQMTQSPSSLSASVGDRVTITCRSSTGAVTTSNYANWVQQKPGKAPKGLIGGTNKRAPGVPSRFSGSLIGTDFTLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRAVTDYYYGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSSAAAGSHHHHHH

SEQ ID NO:110

FIG. 10M

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDFSYGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSYFAYWGQGTLVT
VSSAAAGSHHHHHH

SEQ ID NO:111

FIG. 10N

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSFGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSYFAYWGQGTLVT
VSSAAAGSHHHHHH

SEQ ID NO:112

FIG. 10O

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSLGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSYFAYWGQGTLVT
VSSAAAGSHHHHHH

SEQ ID NO:113

FIG. 10P

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGESLKISCKGSGYSFTSYWIGWVRQMPGKG
LEWMGIIYPGDSDTRYSPSFQGQVTISADKSISTAYLQWSSLKASDTAMYYCARHKRGSDAFDIWGQGTTVTVSSGGSGQ
SVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSDVVFGGGTKLTVLGGSGGSEVQLVESGGGLVQPGGSLRLSCAASGFTFSTYAMNWVRQAPGKG
LEWVGRIRSKYNNYATYYADSVKDRFTISRDDSKNSLYLQMNSLKTEDTAVYYCARHGNFGNSYVSYFAYWGQGTLVTVS
SAAAGSHHHHHH

SEQ ID NO:114

FIG. 10Q

EVQLVESGGGLVQPGGSLRLSCAASGFTFSTYAMNWVRQAPGKGLEWVGRIRSKYNNYATYYADSVKDRFTISRDDSKNS
LYLQMNSLKTEDTAVYYCARHGNFGNSYVSYFAYWGQGTLVTVSSGGSGGSQSVLTQPPSVSGAPGQRVTISCTGSSSNI
GAGYDVHWYQQLPGTAPKLLIYGNSNRPSGVPDRFSGSKSGTSASLAITGLQAEDEADYYCQSYDSSLSDVVFGGGTKLT
VLGGSGQVQLVQSGAEVKKPGESLKISCKGSGYSFTSYWIGWVRQMPGKGLEWMGIIYPGDSDTRYSPSFQGQVTISADK
SISTAYLQWSSLKASDTAMYYCARHKRGSDAFDIWGQGTTVTVSSGGSGGSDIQMTQSPSSLSASVGDRVTITCRSSTGA
VTTSNYANWVQQKPGKAPKALIGGTNKRAPGVPSRFSGSLIGDKATLTISSLQPEDFATYYCALWYSNLWVFGQGTKVEI
KAAAGSHHHHHH

SEQ ID NO:115

FIG.10R

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYYMHWVRQAPGQG
LEWMGIINPSGGSTYAQKFQGRVTMTRDTSTSTVYMELSSLRSEDTAVYYCARDVVPAAIDYYGMDVWGQGTTVTVSS**G
GSG**QSVLTQPPSASGTPGQRVTISCSGSSSNIGSNTVNWYQQLPGTAPKLLIYSDNQRPSGVPDRFSGSKSGSSASLAIS
GLQSDDEADYYCATWDDSLNGAVFGGGTKLTVLGGSGGSEVQLVESGGGLVQPGGSLRLSCAASGFTFSTYAMNWVRQAP
GKGLEWVGRIRSKYNNYATYYADSVKDRFTISRDDSKNSLYLQMNSLKTEDTAVYYCARHGNFGNSYVSYFAYWGQGTLV
TVSSAAAGSHHHHHH

SEQ ID NO:116

FIG. 10S

DIQMTQSPSSLSASVGDRVTITCRSSTGAVTTSNYANWVQQKPGKAPKGLIGGTNKRAPGVPSRFSGSLIGTDFTLTISS
LQPEDFATYYCALWYSNLWVFGQGTKVEIKGGSGGSQVQLVQSGAEVKKPGASVKVSCKASGYTFTSYYMHWVRQAPGQG
LEWMGIINPSGGSTYAQKFQGRVTMTRDTSTSTVYMELSSLRSEDTAVYYCARDVVPAAIDYYGMDVWGQGTTVTVSS**G
GSG**QSVLTQPPSASGTPGQRVTISCSGSSSNIGSNTVNWYQQLPGTAPKLLIYSDNQRPSGVPDRFSGSKSGSSASLAIS
GLQSDDEADYYCATWDDSLNGAVFGGGTKLTVLGGSGGSEVQLVESGGGLVQPGGSLRLSCAASGFTFSTYAMNWVRQAP
GKGLEWVGRIRSKYNNYATYYADSVKDRFTISRDDSKNSLYLQMNSLKTEDTAVYYCARHGNFGNSYVSWFAYWGQGTLV
TVSSAAAGSHHHHHH

SEQ ID NO:117

FIG. 10T

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGSSVKVSCKASGGTFSSYAISWVRQAPGQG
LEWMGGIYPIFGSANYAQKFQGRVTITADESTSTAYMELSSLRSEDTAVYYCAREYYYDSSEWAFDIWGQGTLVTVSSGG
SGQSVLTQPPSASGTPGQRVTISCSGSSSNIGSNIVNWYQQLPGTAPKLLIYSNNQRPSGVPDRFSGSKSGTSASLAISG
LQSEDEADYYCAAWDDSLKGYVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSYFAYWGQGTLVT
VSSAAAGSHHHHHH

SEQ ID NO:118

FIG. 10U

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGSSVKVSCKASGGTFSSYGISWVRQAPGQG
LEWMGGIIPIFGSAHYAQKFQGRVTITADESTSTAYMELSSLRSEDTAVYYCAREYYYDSSEWAFDIWGQGTLVTVSSGG
SGQSVLTQPPSASGTPGQRVTISCSGSSSNIGSNTVKWYQQLPGTAPKLLIYSNNQRSSGVPDRFSGSKSGSSASLAISG
LQSEDEADYYCAAWDDSLNGYVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSYFAYWGQGTLVT
VSSAAAGSHHHHHH

SEQ ID NO:119

FIG. 10V

DIQMTQSPSSLSASVGDRVTITCRSSTGAVTTSNYANWVQQKPGKAPKGLIGGTNKRAPGVPSRFSGSLIGTDFTLTISS
LQPEDFATYYCALWYSNLWVFGQGTKVEIKGGSGGSQVQLVQSGAEVKKPGSSVKVSCKASGGTFSSYGISWVRQAPGQG
LEWMGGIIPIFGSAHYAQKFQGRVTITADESTSTAYMELSSLRSEDTAVYYCAREYYYDSSEWAFDIWGQGTLVTVSSGG
SGQSVLTQPPSASGTPGQRVTISCSGSSSNIGSNTVKWYQQLPGTAPKLLIYSNNQRSSGVPDRFSGSKSGSSASLAISG
LQSEDEADYYCAAWDDSLNGYVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSS

SEQ ID NO:120

FIG. 10W

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGSSVKVSCKASGGTFDSYAISWVRQAPGQG
LEWMGGIIPIFGSAHYSQKFQGRVTITADESTSTAYMELSSLRSEDTAVYYCAREYYYDSSEWAFDIWGQGTLVTVSSGG
SGQSVLTQPPSASGTPGQRVTISCSGSSSNIGDNVVNWYQQLPGTAPKLLIYSTNKRPSGVPDRFSGSKSGSSASLAISG
LQSEDEADYYCAAWDDSLSAYVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSYFAYWGQGTLVT
VSSAAAGSHHHHHH
SEQ ID NO:121

FIG. 10X

DIQMTQSPSSLSASVGDRVTITCRSSTGAVTTSNYANWVQQKPGKAPKGLIGGTNKRAPGVPARFSGSGSGTDFTLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDFSYGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSS

SEQ ID NO:123

FIG. 11A

DIQMTQSPSSLSASVGDRVTITCRSSTGAVTTSNYANWVQQKPGKAPKGLIGGTNKRAPGVPARFSGSGSGTDFTLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRAVTDYYYGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSS

SEQ ID NO:124

FIG. 11B

DIQMTQSPSSLSASVGDRVTITCRSSTGAVTTSNYANWVQQKPGKAPKGLIGGTNKRAPGVPARFSGSGSGTDFTLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSFGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSS

SEQ ID NO:125

FIG. 11C

DIQMTQSPSSLSASVGDRVTITCRSSTGAVTTSNYANWVQQKPGKAPKGLIGGTNKRAPGVPARFSGSGSGTDFTLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSLGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSS

SEQ ID NO:126

FIG. 11D

DIQMTQSPSSLSASVGDRVTITCRSSTGAVTTSNYANWVQQKPGKAPKGLIGGTNKRAPGVPARFSGSGSGTDFTLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSFGMDVWGQGTLVTVSSGG
SGGQSVLTQPPSASGTPGQRVTISCSGSRSNIGSNTVNWYQQLPGTAPKLLIYGNNQRPSGVPDRFSGSKSGTSASLAIS
GLQSEDEADYYCATWDDSLIGWVFGGGTKLTVLGGSGGSEVQLVESGGGLVQPGGSLRLSCAASGFTFSTYAMNWVRQAP
GKGLEWVGRIRSKYNNYATYYADSVKDRFTISRDDSKNSLYLQMNSLKTEDTAVYYCARHGNFGNSYVSWFAYWGQGTLV
TVSS

SEQ ID NO:127

FIG. 11E

DIQMTQSPSSLSASVGDRVTITCRSSTGAVTTSNYANWVQQKPGKAPKGLIGGTNKRAPGVPARFSGSGSGTDFTLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSLGMDVWGQGTLVTVSSGG
SGGQSVLTQPPSASGTPGQRVTISCSGSRSNIGSNTVNWYQQLPGTAPKLLIYGNNQRPSGVPDRFSGSKSGTSASLAIS
GLQSEDEADYYCATWDDSLIGWVFGGGTKLTVLGGSGGSEVQLVESGGGLVQPGGSLRLSCAASGFTFSTYAMNWVRQAP
GKGLEWVGRIRSKYNNYATYYADSVKDRFTISRDDSKNSLYLQMNSLKTEDTAVYYCARHGNFGNSYVSWFAYWGQGTLV
TVSS

SEQ ID NO:128

FIG. 11F

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLQESGGGVVQPGRSLRLSCAASGFSFSNYGIHWVRQAPGKG
LEWVALISYDGNKKFYADSVKGRFAISRDTSKNTVDLQMTSLRPEDTAVYYCAKDRLESAAFDYWGQGTLVTVSS**GGSGG
S**SYELTQPPSVSVAPGQTAMITCGGNNIGSTTVHWYQQKPGQAPVLVVYDDNERPSGIPERFSGSNSGSTATLTINRVEA
GDEADYYCQVWDSGSDHVVFGGGTKLTVLGGSGGSEVQLVESGGGLVQPGGSLRLSCAASGFTFSTYAMNWVRQAPGKGL
EWVGRIRSKYNNYATYYADSVKDRFTISRDDSKNSLYLQMNSLKTEDTAVYYCARHGNFGNSYVSYFAYWGQGTLVTVSS

SEQ ID NO:129

FIG. 11G

QSVLTQPPSASGTPGQRVTISCSGSRSNIGSNTVNWYQQLPGTAPKLLIYGNNQRPSGVPDRFSGSKSGTSASLAISGLQ
SEDEADYYCATWDDSLIGWVFGGGTKLTVLGGSGGSEVQLVESGGGLVQPGGSLRLSCAASGFTFSTYAMNWVRQAPGKG
LEWVGRIRSKYNNYATYYADSVKDRFTISRDDSKNSLYLQMNSLKTEDTAVYYCARHGNFGNSYVSYFAYWGQGTLVTVS
SGGSGGSDIQMTQSPSSLSASVGDRVTITCRSSTGAVTTSNYANWVQQKPGKAPKALIGGTNKRAPGVPSRFSGSLIGDK
ATLTISSLQPEDFATYYCALWYSNLWVFGQGTKVEIKGGSGGSQVQLVQSGAEVKKPGASVKVSCKASGYTFTSYDINWV
RQAPGQGLEWMGWMNPNSGNTGFAQKFQGRVTMTRDTSTSTVYMELSSLRSEDTAVYYCARDRANTDFSYGMDVWGQGTL
VTVSS

SEQ ID NO:130

FIG. 11H

DIQMTQSPSSLSASVGDRVTITCRSSTGAVTTSNYANWVQQKPGKAPKGLIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDFSYGMDVWGQGTLVTVSS**GG
SG**QSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSS

SEQ ID NO:131

FIG. 11I

DIQMTQSPSSLSASVGDRVTITCRSSTGAVTTSNYANWVQQKPGKAPKGLIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSFGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSS

SEQ ID NO:132

FIG. 11J

DIQMTQSPSSLSASVGDRVTITCRSSTGAVTTSNYANWVQQKPGKAPKGLIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSLGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSS

SEQ ID NO:133

FIG. 11K

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRAVTDYYYGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSYFAYWGQGTLVT
VSS

SEQ ID NO:134

FIG. 11L

DIQMTQSPSSLSASVGDRVTITCRSSTGAVTTSNYANWVQQKPGKAPKGLIGGTNKRAPGVPSRFSGSLIGTDFTLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRAVTDYYYGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSS

SEQ ID NO:135

FIG. 11M

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDFSYGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSYFAYWGQGTLVT
VSS

SEQ ID NO:136

FIG. 11N

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSFGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSYFAYWGQGTLVT
VSS

SEQ ID NO:137

FIG. 11O

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYDINWVRQAPGQG
LEWMGWMNPNSGNTGFAQKFQGRVTMTRDTSTSTVYMELSSLRSEDTAVYYCARDRANTDYSLGMDVWGQGTLVTVSSGG
SGQSVLTQPPSASGTPGQRVTISCSGSRSNIGSNTVNWYQQLPGTAPKLLIYGNNQRPSGVPDRFSGSKSGTSASLAISG
LQSEDEADYYCATWDDSLIGWVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSYFAYWGQGTLVT
VSS

SEQ ID NO:138

FIG. 11P

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGESLKISCKGSGYSFTSYWIGWVRQMPGKG
LEWMGIIYPGDSDTRYSPSFQGQVTISADKSISTAYLQWSSLKASDTAMYYCARHKRGSDAFDIWGQGTTVTVSSGGSGQ
SVLTQPPSVSGAPGQRVTISCTGSSSNIGAGYDVHWYQQLPGTAPKLLIYGNSNRPSGVPDRFSGSKSGTSASLAITGLQ
AEDEADYYCQSYDSSLSDVVFGGGTKLTVLGGSGGSEVQLVESGGGLVQPGGSLRLSCAASGFTFSTYAMNWVRQAPGKG
LEWVGRIRSKYNNYATYYADSVKDRFTISRDDSKNSLYLQMNSLKTEDTAVYYCARHGNFGNSYVSYFAYWGQGTLVTVS
S

SEQ ID NO:139

FIG. 11Q

EVQLVESGGGLVQPGGSLRLSCAASGFTFSTYAMNWVRQAPGKGLEWVGRIRSKYNNYATYYADSVKDRFTISRDDSKNS
LYLQMNSLKTEDTAVYYCARHGNFGNSYVSYFAYWGQGTLVTVSSGGSGGSQSVLTQPPSVSGAPGQRVTISCTGSSSNI
GAGYDVHWYQQLPGTAPKLLIYGNSNRPSGVPDRFSGSKSGTSASLAITGLQAEDEADYYCQSYDSSLSDVVFGGGTKLT
VLGGSGQVQLVQSGAEVKKPGESLKISCKGSGYSFTSYWIGWVRQMPGKGLEWMGIIYPGDSDTRYSPSFQGQVTISADK
SISTAYLQWSSLKASDTAMYYCARHKRGSDAFDIWGQGTTVTVSSGGSGGSDIQMTQSPSSLSASVGDRVTITCRSSTGA
VTTSNYANWVQQKPGKAPKALIGGTNKRAPGVPSRFSGSLIGDKATLTISSLQPEDFATYYCALWYSNLWVFGQGTKVEI
K

SEQ ID NO:140

FIG. 11R

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGASVKVSCKASGYTFTSYYMHWVRQAPGQG
LEWMGIINPSGGSTSYAQKFQGRVTMTRDTSTSTVYMELSSLRSEDTAVYYCARDVVPAAIDYYGMDVWGQGTTVTVSSG
GSGQSVLTQPPSASGTPGQRVTISCSGSSSNIGSNTVNWYQQLPGTAPKLLIYSDNQRPSGVPDRFSGSKSGSSASLAIS
GLQSDDEADYYCATWDDSLNGAVFGGGTKLTVLGGSGGSEVQLVESGGGLVQPGGSLRLSCAASGFTFSTYAMNWVRQAP
GKGLEWVGRIRSKYNNYATYYADSVKDRFTISRDDSKNSLYLQMNSLKTEDTAVYYCARHGNFGNSYVSYFAYWGQGTLV
TVSS

SEQ ID NO:141

FIG. 11S

DIQMTQSPSSLSASVGDRVTITCRSSTGAVTTSNYANWVQQKPGKAPKGLIGGTNKRAPGVPSRFSGSLIGTDFTLTISS
LQPEDFATYYCALWYSNLWVFGQGTKVEIKGGSGGSQVQLVQSGAEVKKPGASVKVSCKASGYTFTSYYMHWVRQAPGQG
LEWMGIINPSGGSTSYAQKFQGRVTMTRDTSTSTVYMELSSLRSEDTAVYYCARDVVPAAIDYYGMDVWGQGTTVTVSSG
GSGQSVLTQPPSASGTPGQRVTISCSGSSSNIGSNTVNWYQQLPGTAPKLLIYSDNQRPSGVPDRFSGSKSGSSASLAIS
GLQSDDEADYYCATWDDSLNGAVFGGGTKLTVLGGSGGSEVQLVESGGGLVQPGGSLRLSCAASGFTFSTYAMNWVRQAP
GKGLEWVGRIRSKYNNYATYYADSVKDRFTISRDDSKNSLYLQMNSLKTEDTAVYYCARHGNFGNSYVSWFAYWGQGTLV
TVSS

SEQ ID NO:142

FIG. 11T

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGSSVKVSCKASGGTFSSYAISWVRQAPGQG
LEWMGGIYPIFGSANYAQKFQGRVTITADESTSTAYMELSSLRSEDTAVYYCAREYYYDSSEWAFDIWGQGTLVTVSSGG
SGQSVLTQPPSASGTPGQRVTISCSGSSSNIGSNIVNWYQQLPGTAPKLLIYSNNQRPSGVPDRFSGSKSGTSASLAISG
LQSEDEADYYCAAWDDSLKGYVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSYFAYWGQGTLVT
VSS

SEQ ID NO:143

FIG. 11U

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGSSVKVSCKASGGTFSSYGISWVRQAPGQG
LEWMGGIIPIFGSAHYAQKFQGRVTITADESTSTAYMELSSLRSEDTAVYYCAREYYYDSSEWAFDIWGQGTLVTVSSGG
SGQSVLTQPPSASGTPGQRVTISCSGSSSNIGSNTVKWYQQLPGTAPKLLIYSNNQRSSGVPDRFSGSKSGSSASLAISG
LQSEDEADYYCAAWDDSLNGYVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSYFAYWGQGTLVT
VSS

SEQ ID NO:144

FIG. 11V

DIQMTQSPSSLSASVGDRVTITCRSSTGAVTTSNYANWVQQKPGKAPKGLIGGTNKRAPGVPSRFSGSLIGTDFTLTISS
LQPEDFATYYCALWYSNLWVFGQGTKVEIKGGSGGSQVQLVQSGAEVKKPGSSVKVSCKASGGTFSSYGISWVRQAPGQG
LEWMGGIIPIFGSAHYAQKFQGRVTITADESTSTAYMELSSLRSEDTAVYYCAREYYYDSSEWAFDIWGQGTLVTVSSGG
SGQSVLTQPPSASGTPGQRVTISCSGSSSNIGSNTVKWYQQLPGTAPKLLIYSNNQRSSGVPDRFSGSKSGSSASLAISG
LQSEDEADYYCAAWDDSLNGYVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSWFAYWGQGTLVT
VSS

SEQ ID NO:145

FIG.11W

DIQMTQSPSSLSASVGDRVTITCRSSTGAVTTSNYANWVQQKPGKAPKALIGGTNKRAPGVPSRFSGSLIGDKATLTISS
LQPEDFATYYCALWYSNLWVFGQGTKVEIKGGSGGSQVQLVQSGAEVKKPGSSVKVSCKASGGTFDSYAISWVRQAPGQG
LEWMGGIIPIFGSAHYSQKFQGRVTITADESTSTAYMELSSLRSEDTAVYYCAREYYYDSSEWAFDIWGQGTLVTVSSGG
SGQSVLTQPPSASGTPGQRVTISCSGSSSNIGDNVVNWYQQLPGTAPKLLIYSTNKRPSGVPDRFSGSKSGSSASLAISG
LQSEDEADYYCAAWDDSLSAYVFGGGTKLTVLGGSGGSEVQLVESGGGLVQPGGSLRLSCAASGFTFSTYAMNWVRQAPG
KGLEWVGRIRSKYNNYATYYADSVKDRFTISRDDSKNSLYLQMNSLKTEDTAVYYCARHGNFGNSYVSYFAYWGQGTLVT
VSS

SEQ ID NO:146

FIG. 11X

METHODS OF USING BISPECIFIC CD33 AND CD3 BINDING PROTEINS

CROSS REFERENCE

This application is filed pursuant to 35 U.S.C. § 371 as a United States National Phase Application of International Application No. PCT/US2016/034479, filed May 26, 2016, which claims the benefit of U.S Provisional Application No. 62/266,438, filed Dec. 11, 2015; and U.S. Provisional Application No. 62/168,641, filed May 29, 2015, all of which are herein incorporated by reference in their entirety.

SEQUENCE LISTING

The instant application contains a Sequence Listing which has been submitted electronically in ASCII format and is hereby incorporated by reference in its entirety. Said ASCII copy, created on May 25, 2016, is named 45375_705_601_SeqList.txt and is 250,173 bytes in size.

BACKGROUND OF THE INVENTION

Acute myeloid leukemia (AML) is an acute leukemia in adults and children. CD33 is expressed on the majority of myeloblasts in AML. CD33, in some reports, is generally restricted to early multilineage myeloid progenitors and absent from normal pluripotent hematopoietic stem cells.

SUMMARY OF THE INVENTION

Provided herein are binding proteins that specifically bind to human CD33, and bispecific binding proteins that specifically bind to human CD33 and human CD3. Also provided herein are anti-CD33 variable domains and anti-CD3 variable domains for generating a number of bispecific CD33/CD3 binding proteins, such as, for example, tandem diabodies. Also further provided herein are bispecific tandem diabodies that bind to CD33 and CD3 and their use for immunotherapy of acute myeloid leukemia (AML) and other hematologic malignancies, disorders or conditions.

In particular, the binding proteins are provided that show binding to both human as well as cynomolgus monkey CD33. It is demonstrated in the examples that these CD33/CD3 tandem diabodies can re-direct polyclonal CD3$^+$ T-cells from healthy donors, as well as autologous T-cells from AML patients, to effectively lyse CD33$^+$ AML cells at low E:T cell ratios. In this process, which is dependent on the presence of both CD33$^+$ target cells and T-cells, re-directed T-cells are activated, as shown by induction of CD25 and CD69, and stimulated to proliferate. The anti-AML effect of these tandem diabodies is shown to be dependent on the concentration of the antibodies used as well as on the E:T cell ratio. The tandem diabody is tetravalent and has two binding sites for CD33 and two binding sites for CD3. A particular feature of the CD33/CD3 tandem diabodies described herein is that they facilitate potent and efficient apoptosis as a result of bivalent binding that confers avidity to each antigen, namely CD33 and CD3.

In summary, the provided CD33/CD3 binding proteins described herein, in particular tandem diabodies, induce potent cytolysis of CD33$^+$ leukemic cells and primary AML cells in vitro. Examples of bispecific CD33/CD3 binding proteins in the antibody format of tandem diabodies demonstrate cytolytic activity in vivo in cell lines, primary AML cells and in in vivo models with AML cell lines and with patient derived primary AML cells. This indicates high in vivo activity especially noteworthy in the stringent AML PDX model. Further, examples of bispecific CD33/CD3 binding proteins in the antibody format of tandem diabodies demonstrate cytolytic activity ex vivo in samples from patients at all stages of AML, including newly diagnosed, relapsed and refractory patients.

Furthermore, these CD33/CD3 binding proteins described herein are able to achieve a significant lysis of CD33 expressing cells within about four hours. CD33/CD3 binding proteins accordingly exhibit high cytotoxicity at low CD33 densities on the cell surface as well as a high cytotoxicity at low effector: target (E:T) ratios. In addition, CD33/CD3 binding proteins described herein exhibit not only potent CD33 and CD3 binding affinities to the human proteins, but show also excellent crossreactivity with the respective cynomolgus monkey proteins, for example with human:cynomolgous $K_D$ ratios between 5 and 0.2. Furthermore, the CD33/CD3 binding proteins described herein show no significant induction of cytokine release in the absence of CD33$^+$ target cells which is an essential component of the safety profile of these molecules. Moreover, the CD33/CD3 tandem diabodies described herein belong to the class of molecules that have half-lives in the approximate range of 8-24 h, which should allow convenient dosing.

In one aspect, provided herein are CD33 binding proteins that specifically bind to an epitope of human CD33. In some embodiments, the binding proteins comprise a heavy chain variable domain and a light chain variable domain that is derived from human.

In some embodiments, a CD33 binding protein has at least one binding site comprising a light chain variable domain and a heavy chain variable domain, wherein the light chain variable domain comprises a CDR1 consisting of the sequence selected from the group consisting of SEQ ID NOs:21-27, a CDR2 consisting of the sequence selected from the group consisting of SEQ ID NOs:28-34 and a CDR3 consisting of the sequence of the group consisting of SEQ ID NOs:35-41.

In some embodiments, a CD33 binding protein has at least one binding site comprising a light chain variable domain and a heavy chain variable domain, wherein the heavy chain variable domain comprises a CDR1 consisting of the sequence selected from the group consisting of SEQ ID NOs:42-48, a CDR2 consisting of the sequence selected from the group consisting of SEQ ID NOs:49-55 and a CDR3 consisting of a sequences selected from the group consisting of SEQ ID NOs:56-63.

In certain instances, the CDR1, CDR2 and CDR3 of the light chain variable domain is selected from the group consisting of SEQ ID NOs:21, 28 and 35; SEQ ID NOs:22, 29 and 36; SEQ ID NOs:23, 30 and 37; SEQ ID NOs:24, 31 and 38; SEQ ID NOs:25, 32 and 39; SEQ ID NOs:26, 33 and 40; and SEQ ID NOs:27, 34 and 41.

In certain instances, the CDR1, CDR2 and CD3 of the heavy chain variable domain is selected from the group consisting of SEQ ID NOs:42, 49 and 56; SEQ ID NOs:43, 50 and 57; SEQ ID NOs:43, 50 and 58; SEQ ID NOs:43, 50 and 59; SEQ ID NOs:43, 50 and 60; SEQ ID NOs:44, 51 and 61; SEQ ID NOs:45, 52 and 62; SEQ ID NOs:46, 53 and 63; SEQ ID NOs:47, 54 and 63; and SEQ ID NOs:48, 55 and 63.

In certain instances, the human CD33 binding site of a variable heavy chain domain and a variable light chain domain is selected from the group consisting of SEQ ID NO:1 and SEQ ID NO:11; SEQ ID NO:2 and SEQ ID NO:12; SEQ ID NO:3 and SEQ ID NO:13; SEQ ID NO:4 and SEQ ID NO:14; SEQ ID NO:5 and SEQ ID NO:15; SEQ ID NO:6 and SEQ ID NO:16; SEQ ID NO:7 and SEQ ID NO:17; SEQ ID NO:8 and SEQ ID NO:18; SEQ ID NO:9 and SEQ ID NO:19; and SEQ ID NO:10 and SEQ ID NO:20.

In some embodiments, the CD33 epitope is within $_{62}$DQEVQEETQ$_{70}$ (SEQ ID NO:94) amino acid residues 62-70 of SEQ ID NO:93) of human CD33.

In any of the above embodiments, the CD33 binding protein comprises at least one further functional domain. In some instances, the functional domain is an effector domain that binds to an effector cell. In certain instances, the effector domain is a CD3 binding site comprising at least one antibody variable heavy chain domain and at least one variable light chain domain forming an antigen binding site for human CD3.

In certain instances, the CD3 binding site comprises a heavy chain variable domain comprising a CDR1 sequence of STYAMN (SEQ ID NO:72), a CDR2 sequence of RIRSKYNNYATYYADSVKD (SEQ ID NO:73) and a CDR3 sequence of HGNFGNSYVSWFAY (SEQ ID NO:74). In other instances, the CD3 binding site comprises a light chain variable domain comprising a CDR1 sequence of RSSTGAVTTSNYAN (SEQ ID NO:90), a CDR2 sequence of GTNKRAP (SEQ ID NO:91), and a CDR3 sequence of ALWYSNL (SEQ ID NO:92).

In certain instances, the CD3 binding site comprises a heavy chain variable domain of SEQ ID NO:64 and a variable light chain domain of SEQ ID NO:68; a heavy chain variable domain of SEQ ID NO:65 and a variable light chain domain of SEQ ID NO:69; a heavy chain variable domain of SEQ ID NO:66 and a variable light chain domain of SEQ ID NO:70; or a heavy chain variable domain of SEQ ID NO:67 and a variable light chain domain of SEQ ID NO:71.

In any of the above embodiments, the CD33 binding protein is a dimeric protein. In any of the above embodiments, the CD33 binding protein is multifunctional.

In certain instances, the multifunctional CD33 binding protein has bispecificity for CD33 and CD3, wherein the binding specificities are provided by heavy chain variable domain and light chain variable domains for CD33 and CD3 selected from the group consisting of SEQ ID NOs:2, 12, 65 and 69; SEQ ID NOs:3, 13, 65 and 69; SEQ ID NOs:4, 14, 65 and 69; SEQ ID NOs:5, 15, 65 and 69; SEQ ID NOs:1, 11, 64 and 68; SEQ ID NOs:2, 12, 64 and 68; SEQ ID NOs:2, 12, 66 and 70; SEQ ID NOs:4, 14, 66 and 70; SEQ ID NOs:5, 15, 66 and 70; SEQ ID NOs:3, 13, 64 and 68; SEQ ID NOs:3, 13, 67 and 71; SEQ ID NOs:4, 14, 64 and 68; SEQ ID NOs:5, 15, 64 and 68; SEQ ID NOs:7, 17, 64 and 68; SEQ ID NOs:6, 16, 64 and 68; SEQ ID NOs:6, 16, 67 and 71; SEQ ID NOs:8, 18, 64 and 68; SEQ ID NOs:9, 19, 64 and 68; SEQ ID NOs:9, 19, 67 and 71; and SEQ ID NOs:10, 20, 64 and 68.

In another aspect, provided herein are bispecific, antigen-binding tandem diabodies specific to human CD3 and human CD33. In some embodiments, the tandem diabodies comprise a first polypeptide and a second polypeptide, each polypeptide having at least four variable chain domains linked one after another, wherein each polypeptide comprises a variable heavy chain domain specific for human CD33; a variable light chain domain specific for human CD33; a variable heavy chain domain specific for human CD3, and a variable light chain domain specific for human CD3 and wherein in each polypeptide the four variable chain domains are linked with one after another by peptide linkers L1, L2 and L3 in the order of VL(CD3)-L1-VH(CD33)-L2-VL(CD33)-L3-VH(CD3); VH(CD3)-L1-VL(CD33)-L2-VH(CD33)-L3-VL(CD3); VL(CD33)-L1-VH(CD3)-L2-VL(CD3)-L3-VH(CD33); or VH(CD33)-L1-VL(CD3)-L2-VH(CD3)-L3-VL(CD33).

In some embodiments, the VL domain specific to human CD33 comprises a CDR1 consisting of the sequence selected from the group consisting of SEQ ID NOs:21-27, a CDR2 consisting of the sequence selected from the group consisting of SEQ ID NOs:28-34 and a CDR3 consisting of the sequence of the group consisting of SEQ ID NOs:35-41.

In some embodiments, the VH domain specific to human CD33 comprises a CDR1 consisting of the sequence selected from the group consisting of SEQ ID NOs:42-48, a CDR2 consisting of the sequence selected from the group consisting of SEQ ID NOs:49-55 and a CDR3 consisting of a sequences selected from the group consisting of SEQ ID NOs:56-63.

In some embodiments, the CDR1, CDR2 and CDR3 of the VL domain specific to human CD33 are sequences selected from the group consisting of SEQ ID NOs:21, 28 and 35; SEQ ID NOs:22, 29 and 36; SEQ ID NOs:23, 30 and 37; SEQ ID NOs:24, 31 and 38; SEQ ID NOs:25, 32 and 39; SEQ ID NOs:26, 33 and 40; and SEQ ID NOs:27, 34 and 41.

In some embodiments, the CDR1, CDR2 and CDR3 of the VH domain specific to human CD33 are sequences selected from the group consisting of SEQ ID NOs:42, 49 and 56; SEQ ID NOs:43, 50 and 57; SEQ ID NOs:43, 50 and 58; SEQ ID NOs:43, 50 and 59; SEQ ID NOs:43, 50 and 60; SEQ ID NOs:44, 51 and 61; SEQ ID NOs:45, 52 and 62; SEQ ID NOs:46, 53 and 63; SEQ ID NOs:47, 54 and 63; and SEQ ID NOs:48, 55 and 63.

In some embodiments, the VL and VH domains specific to CD33 are sequences selected from the group consisting of SEQ ID NO:1 and SEQ ID NO:11; SEQ ID NO:2 and SEQ ID NO:12; SEQ ID NO:3 and SEQ ID NO:13; SEQ ID NO:4 and SEQ ID NO:14; SEQ ID NO:5 and SEQ ID NO:15; SEQ ID NO:6 and SEQ ID NO:16; SEQ ID NO:7 and SEQ ID NO:17; SEQ ID NO:8 and SEQ ID NO:18; SEQ ID NO:9 and SEQ ID NO:19; and SEQ ID NO:10 and SEQ ID NO:20.

In some embodiments, the VH domain specific for human CD3 comprises a CDR1 sequence of STYAMN (SEQ ID NO:72), a CDR2 sequence of RIRSKYNNYATYYADS-VKD (SEQ ID NO:73) and a CDR3 sequence of HGNFGNSYVSWFAY (SEQ ID NO:74) or HGNFGNSYVSYFAY (SEQ ID NO:75).

In some embodiments, the VL domain specific for human CD3 comprises a CDR1 sequence of RSSTGAVTTSNYAN (SEQ ID NO:90), a CDR2 sequence of GTNKRAP (SEQ ID NO:91), and a CDR3 sequence of ALWYSNL (SEQ ID NO:92).

In some embodiments, the VL and VH domains specific to CD3 are sequences selected from the group consisting of SEQ ID NO:64 and SEQ ID NO:68; SEQ ID NO:65 and SEQ ID NO:69; SEQ ID NO:66 and SEQ ID NO:70; and SEQ ID NO:67 and SEQ ID NO:71.

In some embodiments, each polypeptide comprises four variable chain domains selected from the group consisting of SEQ ID NOs:2, 12, 65 and 69; SEQ ID NOs:3, 13, 65 and 69; SEQ ID NOs:4, 14, 65 and 69; SEQ ID NOs:5, 15, 65 and 69; SEQ ID NOs:1, 11, 64 and 68; SEQ ID NOs:2, 12, 64 and 68; SEQ ID NOs:2, 12, 66 and 70; SEQ ID NOs:4, 14, 66 and 70; SEQ ID NOs:5, 15, 66 and 70; SEQ ID NOs:3, 13, 64 and 68; SEQ ID NOs:3, 13, 67 and 71; SEQ ID NOs:4, 14, 64 and 68; SEQ ID NOs:5, 15, 64 and 68; SEQ ID NOs:7, 17, 64 and 68; SEQ ID NOs:6, 16, 64 and 68; SEQ ID NOs:6, 16, 67 and 71; SEQ ID NOs:8, 18, 64 and 68; SEQ ID NOs:9, 19, 64 and 68; SEQ ID NOs:9, 19, 67 and 71; and SEQ ID NOs:10, 20, 64 and 68.

In some embodiments, linkers L1, L2 and L3 consist of about 12 or less amino acid residues. In certain instances, linkers L1, L2 and L3 are each independently GGSGGS (SEQ ID NO:95), GGSG (SEQ ID NO:96) or GGSGG (SEQ ID NO:97). In other instances, linkers L1 and L3 are GGSGGS (SEQ ID NO:95) and linker L2 is GGSG (SEQ ID NO:96) or GGSGG (SEQ ID NO:97).

In some embodiments, a bispecific tandem diabody, with a C-terminal hexa-histidine (6×His)-tag, comprises a sequence selected from the group consisting of SEQ ID NOs:98-121. In other embodiments, a bispecific tandem diabody is tandem diabody 01 (SEQ ID NO:98), 02 (SEQ ID NO:99), 03 (SEQ ID NO:100), 04 (SEQ ID NO:101), 05 (SEQ ID NO:102), 06 (SEQ ID NO:103), 07 (SEQ ID NO:104), 08 (SEQ ID NO:105), 09 (SEQ ID NO:106), 10 (SEQ ID NO:107), 11 (SEQ ID NO:108), 12 (SEQ ID NO:109), 13 (SEQ ID NO:110), 14 (SEQ ID NO:111), 15 (SEQ ID NO:112), 16 (SEQ ID NO:113), 17 (SEQ ID NO:114), 18 (SEQ ID NO:115), 19 (SEQ ID NO:116), 20 (SEQ ID NO:117), 21 (SEQ ID NO:118), 22 (SEQ ID NO:119), 23 (SEQ ID NO:120), or 24 (SEQ ID NO:121).

In some embodiments, a bispecific tandem diabody comprises a sequence selected from the group consisting of SEQ ID NOs:123-146. In other embodiments, a bispecific tandem diabody is tandem diabody 01 (SEQ ID NO:123), 02 (SEQ ID NO:124), 03 (SEQ ID NO:125), 04 (SEQ ID NO:126), 05 (SEQ ID NO:127), 06 (SEQ ID NO:128), 07 (SEQ ID NO:129), 08 (SEQ ID NO:130), 09 (SEQ ID NO:131), 10 (SEQ ID NO:132), 11 (SEQ ID NO:133), 12 (SEQ ID NO:134), 13 (SEQ ID NO:135), 14 (SEQ ID NO:136), 15 (SEQ ID NO:137), 16 (SEQ ID NO:138), 17 (SEQ ID NO:139), 18 (SEQ ID NO:140), 19 (SEQ ID NO:141), 20 (SEQ ID NO:142), 21 (SEQ ID NO:143), 22 (SEQ ID NO:144), 23 (SEQ ID NO:145), or 24 (SEQ ID NO:146). In some embodiments, a bispecific tandem diabody is tandem diabody 01 (SEQ ID NO: 123). In some embodiments, a bispecific tandem diabody is tandem diabody 02 (SEQ ID NO: 124). In some embodiments, a bispecific tandem diabody is tandem diabody 03 (SEQ ID NO: 125). In some embodiments, a bispecific tandem diabody is tandem diabody 04 (SEQ ID NO: 126). In some embodiments, a bispecific tandem diabody is tandem diabody 05 (SEQ ID NO: 127). In some embodiments, a bispecific tandem diabody is tandem diabody 06 (SEQ ID NO: 128). In some embodiments, a bispecific tandem diabody is tandem diabody 07 (SEQ ID NO: 129). In some embodiments, a bispecific tandem diabody is tandem diabody 08 (SEQ ID NO: 130). In some embodiments, a bispecific tandem diabody is tandem diabody 09 (SEQ ID NO: 131). In some embodiments, a bispecific tandem diabody is tandem diabody 10 (SEQ ID NO: 132). In some embodiments, a bispecific tandem diabody is tandem diabody 11 (SEQ ID NO: 133). In some embodiments, a bispecific tandem diabody is tandem diabody 12 (SEQ ID NO: 134). In some embodiments, a bispecific tandem diabody is tandem diabody 13 (SEQ ID NO: 135). In some embodiments, a bispecific tandem diabody is tandem diabody 14 (SEQ ID NO: 136). In some embodiments, a bispecific tandem diabody is tandem diabody 15 (SEQ ID NO: 137). In some embodiments, a bispecific tandem diabody is tandem diabody 16 (SEQ ID NO: 138). In some embodiments, a bispecific tandem diabody is tandem diabody 17 (SEQ ID NO: 139). In some embodiments, a bispecific tandem diabody is tandem diabody 18 (SEQ ID NO: 140). In some embodiments, a bispecific tandem diabody is tandem diabody 19 (SEQ ID NO: 141). In some embodiments, a bispecific tandem diabody is tandem diabody 20 (SEQ ID NO: 142). In some embodiments, a bispecific tandem diabody is tandem diabody 21 (SEQ ID NO: 143). In some embodiments, a bispecific tandem diabody is tandem diabody 22 (SEQ ID NO: 144). In some embodiments, a bispecific tandem diabody is tandem diabody 23 (SEQ ID NO: 145). In some embodiments, a bispecific tandem diabody is tandem diabody 24 (SEQ ID NO: 146).

In some embodiments, the bispecific, antigen-binding tandem diabodies possess binding $K_D$ of 50 nM or less to CD33 on CD33$^+$ tumor cells selected from HL-60, KG-1, and U-937. In some embodiments, the bispecific, antigen-binding tandem diabodies possess binding $K_D$ of 10 nM or less to CD33 on CD33$^+$ tumor cells selected from HL-60, KG-1, and U-937. In some embodiments, the bispecific, antigen-binding tandem diabodies possess binding $K_D$ of 15 nM or less to CD33 on CD33$^+$ HL-60 tumor cells.

In some embodiments, the bispecific, antigen-binding tandem diabodies specifically binds to an epitope of human CD33 which is within $_{62}$DQEVQEETQ$_{70}$ (SEQ ID NO:94) (amino acid residues 62-70 of SEQ ID NO:93) of human CD33.

In another aspect, provided herein are polynucleotides encoding a CD33 binding protein or bispecific, tandem diabody of any of the above embodiments. In another aspect, provided herein are vectors comprising the described polynucleotides. In another aspect, provided herein are host cells transformed with the described vectors.

In yet another aspect, provided herein are pharmaceutical compositions comprising a CD33 binding protein or bispecific, tandem diabody of any of the above embodiments and a pharmaceutically acceptable carrier.

In yet another aspect, provided herein methods of producing a CD33 binding protein or bispecific, tandem diabody of any of the above embodiments comprising introducing into a host cell a polynucleotide encoding a CD33 binding protein or bispecific, tandem diabody of any of the above embodiments, or a vector comprising the described polynucleotides, culturing the host cell under conditions whereby the CD33 binding protein or the bispecific tandem diabody is expressed, and purifying the expressed CD33 binding protein or the bispecific tandem diabody.

Also provided herein are methods for the treatment of a CD33$^+$ cancer comprising the administration of a bispecific, tandem diabody of any of the above embodiments to an individual suffering from CD33$^+$ cancer. In some embodiments, the CD33$^+$ cancer is acute myeloid leukemia (AML), acute lymphoblastic leukemia (ALL), precursor B-cell lymphoblastic leukemia, myeloid sarcoma, multiple myeloma, acute lymphoma, acute lymphoblastic lymphoma or chronic myelomonocytic leukemia (CMML). In some embodiments, the CD33$^+$ cancer is acute myeloid leukemia (AML). In some embodiments, the CD33$^+$ cancer is multiple myeloma. In some embodiments, the CD33$^+$ cancer is acute lymphoblastic leukemia (ALL).

Also provided herein are methods for the treatment of acute myeloid leukemia (AML) comprising the administration of a bispecific, tandem diabody of any of the above embodiments to an individual suffering from AML. In some embodiments, the AML is AML with Recurrent Genetic Abnormalities, AML with myelodysplasia-related changes, Therapy-related myeloid neoplasms, Myeloid sarcoma, Myeloid proliferations related to Down syndrome, Blastic plasmacytoid dendritic cell neoplasm, or AML not otherwise categorized. In some embodiments, the AML is AML-M0, AML-M1, AML-M2, AML-M3, AML-M4, AML-M5, AML-M6, or AML-M7. In further embodiments, the AML is newly diagnosed, relapsed, or refractory.

Also provided herein are methods for the treatment of myeloid dysplastic syndrome (MDS) comprising the administration of a bispecific, tandem diabody of any of the above embodiments to an individual suffering from MDS.

Also provided herein are methods for the treatment of myeloproliferative disease (MPD) comprising the administration of a bispecific, tandem diabody of any of the above embodiments to an individual suffering from MPD.

Also provided herein are methods for the treatment of chronic myelomonocytic leukemia (CMML) comprising the administration of a bispecific, tandem diabody of any of the above embodiments to an individual suffering from CMML.

Also provided herein are methods for the treatment of immune suppression by myeloid derived suppressor cells (MDSCs) comprising the administration of a bispecific, tandem diabody in any of the above embodiments to an individual suffering from immune suppression.

In the above methods for the treatment, in certain instances, the methods further comprise administering cytarabine, azacitidine, decitabine, an anthracycline (e.g., daunorubicin, idarubicin, doxorubicin, and the like), amsacrine, fludarabine, clofarabine, cladribine, nelarabine, methotrexate, bortezomib, carfilzomib, melphalan, ibrutinib, thalidomide, lenalidomide, pomalidomide, apremilast, an epipodophyllotoxin (e.g., etoposide, teniposide, and the like), an anthracenedione (e.g., mitoxantrone, pixantrone, losoxantrone, piroxantrone, ametantrone and the like), an anti-CD20 agent (e.g., rituximab, ocrelizumab, ofatumumab, and the like) or combinations thereof.

Provided herein are methods for the treatment of acute myelogenous leukemia (AML) in a patient having received hematopoietic stem cell transplantation comprising administering a therapeutically effective amount of a protein that binds to human CD33 and human CD3. In some embodiments are provided methods, wherein the transplantation is allogenic. In some embodiments are provided methods, wherein the transplantation is autologous. In some embodiments are provided methods, wherein the patient does not receive a conditioning regimen. In some embodiments are provided methods, further comprising administering a conditioning regimen to the patient. In some embodiments are provided methods, wherein the conditioning regimen is myeloablative. In some embodiments are provided methods, wherein the conditioning regimen is non-myeloablative.

In any of the above embodiments, are provided methods, wherein the protein is administered after the conditioning regimen. In any of the above embodiments, are provided methods, wherein the patient is in complete remission. In any of the above embodiments, are provided methods, wherein the patient has minimal residual disease. In any of the above embodiments, are provided methods, wherein the patient has failed chemotherapy or radiation. In any of the above embodiments, are provided methods, wherein the patient has failed inductive chemotherapy. In any of the above embodiments, are provided methods, wherein the patient has failed consolidation or maintenance (postremission) chemotherapy.

In any of the above embodiments, are provided methods, wherein the AML is relapsed. In any of the above embodiments, are provided methods, wherein the AML is refractory. In any of the above embodiments, are provided methods, wherein the AML is high risk and in remission. In any of the above embodiments, are provided methods, wherein the protein is administered immediately after the hematopoietic stem cell transplantation. In any of the above embodiments, are provided methods, wherein the protein is administered three days post-hematopoietic stem cell transplantation. In any of the above embodiments, are provided methods, wherein the protein is administered seven days post-hematopoietic stem cell transplantation. In any of the above embodiments, are provided methods, wherein the protein is administered two weeks post-hematopoietic stem cell transplantation. In any of the above embodiments, are provided methods, wherein the protein is administered four weeks post-hematopoietic stem cell transplantation. In any of the above embodiments, are provided methods, wherein the protein is administered for a period of time selected from a group consisting of four weeks, eight weeks, three months, four months, six months, eight months, ten months, twelve months, eighteen months, and twenty-four months. In any of the above embodiments, are provided methods, wherein the protein is administered at time of progression in allogeneic setting, with donor lymphocytes. In any of the above embodiments, are provided methods, wherein the protein is administered at time of progression in allogeneic setting, without donor lymphocytes.

In any of the above embodiments, are provided methods, wherein the protein comprises heavy and light chain domains specific for human CD33 and human CD3. In any of the above embodiments, are provided methods, wherein the protein is an antibody or antibody derivative. In any of the above embodiments, are provided methods, wherein the protein comprises Fab, Fab', or F(ab')2 fragments. In any of the above embodiments, are provided methods, wherein the protein is a single-chain Fv, tandem single-chain Fv, bi-specific T-cell engager, dual affinity retargeting antibody, diabody, or bispecific tandem diabody. In any of the above embodiments, are provided methods, wherein the protein is a bispecific tandem diabody. In any of the above embodiments, are provided methods, wherein the tandem diabody comprises a first polypeptide and a second polypeptide, each polypeptide having at least four variable chain domains linked one after another, wherein each polypeptide comprises a variable heavy chain (VH) domain specific to human CD33; a variable light chain (VL) domain specific to human CD33; a VH domain specific for human CD3, and a VL domain specific for human CD3. In any of the above embodiments, are provided methods, wherein in each polypeptide, the four variable chain domains are linked with one after another by peptide linkers L1, L2 and L3 in the order of: VL(CD3)-L1-VH(CD33)-L2-VL(CD33)-L3-VH(CD3); VH(CD3)-L1-VL(CD33)-L2-VH(CD33)-L3-VL(CD3); VL(CD33)-L1-VH(CD3)-L2-VL(CD3)-L3-VH(CD33); or VH(CD33)-L1-VL(CD3)-L2-VH(CD3)-L3-VL(CD33). In any of the above embodiments, are provided methods, wherein the VL domain specific to human CD33 comprises a CDR1 consisting of the sequence selected from the group consisting of SEQ ID NOs:21-27, a CDR2 consisting of the sequence selected from the group consisting of SEQ ID NOs:28-34 and a CDR3 consisting of the sequence of the group consisting of SEQ ID NOs:35-41.

In any of the above embodiments, are provided methods, wherein the VH domain specific to human CD33 comprises a CDR1 consisting of the sequence selected from the group consisting of SEQ ID NOs:42-48, a CDR2 consisting of the sequence selected from the group consisting of SEQ ID NOs:49-55 and a CDR3 consisting of a sequences selected from the group consisting of SEQ ID NOs:56-63. In any of the above embodiments, are provided methods, wherein the CDR1, CDR2 and CDR3 of the VL domain specific to human CD33 are sequences selected from the group consisting of: SEQ ID NOs:21, 28 and 35; SEQ ID NOs:22, 29 and 36; SEQ ID NOs:23, 30 and 37; SEQ ID NOs:24, 31 and 38; SEQ ID NOs:25, 32 and 39; SEQ ID NOs:26, 33 and 40; and SEQ ID NOs:27, 34 and 41. In any of the above embodiments, are provided methods, wherein the CDR1, CDR2 and CDR3 of the VH domain specific to CD33 are sequences selected from the group consisting of: SEQ ID NOs:42, 49 and 56; SEQ ID NOs:43, 50 and 57; SEQ ID NOs:43, 50 and 58; SEQ ID NOs:43, 50 and 59; SEQ ID NOs:43, 50 and 60; SEQ ID NOs:44, 51 and 61; SEQ ID NOs:45, 52 and 62; SEQ ID NOs:46, 53 and 63; SEQ ID NOs:47, 54 and 63; and SEQ ID NOs:48, 55 and 63. In any of the above embodiments, are provided methods, wherein the VL and VH domains specific to CD33 are sequences selected from the group consisting of: SEQ ID NO:1 and SEQ ID NO:11; SEQ ID NO:2 and SEQ ID NO:12; SEQ ID NO:3 and SEQ ID NO:13; SEQ ID NO:4 and SEQ ID NO:14; SEQ ID NO:5 and SEQ ID NO:15; SEQ ID NO:6 and SEQ ID NO:16; SEQ ID NO:7 and SEQ ID NO:17; SEQ ID NO:8 and SEQ ID NO:18; SEQ ID NO:9 and SEQ ID NO:19; and SEQ ID NO:10 and SEQ ID NO:20. In any of the above embodiments, are provided methods, wherein the VH domain specific for human CD3 comprises a CDR1 sequence of STYAMN (SEQ ID NO:72), a CDR2 sequence of RIRSKYNNYATYYADSVKD (SEQ ID NO:73) and a CDR3 sequence of HGNFGNSYVSWFAY (SEQ ID NO:74) or HGNFGNSYVSYFAY (SEQ ID NO:75). In any of the above embodiments, are provided methods, wherein the VL domain specific for human CD3 comprises a CDR1 sequence of RSSTGAVTTSNYAN (SEQ ID NO:90), a CDR2 sequence of GTNKRAP (SEQ ID NO:91), and a CDR3 sequence of ALWYSNL (SEQ ID NO:92). In any of the above embodiments, are provided methods, wherein the VL and VH domains specific to CD3 are sequences selected from the group consisting of: SEQ ID NO:64 and SEQ ID NO:68; SEQ ID NO:65 and SEQ ID NO:69; SEQ ID NO:66 and SEQ ID NO:70; and SEQ ID NO:67 and SEQ ID NO:71. In any of the above embodiments, are provided methods, wherein each polypeptide comprises four variable chain domains selected from the group consisting of: SEQ ID NOs:2, 12, 65 and 69; SEQ ID NOs:3, 13, 65 and 69; SEQ ID NOs:4, 14, 65 and 69; SEQ ID NOs:5, 15, 65 and 69; SEQ ID NOs:1, 11, 64 and 68; SEQ ID NOs:2, 12, 64 and 68; SEQ ID NOs:2, 12, 66 and 70; SEQ ID NOs:4, 14, 66 and 70; SEQ ID NOs:5, 15, 66 and 70; SEQ ID NOs:3, 13, 64 and 68; SEQ ID NOs:3, 13, 67 and 71; SEQ ID NOs:4, 14, 64 and 68; SEQ ID NOs:5, 15, 64 and 68; SEQ ID NOs:7, 17, 64 and 68; SEQ ID NOs:6, 16, 64 and 68; SEQ ID NOs:6, 16, 67 and 71; SEQ ID NOs:8, 18, 64 and 68; SEQ ID NOs:9, 19, 64 and 68; SEQ ID NOs:9, 19, 67 and 71; and SEQ ID NOs:10, 20, 64 and 68. In any of the above embodiments, are provided methods, wherein linkers L1, L2 and L3 consist of about 12 or less amino acid residues. In any of the above embodiments, are provided methods, wherein linkers L1, L2 and L3 are each independently selected from GGSGGS (SEQ ID NO:95), GGSG (SEQ ID NO:96) or GGSGG (SEQ ID NO:97). In any of the above embodiments, are provided methods, wherein the tandem diabody, with C-terminal hexa-histidine (6×His)-tag, has a sequence selected from the group consisting of SEQ ID NOs:98-121. In any of the above embodiments, are provided methods, wherein the tandem diabody is tandem diabody 01 (SEQ ID NO:98), 02 (SEQ ID NO:99), 03 (SEQ ID NO:100), 04 (SEQ ID NO:101), 05 (SEQ ID NO:102), 06 (SEQ ID NO:103), 07 (SEQ ID NO:104), 08 (SEQ ID NO:105), 09 (SEQ ID NO:106), 10 (SEQ ID NO:107), 11 (SEQ ID NO:108), 12 (SEQ ID NO:109), 13 (SEQ ID NO:110), 14 (SEQ ID NO:111), 15 (SEQ ID NO:112), 16 (SEQ ID NO:113), 17 (SEQ ID NO:114), 18 (SEQ ID NO:115), 19 (SEQ ID NO:116), 20 (SEQ ID NO:117), 21 (SEQ ID NO:118), 22 (SEQ ID NO:119), 23 (SEQ ID NO:120), or 24 (SEQ ID NO:121).

In any of the above embodiments, are provided methods, wherein the tandem diabody has a sequence selected from the group consisting of SEQ ID NOs:123-146. In any of the above embodiments, are provided methods, wherein the tandem diabody is tandem diabody 01 (SEQ ID NO:123), 02 (SEQ ID NO:124), 03 (SEQ ID NO:125), 04 (SEQ ID NO:126), 05 (SEQ ID NO:127), 06 (SEQ ID NO:128), 07 (SEQ ID NO:129), 08 (SEQ ID NO:130), 09 (SEQ ID NO:131), 10 (SEQ ID NO:132), 11 (SEQ ID NO:133), 12 (SEQ ID NO:134), 13 (SEQ ID NO:135), 14 (SEQ ID NO:136), 15 (SEQ ID NO:137), 16 (SEQ ID NO:138), 17 (SEQ ID NO:139), 18 (SEQ ID NO:140), 19 (SEQ ID NO:141), 20 (SEQ ID NO:142), 21 (SEQ ID NO:143), 22 (SEQ ID NO:144), 23 (SEQ ID NO:145), or 24 (SEQ ID NO:146).

In any of the above embodiments, are provided methods, wherein the method further comprises administering cytarabine, azacitidine, decitabine, anthracycline, fludarabine, clofarabine, cladribine, nelarabine, methotrexate, bortezomib, carfilzomib, melphalan, ibrutinib, thalidomide, lenalidomide, pomalidomide, apremilast, an epipodophyllotoxin, an anthracenedione, an anti-CD20 agent or combinations thereof. In any of the above embodiments, are provided methods, wherein the AML is AML with Recurrent Genetic Abnormalities, AML with myelodysplasia-related changes, Therapy-related myeloid neoplasms, Myeloid sarcoma, Myeloid proliferations related to Down syndrome, Blastic plasmacytoid dendritic cell neoplasm, or AML not otherwise categorized. In any of the above embodiments, are provided methods, wherein the AML is AML-M0, AML-M1, AML-M2, AML-M3, AML-M4, AML-M5, AML-M6, or AML-M7. In any of the above embodiments, are provided methods, wherein administering the protein, in a patient having received allogenic hematopoietic stem cell transplant, after receiving a myeloablative conditioning regimen, results in improved overall response rate to therapy with the protein. In any of the above embodiments, are provided methods, wherein administering the protein, in a patient having received allogenic hematopoietic stem cell transplant, after receiving a non-myeloablative conditioning regimen, results in improved overall response rate to therapy with the protein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 Screening cytotoxicity assays in CD33+ AML cell lines. Parental HL-60 (A,B) and KG-1a (C,D) cells were incubated with 10 pM (approx. 1 ng/mL) and 25 pM (approx. 2.5 ng/mL) of one of 22 CD33/CD3 tandem diabody molecules or a non-binding control tandem diabody (00) and healthy donor T-cells at an E:T cell ratio of either 1:1 (A,C) or 5:1 (B,D) as indicated. After 48 hours, cell counts were determined and cytotoxicity was assessed with DAPI staining to quantify drug-specific cytotoxicity. Results are shown as mean±SEM for the percentage of DAPI$^+$ cells from 3 independent experiments performed in duplicate wells. Qualitatively similar results were obtained when cytotoxicity was expressed as the percentage of specific cytotoxicity.

FIG. 9 Amino acid sequence of extracellular domain of human CD33 (aa 18-259) (SEQ ID NO: 93);

FIG. 10 Amino acid sequences
- (A) complete sequence of tandem diabody 1 with C-terminal hexa-histidine (6×His)-tag (SEQ ID NO:98);
- (B) complete sequence of tandem diabody 2 with C-terminal hexa-histidine (6×His)-tag (SEQ ID NO:99);
- (C) complete sequence of tandem diabody 3 with C-terminal hexa-histidine (6×His)-tag (SEQ ID NO:100);
- (D) complete sequence of tandem diabody 4 with C-terminal hexa-histidine (6×His)-tag (SEQ ID NO:101);
- (E) complete sequence of tandem diabody 5 with C-terminal hexa-histidine (6×His)-tag (SEQ ID NO:102);
- (F) complete sequence of tandem diabody 6 with C-terminal hexa-histidine (6×His)-tag (SEQ ID NO:103);
- (G) complete sequence of tandem diabody 7 with C-terminal hexa-histidine (6×His)-tag (SEQ ID NO:104);
- (H) complete sequence of tandem diabody 8 with C-terminal hexa-histidine (6×His)-tag (SEQ ID NO:105);
- (I) complete sequence of tandem diabody 9 with C-terminal hexa-histidine (6×His)-tag (SEQ ID NO:106);
- (J) complete sequence of tandem diabody 10 with C-terminal hexa-histidine (6×His)-tag (SEQ ID NO:107);
- (K) complete sequence of tandem diabody 11 with C-terminal hexa-histidine (6×His)-tag (SEQ ID NO:108);
- (L) complete sequence of tandem diabody 12 with C-terminal hexa-histidine (6×His)-tag (SEQ ID NO:109);
- (M) complete sequence of tandem diabody 13 with C-terminal hexa-histidine (6×His)-tag (SEQ ID NO:110);
- (N) complete sequence of tandem diabody 14 with C-terminal hexa-histidine (6×His)-tag (SEQ ID NO:111);
- (O) complete sequence of tandem diabody 15 with C-terminal hexa-histidine (6×His)-tag (SEQ ID NO:112);
- (P) complete sequence of tandem diabody 16 with C-terminal hexa-histidine (6×His)-tag (SEQ ID NO:113);
- (Q) complete sequence of tandem diabody 17 with C-terminal hexa-histidine (6×His)-tag (SEQ ID NO:114);
- (R) complete sequence of tandem diabody 18 with C-terminal hexa-histidine (6×His)-tag (SEQ ID NO:115);
- (S) complete sequence of tandem diabody 19 with C-terminal hexa-histidine (6×His)-tag (SEQ ID NO:116);
- (T) complete sequence of tandem diabody 20 with C-terminal hexa-histidine (6×His)-tag (SEQ ID NO:117);
- (U) complete sequence of tandem diabody 21 with C-terminal hexa-histidine (6×His)-tag (SEQ ID NO:118);
- (V) complete sequence of tandem diabody 22 with C-terminal hexa-histidine (6×His)-tag (SEQ ID NO:119);
- (W) complete sequence of tandem diabody 23 with C-terminal hexa-histidine (6×His)-tag (SEQ ID NO:120); and
- (X) complete sequence of tandem diabody 24 with C-terminal hexa-histidine (6×His)-tag (SEQ ID NO:121).
Underlined sequences represent linkers L1, L2 and L3.

FIG. 11 Amino acid sequences (A) complete sequence of tandem diabody 1 (SEQ ID NO:123);
(B) complete sequence of tandem diabody 2 (SEQ ID NO:124);
(C) complete sequence of tandem diabody 3 (SEQ ID NO:125);
(D) complete sequence of tandem diabody 4 (SEQ ID NO:126);
(E) complete sequence of tandem diabody 5 (SEQ ID NO:127);
(F) complete sequence of tandem diabody 6 (SEQ ID NO:128);
(G) complete sequence of tandem diabody 7 (SEQ ID NO:129);
(H) complete sequence of tandem diabody 8 (SEQ ID NO:130);
(I) complete sequence of tandem diabody 9 (SEQ ID NO:131);
(J) complete sequence of tandem diabody 10 (SEQ ID NO:132);
(K) complete sequence of tandem diabody 11 (SEQ ID NO:133);
(L) complete sequence of tandem diabody 12 (SEQ ID NO:134);
(M) complete sequence of tandem diabody 13 (SEQ ID NO:135);
(N) complete sequence of tandem diabody 14 (SEQ ID NO:136);
(O) complete sequence of tandem diabody 15 (SEQ ID NO:137);
(P) complete sequence of tandem diabody 16 (SEQ ID NO:138);
(Q) complete sequence of tandem diabody 17 (SEQ ID NO:139);
(R) complete sequence of tandem diabody 18 (SEQ ID NO:140);
(S) complete sequence of tandem diabody 19 (SEQ ID NO:141);
(T) complete sequence of tandem diabody 20 (SEQ ID NO:142);
(U) complete sequence of tandem diabody 21 (SEQ ID NO:143);
(V) complete sequence of tandem diabody 22 (SEQ ID NO:144);
(W) complete sequence of tandem diabody 23 (SEQ ID NO:145); and
(X) complete sequence of tandem diabody 24 (SEQ ID NO:146). Underlined sequences represent linkers L1, L2 and L3.

DETAILED DESCRIPTION OF THE INVENTION

Figure 1:
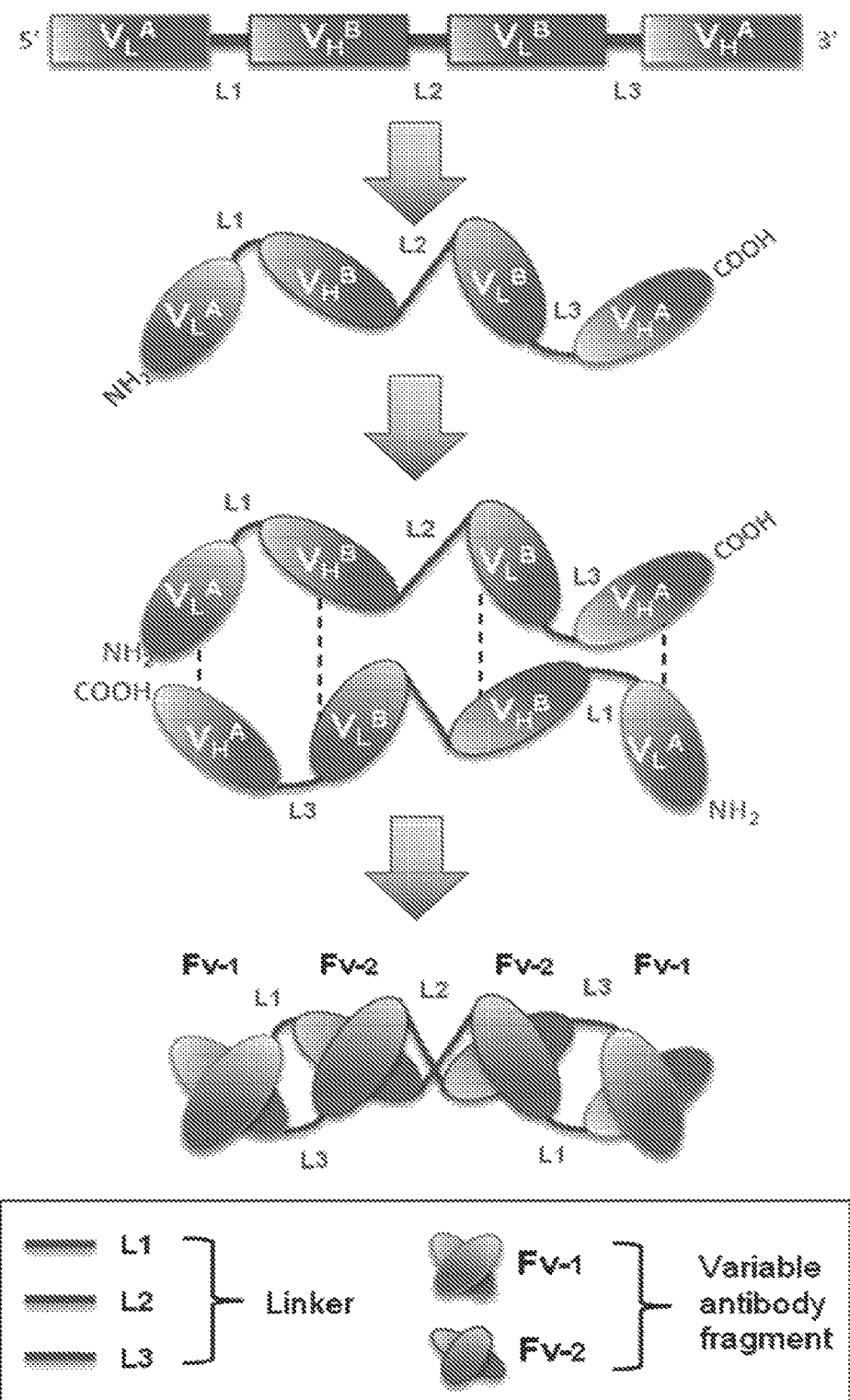
FIG. 1 Schematic representation of the gene organization and a domain order of CD3/CD33 tandem diabodies (TandAb®). Tandem diabodies are expressed as a single polypeptide comprised of four variable domains connected via short peptide linkers L1, L2 and L3. Following expression, two monomeric polypeptides associate non-covalently head-to-tail to form the functional homodimeric tandem diabody molecule. L1, L2, L3: Linker; $V_H$: Heavy chain variable domain; $V_L$: Light chain variable domain.

According to a first aspect, described herein are binding proteins having specificity for at least CD33, preferably human CD33. In some embodiments, the CD33 binding proteins have specificity for human and cynomolgus CD33, i.e. are cross-reactive. In some embodiments, these cross-reactive binding proteins bind to human and cynomolgous CD33 with similar affinity.

CD33 is expressed on myeloid cells, for example, such as the blasts of acute myeloid leukemia (AML). For the isolation of antibody domains specific for CD33, such as human CD33, antibody libraries may be screened. For example IgM phage display libraries can be screened by employing, for example, a recombinant CD33-Fc fusion protein containing amino acids 1-243 of the extracellular domain of human CD33 (FIG. 9, SEQ ID NO:93).

In some embodiments the CD33 binding protein has at least one CD33 binding site comprising a light chain variable domain and a heavy chain variable domain. The light chain variable domain comprises the light chain CDR1, CDR2 and CDR3 and the heavy chain variable domain comprises the heavy chain CDR1, CDR2 and CDR3. In some embodiments these light chain CDRs (CDR1, CDR2 and CDR3) are selected from the human CDR sequences shown in Table 1 (SEQ ID NOs:21-41). In certain instances, the light chain CDR1 is selected from SEQ ID NOs:21-27. In certain instances, the light chain CDR2 is selected from SEQ ID NOs:28-34. In certain instances, the light chain CDR3 is selected from SEQ ID NOs:35-41.

In some embodiments these heavy chain CDRs (heavy chain CDR1, CDR2 and CDR3) are selected from the human CDR sequences shown in Table 2 (SEQ ID NOs:42-63). In certain instances, the heavy chain CDR1 is selected from SEQ ID NOs:42-48. In certain instances, the heavy chain CDR2 is selected from SEQ ID NOs:49-55. In certain instances, the heavy chain CDR3 is selected from SEQ ID NOs:56-63.

In some embodiments, the light and heavy CDRs are selected without the surrounding framework sequences of the respective variable domains, which include framework sequences from other immunoglobulins or consensus framework regions, optionally are further mutated and/or replaced by other suitable framework sequences. Therefore provided herein in some embodiments, is a CD33 binding protein comprising a light chain variable domain, wherein the light chain CDR1 is SEQ ID NO:21; the light chain CDR2 is SEQ ID NO:28 and the light chain CDR3 is SEQ ID NO:35. In some embodiments, a CD33 binding protein comprises a light chain variable domain, wherein the light chain CDR1 is SEQ ID NO:22; the light chain CDR2 is SEQ ID NO:29 and the light chain CDR3 is SEQ ID NO:36. In some embodiments, a CD33 binding protein comprises a light chain variable domain, wherein the light chain CDR1 is SEQ ID NO:23; the light chain CDR2 is SEQ ID NO:30 and the light chain CDR3 is SEQ ID NO:37. In some embodiments, a CD33 binding protein comprises a light chain variable domain, wherein the light chain CDR1 is SEQ ID NO:24; the light chain CDR2 is SEQ ID NO:31 and the light chain CDR3 is SEQ ID NO:38. In some embodiments, a CD33 binding protein comprises a light chain variable domain, wherein the light chain CDR1 is SEQ ID NO:25; the light chain CDR2 is SEQ ID NO:32 and the light chain CDR3 is SEQ ID NO:39. In some embodiments, a CD33 binding protein comprises a light chain variable domain, wherein the light chain CDR1 is SEQ ID NO:26; the light chain CDR2 is SEQ ID NO:33 and the light chain CDR3 is SEQ ID NO:40. In some embodiments, a CD33 binding protein comprises a light chain variable domain, wherein the light chain CDR1 is SEQ ID NO:27; the light chain CDR2 is SEQ ID NO:34 and the light chain CDR3 is SEQ ID NO:41.

Also provided herein in some embodiments, is a CD33 binding protein comprising a heavy chain variable domain, wherein the heavy chain CDR1 is SEQ ID NO:42; the heavy chain CDR2 is SEQ ID NO:49 and the heavy chain CDR3 is SEQ ID NO:56. In some embodiments, a CD33 binding protein comprises a heavy chain variable domain, wherein the heavy chain CDR1 is SEQ ID NO:43; the heavy chain CDR2 is SEQ ID NO:50 and the heavy chain CDR3 is SEQ ID NO:57. In some embodiments, a CD33 binding protein comprises a heavy chain variable domain, wherein the heavy chain CDR1 is SEQ ID NO:43; the heavy chain CDR2 is SEQ ID NO:50 and the heavy chain CDR3 is SEQ ID NO:58. In some embodiments, a CD33 binding protein comprises a heavy chain variable domain, wherein the heavy chain CDR1 is SEQ ID NO:43; the heavy chain CDR2 is SEQ ID NO:50 and the heavy chain CDR3 is SEQ ID NO:59. In some embodiments, a CD33 binding protein comprises a heavy chain variable domain, wherein the heavy chain CDR1 is SEQ ID NO:43; the heavy chain CDR2 is SEQ ID NO:50 and the heavy chain CDR3 is SEQ ID NO:60. In some embodiments, a CD33 binding protein comprises a heavy chain variable domain, wherein the heavy chain CDR1 is SEQ ID NO:44; the heavy chain CDR2 is SEQ ID NO:51 and the heavy chain CDR3 is SEQ ID NO:61. In some embodiments, a CD33 binding protein comprises a heavy chain variable domain, wherein the heavy chain CDR1 is SEQ ID NO:45; the heavy chain CDR2 is SEQ ID NO:52 and the heavy chain CDR3 is SEQ ID NO:62. In some embodiments, a CD33 binding protein comprises a heavy chain variable domain, wherein the heavy chain CDR1 is SEQ ID NO:46; the heavy chain CDR2 is SEQ ID NO:53 and the heavy chain CDR3 is SEQ ID NO:63. In some embodiments, a CD33 binding protein comprises a heavy chain variable domain, wherein the heavy chain CDR1 is SEQ ID NO:47; the heavy chain CDR2 is SEQ ID NO:54 and the heavy chain CDR3 is SEQ ID NO:63. In some embodiments, a CD33 binding protein comprises a heavy chain variable domain, wherein the heavy chain CDR1 is SEQ ID NO:48; the heavy chain CDR2 is SEQ ID NO:55 and the heavy chain CDR3 is SEQ ID NO:63.

In further embodiments, a CD33 binding protein comprises a variable light chain domain selected from amino acid sequences SEQ ID NOs.:1-10 shown in Table 3. In further embodiments, a CD33 binding protein comprises a variable heavy chain domain selected from amino acid sequences SEQ ID NO:11-20 shown in Table 4. In yet further embodiments, a CD33 binding protein comprises a variable light chain domain selected from amino acid sequences SEQ ID NOs.:1-10 shown in Table 3 and a variable heavy chain domain selected from amino acid sequences SEQ ID NO:11-20 shown in Table 4.

The term "binding protein" refers to an immunoglobulin derivative with antigen binding properties, i.e. immunoglobulin polypeptides or fragments thereof that contain an antigen binding site. The binding protein comprises variable domains of an antibody or fragments thereof. Each antigen-binding domain is formed by an antibody, i.e. immunoglobulin, variable heavy chain domain (VH) and an antibody variable light chain domain (VL) binding to the same epitope, whereas the variable heavy chain domain (VH) comprises three heavy chain complementarity determining regions (CDR): CDR1, CDR2 and CDR3; and the variable light chain domain (VL) comprises three light chain complementarity determining regions (CDR): CDR1, CDR2 and CDR3. In some instances, the binding protein according to some embodiments herein is devoid of immunoglobulin constant domains. In some instances, the variable light and heavy chain domains forming the antigen binding site is covalently linked with one another, e.g. by a peptide linker, or in other instances, the variable light and heavy chain domains non-covalently associate with one another to form the antigen binding site. The term "binding protein" refers also to antibody fragments or antibody derivatives including, for example, Fab, Fab', F(ab')$_2$, Fv fragments, single-chain Fv, tandem single-chain Fv ((scFv)$_2$, Bi-specific T-cell engagers (BiTE®), dual affinity retargeting antibodies (DART™), diabody and tandem diabody (TandAb®). Furthermore, in certain instances, the binding protein is multivalent, i.e. has two, three or more binding sites for CD33.

TABLE 1

Amino acid sequences of anti-CD33 variable light chain CDR1, CDR2 and CDR3

| CDR | Sequence identifier | Light Chain CDR Sequence |
|---|---|---|
| CDR1 | SEQ ID NO: 21 | GGNNIGSTTVH |
|  | SEQ ID NO: 22 | SGSRSNIGSNTVN |
|  | SEQ ID NO: 23 | SGSSSNIGSNTVN |
|  | SEQ ID NO: 24 | TGSSSNIGAGYDVH |
|  | SEQ ID NO: 25 | SGSSSNIGSNIVN |
|  | SEQ ID NO: 26 | SGSSSNIGSNTVK |
|  | SEQ ID NO: 27 | SGSSSNIGDNVVN |
| CDR2 | SEQ ID NO: 28 | DDNERPS |
|  | SEQ ID NO: 29 | GNNQRPS |
|  | SEQ ID NO: 30 | SDNQRPS |

TABLE 1-continued

Amino acid sequences of anti-CD33 variable light chain CDR1, CDR2 and CDR3

| CDR | Sequence identifier | Light Chain CDR Sequence |
|---|---|---|
| | SEQ ID NO: 31 | GNSNRPS |
| | SEQ ID NO: 32 | SNNQRPS |
| | SEQ ID NO: 33 | SNNQRSS |
| | SEQ ID NO: 34 | STNKRPS |
| CDR3 | SEQ ID NO: 35 | QVWDSGSDH |
| | SEQ ID NO: 36 | ATWDDSLIG |
| | SEQ ID NO: 37 | ATWDDSLNG |
| | SEQ ID NO: 38 | QSYDSSLSD |
| | SEQ ID NO: 39 | AAWDDSLKG |
| | SEQ ID NO: 40 | AAWDDSLNG |
| | SEQ ID NO: 41 | AAWDDSLSA |

TABLE 2

Amino acid sequences of anti-CD33 variable heavy chain CDR1, CDR2 and CDR3

| CDR | Sequence identifier | Heavy Chain CDR Sequence |
|---|---|---|
| CDR1 | SEQ ID NO: 42 | SNYGIH |
| | SEQ ID NO: 43 | TSYDIN |
| | SEQ ID NO: 44 | TSYYMH |
| | SEQ ID NO: 45 | TSYWIG |
| | SEQ ID NO: 46 | SSYAIS |
| | SEQ ID NO: 47 | SSYGIS |
| | SEQ ID NO: 48 | DSYAIS |
| CDR2 | SEQ ID NO: 49 | LISYDGNKKFYADSVKG |
| | SEQ ID NO: 50 | WMNPNSGNTGFAQKFQG |
| | SEQ ID NO: 51 | GIINPSGGSTSYAQKFQG |
| | SEQ ID NO: 52 | IIYPGDSDTRYSPSFQG |
| | SEQ ID NO: 53 | GIYPIFGSANYAQKFQG |
| | SEQ ID NO: 54 | GIIPIFGSAHYAQKFQG |
| | SEQ ID NO: 55 | GIIPIFGSAHYSQKFQG |
| CDR3 | SEQ ID NO: 56 | DRLESAAFDY |
| | SEQ ID NO: 57 | DRANTDFSYGMDV |
| | SEQ ID NO: 58 | DRAVTDYYYGMDV |
| | SEQ ID NO: 59 | DRANTDYSFGMDV |
| | SEQ ID NO: 60 | DRANTDYSLGMDV |
| | SEQ ID NO: 61 | DVVPAAIDYYGMDV |
| | SEQ ID NO: 62 | HKRGSDAPFDI |
| | SEQ ID NO: 63 | EYYYDSSEWAFDI |

TABLE 3

Amino acid sequences of all anti-CD33 variable light chain domains (amino acid sequences of variable light chain CDR1, CDR2 and CDR3 are in bold and underlined)

| anti-CD33 clone | Sequence identifier | Variable light chain (VL) domain Sequence |
|---|---|---|
| 01 | SEQ ID NO: 1 | WYELTQPPSVSVAPGQTAMITCGGNNIGSTTVHWYQQKPGQAPVLVVYDDNERPSGIPERFSGSNSGSTATLTINRVEAGDEADYYCQVWDSGSDHVVFGGGTKLTVL |
| 02 | SEQ ID NO: 2 | QSVLTQPPSASGTPGQRVTISCSGSRSNIGSNTVNWYQQLPGTAPKLLIYGNNQRPSGVPDRFSGSKSGTSASLAISGLQSEDEADYYCATWDDSLIGWVFGGGTKLTVL |
| 03 | SEQ ID NO: 3 | QSVLTQPPSASGTPGQRVTISCSGSRSNIGSNTVNWYQQLPGTAPKLLIYGNNQRPSGVPDRFSGSKSGTSASLAISGLQSEDEADYYCATWDDSLIGWVFGGGTKLTVL |
| 04 | SEQ ID NO: 4 | QSVLTQPPSASGTPGQRVTISCSGSRSNIGSNTVNWYQQLPGTAPKLLIYGNNQRPSGVPDRFSGSKSGTSASLAISGLQSEDEADYYCATWDDSLIGWVFGGGTKLTVL |
| 05 | SEQ ID NO: 5 | QSVLTQPPSASGTPGQRVTISCSGSRSNIGSNTVNWYQQLPGTAPKLLIYGNNQRPSGVPDRFSGSKSGTSASLAISGLQSEDEADYYCATWDDSLIGWVFGGGTKLTVL |
| 06 | SEQ ID NO: 6 | QSVLTQPPSASGTPGQRVTISCSGSSSNIGSNTVNWYQQLPGTAPKLLIYSDNQRPSGVPDRFSGSKSGSSASLAISGLQSDDEADYYCATWDDSLNGAVFGGGTKLTVL |
| 07 | SEQ ID NO: 7 | QSVLTQPPSVSGAPGQRVTISCTGSSSNIGAGYDVHWYQQLPGTAPKLLIYGNSNRPSGVPDRFSGSKSGTSASLAITGLQAEDEADYYCQSYDSSLSDVVFGGGTKLTVL |
| 08 | SEQ ID NO: 8 | QSVLTQPPSASGTPGQRVTISCSGSSSNIGSNIVNWYQQLPGTAPKLLIYSNNQRPSGVPDRFSGSKSGTSASLAISGLQSEDEADYYCAAWDDSLKGYVFGGGTKLTVL |
| 09 | SEQ ID NO: 9 | QSVLTQPPSASGTPGQRVTISCSGSSSNIGSNTVKWYQQLPGTAPKLLIYSNNQRSSGVPDRFSGSKSGSSASLAISGLQSEDEADYYCAAWDDSLNGYVFGGGTKLTVL |
| 10 | SEQ ID NO: 10 | QSVLTQPPSASGTPGQRVTISCSGSSSNIGDNVVNWYQQLPGTAPKLLIYSTNKRPSGVPDRFSGSKSGSSASLAISGLQSEDEADYYCAAWDDSLSAYVFGGGTKLTVL |

TABLE 4

Amino acid sequence of anti-CD33 variable heavy chain domain (amino acid sequences of variable heavy chain CDR1, CDR2 and CDR3 are in bold and underlined)

| anti-CD33 clone | Sequence identifier | Variable heavy chain (VH) domain Sequence |
|---|---|---|
| 01 | SEQ ID NO: 11 | QVQLQESGGGVVQPGRSLRLSCAASGFSFSNYGIHWVRQAPGKGLEWVALISYDGNKKFYADSVKGRFAISRDTSKNTVDLQMTSLRPEDTAVYYCAKDRLESAAFDYWGQGTLVTVSS |
| 02 | SEQ ID NO: 12 | QVQLVQSGAEVKKPGASVKVSCKASGYTFTSYDINWVRQAPGQGLEWMGWMNPNSGNTGFAQKFQGRVTMTRDTSTSTVYMELSSLRSEDTAVYYCARDRANTDFSYGMDVWGQGTLVTVSS |
| 03 | SEQ ID NO: 13 | QVQLVQSGAEVKKPGASVKVSCKASGYTFTSYDINWVRQAPGQGLEWMGWNMPNSGNTGFAQKFQGRVTMTRDTSTSTVYMELSSLRSEDTAVYYCARDRAVTDYYYGMDVWGQGTLVTVSS |
| 04 | SEQ ID NO: 14 | QVQLVQSGAEVKKPGASVKVSCKASGYTFTSYDINWVRQAPGQGLEWMGWNMPNSGNTGFAQKFQGRVTMTRDTSTSTVYMELSSLRSEDTAVYYCARDRANTDYSFGMDVWGQGTLVTVSS |
| 05 | SEQ ID NO: 15 | QVQLVQSGAEVKKPGASVKVSCKASGYTFTSYDINWVRQAPGQGLEWMGWMNPNSGNTGRAQKFQGRVTMTRDTSTSTVYMELSSLRSEDTAVYYCARDRANTDYSLGMDVWGQGTLVTVSS |
| 06 | SEQ ID NO: 16 | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARDVVPAAIDYYGMDVWGQGTTVTVSS |
| 07 | SEQ ID NO: 17 | QVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARHKRGSDAFDIWGQGTTVTVSS |
| 08 | SEQ ID NO: 18 | QVQLVQSGAEVKKPGSSVKVSCKASGGTFSSYAISWVRQAPGQGLEWMGGIYPIFGSANYAQKFQGRVTITADESTSTAYMELSSLRSEDTAVYYCAREYYYDSSEWAFDIWGQGTLVTVSS |
| 09 | SEQ ID NO: 19 | QVQLVQSGAEVKKPGSSVKVSCKASGGTFSSYGISWVRQAPGQGLEWMGGIIPIGFSAHYAQKFQGRVTITADESTSTAYMELSSLRSEDTAVYYCAREYYYDSSEWAFDIWGQGTLVTVSS |
| 10 | SEQ ID NO: 20 | QVQLVQSGAEVKKPGSSVKVSCKASGGTFDSYAISWVRQAPGQGLEWMGGIIPIFGSAHYSQKFQGRVTITADESTSTAYMELSSLRSEDTAVYYCAREYYYDSSEWAFDIWGQGTLVTVSS |

In some embodiments, a binding protein conferring specificity to CD33 is selected from one of the following combinations of a variable heavy chain domain and a variable light chain domain forming the human CD33 binding site shown in Table 3 and in Table 4. Non-limiting examples include (i) SEQ ID NO:1 and SEQ ID NO:11, (ii) SEQ ID NO:2 and SEQ ID NO:12, (iii) SEQ ID NO:3 and SEQ ID NO:13, (iv) SEQ ID NO:4 and SEQ ID NO:14, (v) SEQ ID NO:5 and SEQ ID NO:15, (vi) SEQ ID NO:6 and SEQ ID NO:16, (vii) SEQ ID NO:7 and SEQ ID NO:17, (viii) SEQ ID NO:8 and SEQ ID NO:18, (ix) SEQ ID NO:9 and SEQ ID NO:19, and (x) SEQ ID NO:10 and SEQ ID NO:20.

Also described herein are binding proteins that not only have specificity for CD33, but which also have at least one further functional domain. In a further embodiment at least one further functional domain is an effector domain. An "effector domain" comprises a binding site of an antibody specific for an effector cell, which can stimulate or trigger cytotoxicity, phagocytosis, antigen presentation, cytokine release. Such effector cells are, for example, but not limited to, T-cells. In particular, the effector domain comprises at least one antibody variable heavy chain domain and at least one variable light chain domain forming an antigen binding site for an antigen on T-cells, such as, for example, human CD3.

Thus, in some embodiments, the CD33 binding protein is multifunctional. The term multifunctional as used herein means that a binding protein exhibits two or more different biological functions. For example, the different biological functions are different specificities for different antigens. In certain instances, the multifunctional CD33 binding protein is multispecific, i.e. has binding specificity to CD33 and one or more further antigens. In certain instances, the binding protein is bispecific with specificities for CD33 and CD3. Such bispecific binding proteins include, for example, bispecific monoclonal antibodies of the classes IgA, IgD, IgE, IgG or IgM, diabodies, single-chain diabodies (scDb), tandem single chain FAT (scFv)2, for example Bi-specific T-cell engagers (BiTE®), dual affinity retargeting antibodies (DART™), tandem diabodies (TandAb®), and flexibodies.

In certain embodiments, the CD3 binding site of a bispecific CD33 and CD3 binding protein has specificity for human CD3 and, in some instances, cynomolgus CD3. Examples of such a binding site are polypeptides comprising the VH domain CDR1, CDR2 and CDR3 from the sequences shown in Table 5 (SEQ ID NOs:64-67) and VL domain CDR1, CDR2 and CDR3 from the sequence shown in Table 6 (SEQ ID NOs:68-71). In certain instances, a CD3 binding site is the combination of the variable heavy chain domain of SEQ ID NO:64 and the variable light chain domain of SEQ ID NO:68. In certain instances, a CD3 binding site is the combination of the variable heavy chain domain of SEQ ID NO:65 and the variable light chain domain of SEQ ID NO:69. In certain instances, a CD3 binding site is the combination of the variable heavy chain domain of SEQ ID NO:66 and the variable light chain domain of SEQ ID NO:70. In certain instances, a CD3 binding site is the combination of the variable heavy chain domain of SEQ ID NO:67 and the variable light chain domain of SEQ ID NO:71.

TABLE 5

Amino acid sequence of an anti-CD3 variable heavy chain domain (amino acid sequences of variable heavy chain CDR1, CDR2 and CDR3 are in bold and underlined)

| anti-CD3 | VH domain Sequence |
| --- | --- |
| SEQ ID NO: 64<br>CD3-01 | EVQLVESGGGLVQPGGSLRLSCAASGFTFSTYAMNWVRQAPGKGLEWVGRIRSKYNNYATYYADSVKDRFTISRDDSKNSLYLQMNSLKTEDTAVYYCARHGNFGSNYVSYFAYWGQGTLVTVSS |
| SEQ ID NO: 65<br>CD3-02 | EVQLVESGGGLVQPGGSLRLSCAASGFTFSTYAMNWVRQAPGKGLEWVGRIRSKYNNYATYYADSVKDRFTISRDDSKNSLYLQMNSLKTEDTAVYYCARHGNFGNSYVSWFAYWGQGTLVTVSS |
| SEQ ID NO: 66<br>CD3-03 | EVQLVESGGGLVQPGGSLRLSCAASGFTFSTYAMNWVRQAPGKGLEWVGRIRSKYNNYATYYADSVKDRFTISRDDSKNSLYLQMNSLKTEDTAVYYCARHGNFGNSYVSWFAYWGQGTLVTVSS |
| SEQ ID NO: 67<br>CD3-04 | EVQLVESGGGLVQPGGSLRLSCAASGFTFSTYAMNWVRQAPGKGLEWVGRIRSKYNNYATYYADSVKDRFTISRDDSKNSLYLQMNSLKTEDTAVYYCARHGNFGNSYVSWFAYWGQGTLVTVSS |

TABLE 6

Amino acid sequence of an anti-CD3 variable light chain domain (amino acid sequences of variable light chain CDR1, CDR2 and CDR3 are in bold and underlined)

| anti-CD3 | VL domain Sequence |
| --- | --- |
| SEQ ID NO: 68<br>CD3-01 | DIQMTQSPSSLSASVGDRVTITCRSSTGAVTTSNYANWVQQKPGKAPKALIGGTNKRAPGVPSRFSGSLIGDKATLTISSLQPEDFATYYCALWYSNLWVFGQGTKVEIK |
| SEQ ID NO: 69<br>CD3-02 | DIQMTQSPSSLSASVGDRVTITCRSSTGAVTTSNYANWVQQKPGKAPKGLIGGTNKRAPGVPARFSGSGSGTDFTLTISSLQPEDFATYYCALWYSNLWVFGQGTKVEIK |
| SEQ ID NO: 70<br>CD3-03 | DIQMTQSPSSLSASVGDRVTITCRSSTGAVTTSNYANWVQQKPGKAPKGLIGGTNKRAPGVPSRFSGSLIGDKATLTISSLQPEDFATYYCALWYSNLWVFGQGTKVEIK |
| SEQ ID NO: 71<br>CD3-04 | DIQMTQSPSSLSASVGDRVTITCRSSTGAVTTSNYANWVQQKPGKAPKGLIGGTNKRAPEVPSRFSGSLIGTDFTLTISSLQPEDFATYYCALWYSNLWVFGQGTKVEIK |

In further embodiments, the CD3 binding site of a bispecific CD33 and CD3 binding protein has a variable heavy chain domain comprising a CDR1 sequence of STYAMN (SEQ ID NO:72). In further embodiments, the CD3 binding site of a bispecific CD33 and CD3 binding protein has a variable heavy chain domain comprising a CDR2 sequence of RIRSKYNNYATYYADSVKD (SEQ ID NO:73). In further embodiments, the CD3 binding site of a bispecific CD33 and CD3 binding protein has a variable heavy chain domain comprising a CDR3 sequence of HGNFGNSYVSWFAY (SEQ ID NO:74). In further embodiments, the CD3 binding site of a bispecific CD33 and CD3 binding protein has a variable heavy chain domain comprising a CDR3 sequence of HGNFGNSYVSYFAY (SEQ ID NO:75). In yet further embodiments, the CD3 binding site has a variable heavy chain domain comprising a CDR1, CDR2 and CDR3 sequence of SEQ ID NOs:72-74 respectively. In yet further embodiments, the CD3 binding site has a variable heavy chain domain comprising a CDR1, CDR2 and CDR3 sequence of SEQ ID NOs:72, 73 and 75 respectively.

In further embodiments, the CD3 binding site of a bispecific CD33 and CD3 binding protein has a variable heavy chain domain comprising a CDR1 sequence selected from the group consisting of NTYAMN (SEQ ID NO:76), NTYAMH (SEQ ID NO:77) and NKYAMN (SEQ ID NO:78). In further embodiments, the CD3 binding site of a bispecific CD33 and CD3 binding protein has a variable heavy chain domain comprising a CDR2 sequence selected from the group consisting of RIRNKYNNYATYYADSVKD (SEQ ID NO:79), RIRNKYNNYATEYADSVKD (SEQ ID NO:80), RIRNKYNNYATEYAASVKD (SEQ ID NO:81), RIRNKYNNYATEYAASVKD (SEQ ID NO:82), RIRSKYNNYATYYADSVKG (SEQ ID NO:83) and RIRSKYNNYATEYADSVKS (SEQ ID NO:84). In further embodiments, the CD3 binding site of a bispecific CD33 and CD3 binding protein has a variable heavy chain domain comprising a CDR3 sequence selected from the group consisting of HGNFGDSYVSWFAY (SEQ ID NO:85), HGNFGNTYVSWFAY (SEQ ID NO:86), HGNFGCSYVSWFAY (SEQ ID NO:87), HGNFGNSYISYWAY (SEQ ID NO:88) and HGNFGNSYVSFFAY (SEQ ID NO:89).)

In yet further embodiments, the CD3 binding site has a variable heavy chain domain comprising a CDR1, CDR2 and CDR3 sequence of SEQ ID NOs:76, 73 and 74 respectively, SEQ ID NOs:76, 79 and 74 respectively, SEQ ID NOs:76, 80 and 74 respectively, SEQ ID NOs:76, 81 and 74 respectively, SEQ ID NOs:76, 82 and 74 respectively, SEQ ID NOs:72, 83 and 74 respectively, SEQ ID NOs:72, 83 and 85 respectively, SEQ ID NOs:76, 83 and 86 respectively, SEQ ID NOs:77, 83 and 74 respectively, SEQ ID NOs:72, 83 and 87 respectively, SEQ ID NOs:78, 73 and 88 respectively or SEQ ID NOs:78, 84 and 89 respectively.

In further embodiments, the CD3 binding site of a bispecific CD33 and CD3 binding protein has a variable light chain domain comprising a CDR1 sequence of RSSTGAVTTSNYAN (SEQ ID NO:90). In further embodiments, the CD3 binding site of a bispecific CD33 and CD3 binding protein has a variable light chain domain comprising a CDR2 sequence of GTNKRAP (SEQ ID NO:91). In further embodiments, the CD3 binding site of a bispecific CD33 and CD3 binding protein has a variable light chain domain comprising a CDR3 sequence of ALWYSNL (SEQ ID NO:92). In yet further embodiments, the CD3 binding site has a variable light chain domain comprising a CDR1, CD2 and CD3 sequence of SEQ ID NOs:90-92 respectively.

In certain instances, the CD3 binding site has a high affinity to CD3. Alternatively, in other instances, the CDR1, CDR2, CDR3 from the heavy-chain domain as well as the light-chain domain or, optionally, the variable light-chain domains and variable heavy-chain domains is derived from other CD3 antibodies, such as, for example UCHT1, muromonab-CD3 (OKT3), otelixizumab (TRX4), teplizumab (MGA031), visilizumab (Nuvion), and the like.

In another aspect, described herein are CD33 binding proteins as well as the bispecific CD33 and CD3 binding proteins that are humanized or fully human, i.e. of human origin.

In some embodiments, a bispecific CD33 and CD3 binding protein has one of the following combinations providing CD33 and CD3 specificity by variable light and heavy chain domains for CD33 and CD3: include, but are not limited to, (i) SEQ ID NOs:2, 12, 65 and 69, (ii) SEQ ID NOs:3, 13, 65 and 69, (iii) SEQ ID NOs:4, 14, 65 and 69, (iv) SEQ ID NOs:5, 15, 65 and 69, (v) SEQ ID NOs:1, 11, 64 and 68, (vi) SEQ ID NOs:2, 12, 64 and 68, (vii) SEQ ID NOs:2, 12, 66 and 70, (viii) SEQ ID NOs:4, 14, 66 and 70, (ix) SEQ ID NOs:5, 15, 66 and 70, and (x) SEQ ID NOs:3, 13, 64 and 68, (xi) SEQ ID NOs:3, 13, 67 and 71, (xii) SEQ ID NOs:4, 14, 64 and 68, (xiii) SEQ ID NOs:5, 15, 64 and 68, (xiv) SEQ ID NOs:7, 17, 64 and 68, (xv) SEQ ID NOs:6, 16, 64 and 68, (xvi) SEQ ID NOs:6, 16, 67 and 71, (xvii) SEQ ID NOs:8, 18, 64 and 68, (xviii) SEQ ID NOs:9, 19, 64 and 68; (xix) SEQ ID NOs:9, 19, 67 and 71, and (xx) SEQ ID NOs:10, 20, 64 and 68.

Conserved Variants of CDR Sequences and Heavy and Light Chain Domains

In alternative embodiments, the heavy and light chain domains incorporate immunologically active homologues or variants of the CDR sequences described herein. Accordingly in some embodiments, a CDR sequence in a heavy or light chain domain that binds to CD33 or CD3 is similar to, but not identical to, the amino acid sequence depicted in SEQ ID NOs: 21-63 or 72-92. In certain instances, a CDR variant sequence has a sequence identity of 99%, 98%, 97%, 96%, 95%, 94%, 93%, 92%, 91%, 90%, 89%, 88%, 87%, 86%, 85%, 84%, 83%, 82%, 81%, or 80% compared to the sequence of SEQ ID NOs: 21-63 or 72-90 and which is immunologically active.

In further instances, a CDR variant sequence incorporates 1, 2, 3, 4, or 5 conserved amino acid substitutions. Conservative substitutions include amino acid substitutions that substitute a given amino acid with another amino acid of similar characteristics and further include, among the aliphatic amino acids interchange of alanine, valine, leucine, and isoleucine; interchange of the hydroxyl residues serine and threonine, exchange of the acidic residues aspartate and glutamate, substitution between the amide residues asparagine and glutamine, exchange of the basic residues lysine and arginine, and replacements among the aromatic residues phenylalanine and tyrosine.

In yet further instances, a CDR variant sequence incorporates substitutions that enhance properties of the CDR such as increase in stability, resistance to proteases and/or binding affinities to CD33 or CD3.

In other instances, a CDR variant sequence is modified to change non-critical residues or residues in non-critical regions. Amino acids that are not critical can be identified by known methods, such as affinity maturation, CDR walking, site-directed mutagenesis, crystallization, nuclear magnetic resonance, photoaffinity labeling, or alanine-scanning mutagenesis.

In further alternative embodiments, the CD33 and CD3 binding proteins comprise heavy and light chain domains that are immunologically active homologues or variants of heavy and light chain domain sequences provided herein. Accordingly, in some embodiments, a CD33 and CD3 binding protein comprises a heavy or light chain domain sequence that is similar to, but not identical to, the amino acid sequence depicted in SEQ ID NOs:1-20 or 64-71. In certain instances, a variant heavy or light chain domain sequence has a sequence identity of 99%, 98%, 97%, 96%, 95%, 94%, 93%, 92%, 91%, 90%, 89%, 88%, 87%, 86%, 85%, 84%, 83%, 82%, 81%, or 80% compared to the sequence of SEQ ID NOs:1-20 or 64-71 and which is immunologically active.

In further instances, a variant heavy or light chain domain sequence incorporates 1, 2, 3, 4, or 5 conserved amino acid substitutions. Conservative substitutions include amino acid substitutions that substitute a given amino acid with another amino acid of similar characteristics and further include, among the aliphatic amino acids interchange of alanine, valine, leucine, and isoleucine; interchange of the hydroxyl residues serine and threonine, exchange of the acidic residues aspartate and glutamate, substitution between the amide residues asparagine and glutamine, exchange of the basic residues lysine and arginine, and replacements among the aromatic residues phenylalanine and tyrosine.

In yet further instances, a variant heavy or light chain domain sequence incorporates substitutions that enhance properties of the CDR such as increase in stability, resistance to proteases and/or binding affinities to CD33 or CD3.

In other instances, a variant heavy or light chain domain sequence is modified to change non-critical residues or residues in non-critical regions. Amino acids that are not critical can be identified by known methods, such as affinity maturation, CDR walking, site-directed mutagenesis, crystallization, nuclear magnetic resonance, photoaffinity labeling, or alanine-scanning mutagenesis.

CD33 and CD3 Bispecific and Tandem Diabodies

In another aspect, a CD33 binding protein or the bispecific CD33 and CD3 binding protein is a dimer, i.e. comprises two polypeptides with antigen binding sites for CD33 and CD3.

Also provided herein in another aspect, is a dimeric and bispecific CD33 and CD3 binding protein in the format of a tandem diabody (TandAb®). Such tandem diabodies are constructed by linking four antibody variable binding domains (two heavy-chain variable domains (VH) and two light-chain variable domains (VL) in a single gene construct (FIG. 1) enabling homo-dimerization. In such tandem diabodies the linker length is such that it prevents intramolecular pairing of the variable domains so that the molecule cannot fold back upon itself to form a single-chain diabody, but rather is forced to pair with the complementary domains of another chain. The domains are also arranged such that the corresponding VH and VL domains pair during this dimerization. Following expression from a single gene construct, two identical polypeptide chains fold head-to-tail forming a functional non-covalent homodimer of approximately 105 kDa (FIG. 1). Despite the absence of intermolecular covalent bonds, the homodimer is highly stable once formed, remains intact and does not revert back to the monomeric form.

Tandem diabodies have a number of properties that provide advantages over traditional monoclonal antibodies and other smaller bispecific molecules. Tandem diabodies contain only antibody variable domains and therefore are contemplated to lack side effects or non-specific interactions that may be associated with an Fc moiety. For example, Fc receptors which can bind to Fc domains are found on numerous cell types such as white blood cells (e.g., basophils, B-cells, eosinophils, natural killer cells, neutrophils and the like) or Kuppfer cells. Because tandem diabodies allow for bivalent binding to each of CD33 and CD3, the avidity is the same as that of an IgG. The size of a tandem diabody, at approximately 105 kDa, is smaller than that of an IgG, which may allow for enhanced tumor penetration. However, this size is well above the renal threshold for first-pass clearance, offering a pharmacokinetic advantage compared with smaller bispecific formats based on antibody-binding domains or non-antibody scaffolds. Moreover tandem diabodies are advantageous over other bispecific binding proteins such as BiTE or DART molecules based on this pharmacokinetic and avidity properties resulting in longer intrinsic half-lives and rapid cytotoxicity. Tandem diabodies are well expressed in host cells, for example, mammalian CHO cells. It is contemplated that robust upstream and downstream manufacturing process is available for tandem diabodies.

Figure 2:
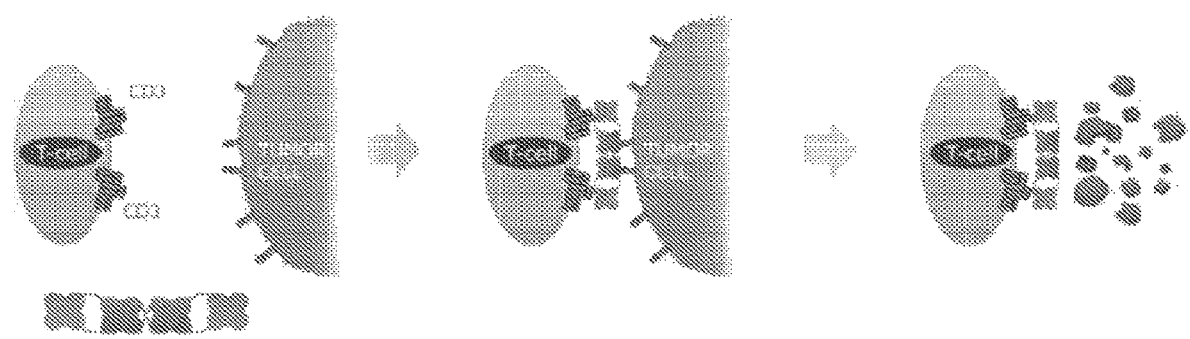
FIG. 2 CD3 engaging tandem diabody and its mode of action. Tandem diabodies are tetravalent bispecific proteins that can engage cytotoxic T-cells via binding to CD3. The tandem diabody binds to a CD33$^+$ tumor cell with two of four binding domains and to CD3 with the other two binding domains. This T-cell/target cell binding (crosslinking) event promotes activation of the T-cell and promotes the subsequent destruction of the tumor cell via ADCC.

The CD33 and CD3 bispecific tandem diabodies described herein are designed to allow specific targeting of CD33$^+$ tumor cells by recruiting cytotoxic T-cells. This improves ADCC (antibody dependent cell-mediated cytotoxicity) as compared to full length antibodies directed to a sole antigen and are not capable of directly recruiting cytotoxic T-cells. In contrast, by engaging CD3 molecules expressed specifically on these cells, the tandem diabody can crosslink cytotoxic T-cells with CD33$^+$ tumor cells in a highly specific fashion, thereby significantly increasing the cytotoxic potential of such molecules. This mechanism is outlined in FIG. 2. The tandem diabody displays strong, specific and efficient ADCC. It is reported that T-cells can play a role in controlling tumor growth. For example, the presence of cytotoxic T-cells in colorectal tumors as well as lymph nodes from NHL patients was shown to correlate with a better clinical outcome. Furthermore, the potential of therapies designed to induce T-cell responses has been demonstrated for melanoma vaccines, as well as the antibody directed against CTLA-4, a negative regulator of T-cell activation. The tandem diabodies described herein engage cytotoxic T-cells via binding to the surface-expressed CD3, which forms part of the T-cell receptor. Simultaneous binding of this tandem diabody to CD3 and to CD33 expressed on the surface of particular tumor cells causes T-cell activation and mediates the subsequent lysis of the tumor cell (FIG. 2).

Therefore, in a further aspect is a multispecific, tandem diabody. In some embodiments, a multispecific tandem diabody has specificities to two, three or more different epitopes, wherein two or more epitopes can be of the same antigen target or of different antigen targets. In certain embodiments the multispecific, tandem diabody is bispecific and tetravalent, i.e. comprises four antigen-binding sites. Such a bispecific tandem diabody binds with at least one antigen-binding site, to human CD3 and to human CD33, wherein in certain instances, the tandem diabody binds with two antigen-binding sites to human CD3 and with two other antigen-binding sites to human CD33, i.e. the tandem diabody binds bivalently to each antigen.

In some embodiments, a bispecific, antigen-binding tandem diabody is specific to human CD33 and human CD3, wherein said tandem diabody comprises a first polypeptide and a second polypeptide, each polypeptide having at least four variable chain domains linked one after another, wherein each polypeptide comprises
(i) a variable heavy chain (VH) domain specific to human CD33;
(ii) a variable light chain (VL) domain specific to human CD33;
(iii) a VH domain specific for human CD3, and
(iv) a VL domain specific for human CD3.

In particular embodiments, a bispecific tandem diabody specifically binds to an epitope of human CD33 which is within $_{62}$DQEVQEETQ$_{70}$ (SEQ ID NO:94) (amino acid residues 62-70 of SEQ ID NO:93) of human CD33. In particular instances, such a tandem diabody comprises a first polypeptide and a second polypeptide, each polypeptide having at least four variable chain domains linked one after another, wherein each polypeptide comprises
(i) a variable heavy chain domain specific to an epitope of human CD33 which is within $_{62}$DQEVQEETQ$_{70}$ (SEQ ID NO:94) (amino acid residues 62-70 of SEQ ID NO:93) of human CD33;

(ii) a variable light chain domain specific to an epitope of human CD33 which is within $_{62}$DQEVQEETQ$_{70}$ (SEQ ID NO:94) (amino acid residues 62-70 of SEQ ID NO:93) of human CD33;
(iii) a variable heavy chain domain specific for human CD3, and
(iv) a variable light chain domain specific for human CD3.

In other embodiments, described herein are CD33/CD3 tandem diabodies that have an affinity to CD33 on CD33$^+$ cells with a K$_D$ of 10 nM or less, 5 nM or less, 1 nM or less, or 0.5 nM or less. The CD33$^+$ cells can be selected from tumor cells such as, for example, HL-60 or KG-1.

In a further embodiment a CD33/CD3 tandem diabody described herein binds CD3 and in certain instances, the epsilon chain of CD3 on CD3$^+$ cells, particularly T-cells, with a K$_D$ of 10 nM or less, 5 nM or less or 2 nM or less.

In some embodiments, each polypeptide of a bispecific tandem diabody comprises one of the following combinations of the four variable chain domains: (i) SEQ ID NOs:2, 12, 65 and 69, (ii) SEQ ID NOs:3, 13, 65 and 69, (iii) SEQ ID NOs:4, 14, 65 and 69, (iv) SEQ ID NOs:5, 15, 65 and 69, (v) SEQ ID NOs:1, 11, 64 and 68, (vi) SEQ ID NOs:2, 12, 64 and 68, (vii) SEQ ID NOs:2, 12, 66 and 70, (viii) SEQ ID NOs:4, 14, 66 and 70, (ix) SEQ ID NOs:5, 15, 66 and 70, and (x) SEQ ID NOs:3, 13, 64 and 68, (xi) SEQ ID NOs:3, 13, 67 and 71, (xii) SEQ ID NOs:4, 14, 64 and 68, (xiii) SEQ ID NOs:5, 15, 64 and 68, (xiv) SEQ ID NOs:7, 17, 64 and 68, (xv) SEQ ID NOs:6, 16, 64 and 68, (xvi) SEQ ID NOs:6, 16, 67 and 71, (xvii) SEQ ID NOs:8, 18, 64 and 68, (xviii) SEQ ID NOs:9, 19, 64 and 68; (xix) SEQ ID NOs:9, 19, 67 and 71, and (xx) SEQ ID NOs:10, 20, 64 and 68.

As used herein, "dimer" refers to a complex of two polypeptides. In certain embodiments, the two polypeptides are non-covalently associated with each other, in particular with the proviso that there is no covalent bond between the two polypeptides. In certain instances, the two polypeptides have covalent associations such as disulfide bonds that form to aid in stabilization of the dimer. In certain embodiments, the dimer is homodimeric, i.e. comprises two identical polypeptides. The term "polypeptide" refers to a polymer of amino acid residues linked by amide bonds. The polypeptide is, in certain instances, a single chain fusion protein, which is not branched. In the polypeptide the variable antibody domains are linked one after another. The polypeptide, in other instances, may have contiguous amino acid residues in addition to the variable domain N-terminal and/or C-terminal residues. For example, such contiguous amino acid residues may comprise a Tag sequence, in some instances at the C-terminus, which is contemplated to be useful for the purification and detection of the polypeptide.

In one aspect, each polypeptide of the bispecific tandem diabody comprises four variable domains, a variable light chain (VL) and a variable heavy chain (VH) of a CD3 binding protein as well as a variable light chain (VL) and a variable heavy chain (VH) of a CD33 binding protein. In certain embodiments, four variable domains are linked by peptide linkers L1, L2 and L3 and in some instances arranged from the N- to the C-terminus as follows:
Domain Order:
(1) VL(CD3)-L1-VH(CD33)-L2-VL(CD33)-L3-VH(CD3); or
(2) VH(CD3)-L1-VL(CD33)-L2-VH(CD33)-L3-VL(CD3); or
(3) VL(CD33)-L1-VH(CD3)-L2-VL(CD3)-L3-VH(CD33); or
(4) VH(CD33)-L1-VL(CD3)-L2-VH(CD3)-L3-VL(CD33).

The length of the linkers influences the flexibility of the antigen-binding tandem diabody according to reported studies. Accordingly, in some embodiments, the length of the peptide linkers L1, L2 and L3 is such that the domains of one polypeptide can associate intermolecularly with the domains of another polypeptide to form the dimeric antigen-binding tandem diabody. In certain embodiments, such linkers are "short", i.e. consist of 0, 1, 2, 3, 4, 5, 6, 7, 8, 9, 10, 11 or 12 amino acid residues. Thus, in certain instances, the linkers consist of about 12 or less amino acid residues. In the case of 0 amino acid residues, the linker is a peptide bond. Such short linkers favor the intermolecular dimerization of the two polypeptides by binding and forming correct antigen-binding sites between antibody variable light chain domains and antibody variable heavy chain domains of different polypeptides. Shortening the linker to about 12 or less amino acid residues generally prevents adjacent domains of the same polypeptide chain from intramolecular interaction with each other. In some embodiments, these linkers consist of about 3 to about 10, for example 4, 5 or 6 contiguous amino acid residues.

Regarding the amino acid composition of the linkers, peptides are selected that do not interfere with the dimerization of the two polypeptides. For example, linkers comprising glycine and serine residues generally provide protease resistance. The amino acid sequence of the linkers can be optimized, for example, by phage-display methods to improve the antigen binding and production yield of the antigen-binding polypeptide dimer. Examples of peptide linkers suitable for a tandem diabody in some embodiments are GGSGGS (SEQ ID NO:95), GGSG (SEQ ID NO:96), or GGSGG (SEQ ID NO:97).

Non-limiting examples of tandem diabodies as described herein are tandem diabodies having an anti-CD33 VL and VH domain, an anti-CD3 VL and VH domain, domain order and linker according to Table 7.

TABLE 7

Exemplary CD33/CD3 Tandem Diabodies (TandAbs)

| Tandem Diabody | Anti-CD33 domain VL | Anti-CD33 domain VH | Anti-CD3 domain VH | Anti-CD3 domain VL | Domain Order | Linker L1/L3 | Linker L2 |
|---|---|---|---|---|---|---|---|
| 01 | SEQ ID NO: 2 | SEQ ID NO: 12 | SEQ ID NO: 65 | SEQ ID NO: 69 | 1 | GGSGGS | GGSG |
| 02 | SEQ ID NO: 3 | SEQ ID NO: 13 | SEQ ID NO: 65 | SEQ ID NO: 69 | 1 | GGSGGS | GGSG |
| 03 | SEQ ID NO: 4 | SEQ ID NO: 14 | SEQ ID NO: 65 | SEQ ID NO: 69 | 1 | GGSGGS | GGSG |
| 04 | SEQ ID NO: 5 | SEQ ID NO: 15 | SEQ ID NO: 65 | SEQ ID NO: 69 | 1 | GGSGGS | GGSG |
| 05 | SEQ ID NO: 4 | SEQ ID NO: 14 | SEQ ID NO: 65 | SEQ ID NO: 69 | 1 | GGSGGS | GGSGG |
| 06 | SEQ ID NO: 5 | SEQ ID NO: 15 | SEQ ID NO: 65 | SEQ ID NO: 69 | 1 | GGSGGS | GGSGG |
| 07 | SEQ ID NO: 1 | SEQ ID NO: 11 | SEQ ID NO: 64 | SEQ ID NO: 68 | 1 | GGSGGS | GGSGGS |
| 08 | SEQ ID NO: 2 | SEQ ID NO: 12 | SEQ ID NO: 64 | SEQ ID NO: 68 | 3 | GGSGGS | GGSGGS |
| 09 | SEQ ID NO: 2 | SEQ ID NO: 12 | SEQ ID NO: 66 | SEQ ID NO: 70 | 1 | GGSGGS | GGSG |
| 10 | SEQ ID NO: 4 | SEQ ID NO: 14 | SEQ ID NO: 66 | SEQ ID NO: 70 | 1 | GGSGGS | GGSG |
| 11 | SEQ ID NO: 5 | SEQ ID NO: 15 | SEQ ID NO: 66 | SEQ ID NO: 70 | 1 | GGSGGS | GGSG |
| 12 | SEQ ID NO: 3 | SEQ ID NO: 13 | SEQ ID NO: 64 | SEQ ID NO: 68 | 1 | GGSGGS | GGSG |
| 13 | SEQ ID NO: 3 | SEQ ID NO: 13 | SEQ ID NO: 67 | SEQ ID NO: 71 | 1 | GGSGGS | GGSG |
| 14 | SEQ ID NO: 2 | SEQ ID NO: 12 | SEQ ID NO: 64 | SEQ ID NO: 68 | 1 | GGSGGS | GGSG |
| 15 | SEQ ID NO: 4 | SEQ ID NO: 14 | SEQ ID NO: 64 | SEQ ID NO: 68 | 1 | GGSGGS | GGSG |
| 16 | SEQ ID NO: 5 | SEQ ID NO: 15 | SEQ ID NO: 64 | SEQ ID NO: 68 | 1 | GGSGGS | GGSG |
| 17 | SEQ ID NO: 7 | SEQ ID NO: 17 | SEQ ID NO: 64 | SEQ ID NO: 68 | 1 | GGSGGS | GGSG |
| 18 | SEQ ID NO: 7 | SEQ ID NO: 17 | SEQ ID NO: 64 | SEQ ID NO: 68 | 2 | GGSGGS | GGSG |
| 19 | SEQ ID NO: 6 | SEQ ID NO: 16 | SEQ ID NO: 64 | SEQ ID NO: 68 | 1 | GGSGGS | GGSG |
| 20 | SEQ ID NO: 6 | SEQ ID NO: 16 | SEQ ID NO: 67 | SEQ ID NO: 71 | 1 | GGSGGS | GGSG |
| 21 | SEQ ID NO: 8 | SEQ ID NO: 18 | SEQ ID NO: 64 | SEQ ID NO: 68 | 1 | GGSGGS | GGSG |
| 22 | SEQ ID NO: 9 | SEQ ID NO: 19 | SEQ ID NO: 64 | SEQ ID NO: 68 | 1 | GGSGGS | GGSG |
| 23 | SEQ ID NO: 9 | SEQ ID NO: 19 | SEQ ID NO: 67 | SEQ ID NO: 71 | 1 | GGSGGS | GGSG |
| 24 | SEQ ID NO: 10 | SEQ ID NO: 20 | SEQ ID NO: 64 | SEQ ID NO: 68 | 1 | GGSGGS | GGSG |

In some embodiments, a tandem diabody is attached to a C-terminal hexa-histidine (6×His)-tag. In some embodiments, a tandem diabody with a C-terminal hexa-histidine (6×His)-tag is tandem diabody 01 (SEQ ID NO:98), 02 (SEQ ID NO:99), 03 (SEQ ID NO:100), 04 (SEQ ID NO:101), 05 (SEQ ID NO:102), 06 (SEQ ID NO:103), 07 (SEQ ID NO:104), 08 (SEQ ID NO:105), 09 (SEQ ID NO:106), 10 (SEQ ID NO:107), 11 (SEQ ID NO:108), 12 (SEQ ID NO:109), 13 (SEQ ID NO:110), 14 (SEQ ID NO:111), 15 (SEQ ID NO:112), 16 (SEQ ID NO:113), 17 (SEQ ID NO:114), 18 (SEQ ID NO:115), 19 (SEQ ID NO:116), 20 (SEQ ID NO:117), 21 (SEQ ID NO:118), 22 (SEQ ID NO:119), 23 (SEQ ID NO:120), or 24 (SEQ ID NO:121) as depicted in FIG. 10A to 10X.

In some embodiments, a tandem diabody is tandem diabody 01 (SEQ ID NO:123), 02 (SEQ ID NO:124), 03 (SEQ ID NO:125), 04 (SEQ ID NO:126), 05 (SEQ ID NO:127), 06 (SEQ ID NO:128), 07 (SEQ ID NO:129), 08 (SEQ ID NO:130), 09 (SEQ ID NO:131), 10 (SEQ ID NO:132), 11 (SEQ ID NO:133), 12 (SEQ ID NO:134), 13 (SEQ ID NO:135), 14 (SEQ ID NO:136), 15 (SEQ ID NO:137), 16 (SEQ ID NO:138), 17 (SEQ ID NO:139), 18 (SEQ ID NO:140), 19 (SEQ ID NO:141), 20 (SEQ ID NO:142), 21 (SEQ ID NO:143), 22 (SEQ ID NO:144), 23 (SEQ ID NO:145), or 24 (SEQ ID NO:146) as depicted in FIG. 11A to 11X.

The CD33 binding protein and the CD33/CD3 bispecific binding protein (e.g., CD33/CD3 bispecific tandem diabody) described herein is produced, in some embodiments, by expressing polynucleotides encoding the polypeptide of the tandem diabody which associates with another identical polypeptide to form the antigen-binding tandem diabody. Therefore, another aspect is a polynucleotide, e.g. DNA or RNA, encoding the polypeptide of an antigen-binding tandem diabody as described herein.

The polynucleotide is constructed by known methods such as by combining the genes encoding at least four antibody variable domains either separated by peptide linkers or, in other embodiments, directly linked by a peptide bond, into a single genetic construct operably linked to a suitable promoter, and optionally a suitable transcription terminator, and expressing it in bacteria or other appropriate expression system such as, for example CHO cells. Depending on the vector system and host utilized, any number of suitable transcription and translation elements, including constitutive and inducible promoters, may be used. The promoter is selected such that it drives the expression of the polynucleotide in the respective host cell.

In some embodiments, the polynucleotide is inserted into a vector, preferably an expression vector, which represents a further embodiment. This recombinant vector can be constructed according to known methods.

A variety of expression vector/host systems may be utilized to contain and express the polynucleotide encoding the polypeptide of the described antigen-binding tandem diabody. Examples of expression vectors for expression in *E. coli* are pSKK (Le Gall et al., J Immunol Methods. (2004) 285(1):111-27) or pcDNA5 (Invitrogen) for expression in mammalian cells.

Thus, the antigen-binding tandem diabody as described herein, in some embodiments, is produced by introducing a vector encoding the polypeptide as described above into a host cell and culturing said host cell under conditions whereby the polypeptide chains are expressed, may be isolated and, optionally, further purified.

In other aspects, the CD33 binding protein or the CD33/CD3 bispecific binding protein (e.g., CD33/CD3 bispecific tandem diabody) described herein has a modification. Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, drug conjugation, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. In further embodiments, the CD33 binding protein or the CD33/CD3 bispecific binding protein is modified with additional amino acids, such as a leader or secretory sequence or a sequence for purification of the polypeptide.

In other aspects, provided herein are pharmaceutical compositions comprising the CD33 binding protein, an antigen-binding tandem diabody, a vector comprising the polynucleotide encoding the polypeptide of the antigen binding tandem diabody or a host cell transformed by this vector and at least one pharmaceutically acceptable carrier. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

Bispecific CD33/CD3 binding proteins with high-affinity binding to CD33 and CD3 are highly active in a large number of primary AML specimens, suggesting that these molecules could be active against human AML across the entire cytogenetic/molecular disease spectrum, even in cases of minimal CD33 expression. Of note, drug-specific cytotoxicity is also observed in the presence of residual autologous T-cells and is significantly augmented by the addition of controlled amounts of healthy donor T-cells (see Example 6).

The CD33/CD3 bispecific binding proteins, in particular tandem diabodies, can induce potent cytolysis of CD33$^+$ leukemic cells in vitro. The data indicate that high-affinity binding to both CD33 and CD3 maximizes bispecific protein-induced T-cell activation and anti-AML efficacy. High-affinity CD33/CD3-directed bispecific binding proteins, such as the tandem diabodies described herein display cytolytic activity in primary AML in vitro. Thus, these bispecific binding proteins and tandem diabodies are suitable for a therapeutic approach for the treatment of acute myeloid leukemia (AML) or other hematologic malignancies, for example, myeloid dysplastic syndrome (MDS) or myeloproliferative disease (MPD).

Therefore, provided herein are methods wherein the antigen-binding tandem diabody as described herein above is administered in an effective dose to a subject, e.g., a patient, for the treatment of a CD33+ cancer (e.g. acute myeloid leukemia (AML)), disease or condition. CD33+ cancers include, but are not limited to, acute leukemias such as acute myeloid leukemia, acute lymphoblastic leukemia (ALL) including precursor B-cell lymphoblastic leukemia, myeloid sarcoma, multiple myeloma, acute lymphomas such as acute lymphoblastic lymphoma, chronic myelomonocytic leukemia and the like. CD33+ diseases and conditions include immune suppressive states or environments attributed by myeloid derived suppressor cells (MDSCs) in certain cancers and chronic inflammation.

In some embodiments, the antigen-binding tandem diabody as described herein is administered for the treatment of acute myeloid leukemia (AML). In certain embodiments, the antigen-binding tandem diabody as described herein is administered for the treatment of an acute myeloid leukemia subtype.

The French-American-British classification system divides AML into eight subtypes: AML-M0 (minimally differentiated), AML-M1 (without maturation), AML-M2 (with granulocytic maturation), AML-M3 (promyelocytic or acute promyelocytic leukemia), AML-4 (acute myelomonocytic leukemia), AML-M5 (acute monoblastic or monocytic leukemia), AML-M6 (acute erythroid leukemia), and AML-M7 (acute megakaryoblastic leukemia). In certain instances, the antigen-binding tandem diabody as described herein is administered for the treatment of AML-M0, AML-M1, AML-M2, AML-M3, AML-M4, AML-M5, AML-M6, or AML-M7.

The WHO AML classification scheme organizes AML according to the following subtypes: AML with Recurrent Genetic Abnormalities, AML with myelodysplasia-related changes, Therapy-related myeloid neoplasms, Myeloid sarcoma, Myeloid proliferations related to Down syndrome, Blastic plasmacytoid dendritic cell neoplasm, and AML not otherwise categorized. In certain other instances, the antigen-binding tandem diabody as described herein is administered for the treatment of AML with Recurrent Genetic Abnormalities, AML with myelodysplasia-related changes, Therapy-related myeloid neoplasms, Myeloid sarcoma, Myeloid proliferations related to Down syndrome, Blastic plasmacytoid dendritic cell neoplasm, or AML not otherwise categorized.

In some other embodiments, the antigen-binding tandem diabody as described herein is administered for the treatment of a newly diagnosed, recurrent or refractory AML.

In some embodiments, a CD33 and CD3 binding protein, e.g., an antigen-binding tandem diabody, as described herein is administered to a patient having received hematopoietic stem cell transplantation (HCT) for the treatment of recurrent or refractory AML. Patients who received HCT are a specific patient population that is amenable to the CD33 and CD3 binding protein for the treatment of AML. It is contemplated that with the receipt of HCT, a patient reestablishes his or her immune system including lymphocytes thereby allowing the CD33 and CD3 binding protein to more effectively engage cytotoxic T cells and kill tumor cells.

In many or most cases, patients receiving HCT have failed a prior therapy for the treatment of AML such as chemotherapy or radiation and are now in remission. In some embodiments, the patients receiving HCT have failed first line chemotherapy or radiation. In some embodiments, the patients receiving HCT have failed single line chemotherapy or radiation. In some AML patients receiving HCT, the patients are in first complete remission (CR1). In some embodiments, the AML patients receiving HCT are relapsed AML patients who are in second complete remission (CR2).

In some embodiments, the hematopoietic stem cell transplantation is allogenic (allo-HCT). In an Allo-HCT, the stem cells originate from someone, i.e., donor other than the patient that is human leukocyte antigen (HLA)-antigen matched. Matched donors can be related or unrelated to the patient. In some cases, a partially matched donor, with one antigen mismatch, can be used for allo-HCT. Common sources of cells from donors include bone marrow and peripheral blood stem cells. For those patients who do not have an HLA-matched or -partially matched related or unrelated donor available, alternative donor sources may be used. Exemplary alternative donor options include umbilical cord transplantation or haploidentical transplantation. Advantages of an allo-HCT include the use of a tumor-free graft and the immune-mediated graft-vs-leukemia effect. When the donor immune cells are infused into the body, they may recognize any remaining leukemia cells as being foreign to them and attack them. Disadvantages of an allo-HCT include difficulty in finding matched or partially matched donors as well as graft-vs-host disease, where the immune system established by the donor's cells recognizes that the patient's own tissues as foreign and attacks them.

In some other embodiments, the hematopoietic stem cell transplantation is autologous (auto-HCT). Autologous HCT requires the extraction, commonly by apheresis, of hematopoietic stem cells from the patient and storage of the harvested cells in a freezer. The patient is then treated with high-dose chemotherapy with or without radiotherapy with the intention of eradicating the patient's malignant cell population at the cost of partial or complete bone marrow ablation, or in other words, destruction of patient's bone marrow function to grow new blood cells. The patient's own stored stem cells are then transfused into his/her bloodstream, where they replace destroyed tissue and resume the patient's normal blood cell production. Autologous transplants have the advantage of lower risk of infection during the immune-compromised portion of the treatment since the recovery of immune function is rapid. Also, the incidence of patients experiencing rejection, which is acute or chronic graft-versus-host disease, is very rare due to the donor and recipient being the same individual.

In further embodiments, the patient receives a conditioning regimen prior to the HCT. In some embodiments, the conditioning regimen prior to HCT is able to provide adequate immunosuppression to guarantee engraftment and have no significant toxicities. The conditioning regimen is either myeloablative or non-myeloablative, also known as reduced intensity conditioning (RIC) regimen.

In some embodiments, the conditioning regimen is myeloablative. Myeloablative conditioning regimen ablates the cells in the bone marrow, including the AML cells and is usually carried out by total body irradiation (TBI), administration of a cyclophosphamide, administration of busulfan, or combinations thereof. Exemplary cyclophosphamides include endoxan, cytoxan, neosar, procytox, revimmune, and cycloblastin. In some embodiments, the conditioning regimen is non-myeloablative, i.e., reduced intensity conditioning (RIC). RIC regimen includes doses of chemotherapies and/or radiation lower than myeloablative therapy. Thus an RIC regimen is considered a gentler regimen that does not eradicate all bone marrow cells and can be used in patients such as the elderly that cannot undergo a myeloablative conditioning regimen.

In some embodiments, the CD33 and CD3 binding protein, e.g., an antigen-binding tandem diabody, described herein is administered to AML patients who received an auto-HCT after a myeoloablative conditioning regimen. In some embodiments, the antigen-binding tandem diabody is administered to AML patients having received an allo-HCT after a myeoloablative conditioning regimen. In some embodiments, the patients receiving allo-HCT after a myeloablative conditioning regimen are in complete remission (CR), and administering the CD33 and CD3 binding protein as described herein post allo-HCT reduces the probability of occurrence of a relapsed or refractory AML. In some embodiments, the patients receiving allo-HCT after a myeloablative conditioning regimen are in CR but have minimal residual disease (MRD), and administering the CD33 and CD3 binding protein as described herein post allo-HCT reduces the probability of occurrence of relapsed or refractory AML. In some embodiments, the patients receiving allo-HCT after a myeloablative conditioning regimen have MRD, and administering the CD33 and CD3 binding protein as described herein post allo-HCT reduces the probability of occurrence of relapsed or refractory AML.

Certain pre-clinical studies have indicated that more intensive conditioning regimens result in a pro-inflammatory cytokine milieu that favors the development of acute graft versus host disease. Exemplary intensive conditioning regiments include very high-dose TBI-regimen. In some embodiments, administering the CD33 and CD3 binding protein described herein to AML patients who received allo-HCT, after an intensive conditioning regimen, does not result in a pro-inflammatory cytokine milieu and reduces the probability of occurrence of acute graft versus host disease.

In further embodiments, the CD33 and CD3 binding protein, e.g., an antigen-binding tandem diabody, is administered to AML patients who received an auto-HCT, after a RIC regimen. In some embodiments, the antigen-binding tandem diabody is administered to AML patient who received an allo-HCT, after a RIC regimen. Exemplary minimally intensive conditioning regimens include administering fludarabine in combination with TBI. In some embodiments, the fludarabine is administered at a dose of 30 mg/m$^2$/day, for 3 days, along with 2 Gy TBI. Some studies have reported that non-myeloablative or RIC conditioning regimen is associated with an overall survival rate of 34% to 50% at two years, a non relapse mortality (NRM) rate of 22% to 34% at two years, an acute graft versus host disease rate of 33% to 35%, and a chronic graft versus host disease rate of 41% to 53%. In some embodiments, the CD33 and CD3 binding protein as described herein is administered to AML patients who have received allo-HCT after a RIC conditioning regimen. In some embodiments, administering the antigen-binding tandem diabody as described herein to AML patients who have received allo-HCT after a RIC conditioning regimen results in an improved overall survival rate, reduced rate of NRM, and/or reduced rate of occurrence of acute or chronic graft versus host disease.

In some embodiments, the CD33 and CD3 binding protein is administered to AML patients who received an allo-HCT after a RIC regimen. In some embodiments, the patients receiving allo-HCT, after a RIC regimen are in complete remission (CR), and administering the CD33 and CD3 binding protein as described herein post allo-HCT reduces the probability of occurrence of a relapsed or refractory AML. In some embodiments, the patients receiving allo-HCT after a RIC regimen are in CR but have minimal residual disease (MRD), and administering the antigen-binding tandem diabody as described herein post allo-HCT reduces the probability of occurrence of relapsed or refractory AML. In some embodiments, the patients receiving allo-HCT after a RIC regimen have MRD, and administering the antigen-binding tandem diabody as described herein post allo-HCT reduces the probability of occurrence of relapsed or refractory AML.

In some embodiments, the CD33 and CD3 binding protein as described herein is administered to patients who have received allo-HCT, along with donor lymphocytes, during AML progression. In some embodiments, the antigen-binding tandem diabody as described herein is administered to patients who have received allo-HCT, without donor lymphocytes, during AML progression.

In some embodiments, the overall response rate in AML patients administered with the CD33 and CD3 binding protein as described herein post allo-HCT is higher than the overall response rate in AML patients administered with the CD33 and CD3 binding protein as described herein without prior allo-HCT. In some embodiments, AML patients who receive allo-HCT after a myeloablative or reduced intensity conditioning regimen have functional T cells for binding of the CD33 and CD3 binding protein as described herein, and administering the the CD33 and CD3 binding protein as described in the presence of functional T cells results in improved success rate of treatment of AML.

In further embodiments, the antigen-binding tandem diabody as described herein is administered for the treatment of a preleukemia blood disorder such as myeloid dysplastic syndrome (MDS) or myeloproliferative disease (MPD). In certain instances, the antigen-binding tandem diabody as described herein is administered for the treatment of MDS. In certain instances, the antigen-binding tandem diabody as described herein is administered for the treatment of MPD.

In other embodiments, the antigen-binding tandem diabody as described herein is administered for the treatment of multiple myeloma. In further embodiments, the antigen-binding tandem diabody as described herein is administered for the treatment of chronic myelomonocytic leukemia (CMML).

In other embodiments, the antigen-binding tandem diabody as described herein is administered for inhibiting or eliminating myeloid derived suppressor cells (MDSCs). MDSCs highly overexpress CD33 in certain isolated diseased tissues and possess strong immunosuppressive activities. In certain human cancers (CD33$^+$ as well as non-CD33$^+$), MDSCs proliferate and are activated to suppress tumor-specific CD4$^+$ T-cell responses and induce $T_{reg}$ cells, allowing the tumor or cancer to flourish in a microenvironment. In chronic inflammation, MDSCs are reportedly expanded and found at inflammation sites to suppress T cell immune function. In other embodiments, the antigen-binding tandem diabody as described herein is administered for treating a condition associated with MDSCs. In yet other embodiments, the antigen-binding tandem diabody as described herein is administered to treat immune suppression. In yet other embodiments, the antigen-binding tandem diabody as described herein is administered to treat inflammation suppressed by MDSCs. In yet other embodiments, the antigen-binding tandem diabody as described herein is administered to treat a decreased immune response caused by MDSCs. In yet other embodiments, the antigen-binding tandem diabody as described herein is administered to treat angiogenesis, tumor invasion, or metastasis of cancers that are promoted by MDSCs. In yet other embodiments, the antigen-binding tandem diabody as described herein is administered to treat a cancer or tumor that is enhanced, augmented, aggravated or increased by MDSCs.

The antigen-binding tandem diabody described herein is contemplated for use as a medicament. Administration is effected by different ways, e.g. by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosages for any one patient depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology. An "effective dose" useful for treating and/or preventing AML may be determined using known methods.

In further embodiments, the antigen-binding tandem diabody described herein is administered in combination with a standard therapy to CD33+ cancers, diseases or conditions. Standard therapies include chemotherapies, immunotherapies, hormone therapies, radiation, surgery, gene therapies and the like. In certain instances, the antigen-binding tandem diabody described herein is administered in combination with a standard AML therapy. In certain instances, the antigen-binding tandem diabody described herein is administered in combination with cytarabine, azacitidine, decitabine, an anthracycline (e.g., daunorubicin, idarubicin, doxorubicin, and the like), amsacrine, fludarabine, clofarabine, cladribine, nelarabine, methotrexate, bortezomib, carfilzomib, melphalan, ibrutinib, thalidomide, lenalidomide, pomalidomide, apremilast, an epipodophyllotoxin (e.g., etoposide, teniposide, and the like), an anthracenedione (e.g., mitoxantrone, pixantrone, losoxantrone, piroxantrone, ametantrone and the like) an anti-CD20 agent (e.g., rituximab, ocrelizumab, ofatumumab, or combinations thereof. In certain instances, the antigen-binding tandem diabody described herein is administered in combination with cytarabine (ara-C). In certain instances, the antigen-binding tandem diabody described herein is administered in combination with azacitidine. In certain instances, the antigen-binding tandem diabody described herein is administered in combination with decitabine. In further instances, the antigen-binding tandem diabody described herein is administered in combination with an anthracycline (e.g., daunorubicin, idarubicin, doxorubicin, and the like). In other instances, the antigen-binding tandem diabody described herein is administered in combination with a checkpoint inihibitor (e.g., PD-1 inhibitor, CTLA-4 inhibitor, and the like). In yet other instances, the antigen-binding tandem diabody described herein is administered in combination with an epipodophyllotoxin (e.g., etoposide, teniposide, and the like). In yet other instances, the antigen-binding tandem diabody described herein is administered in combination with an anthracenedione (e.g., mitoxantrone, pixantrone, losoxantrone, piroxantrone, ametantrone and the like).

The examples below further illustrate the described embodiments without limiting the scope of the invention.

Example 1

Cloning of DNA Expression Constructs Encoding Single-Chain Fv Antibodies

For bacterial expression of anti-CD33 single-chain Fv (scFv) antibodies in E. coli, DNA coding sequences of all molecules were cloned into a bacterial expression vector. All expression constructs were designed to contain coding sequences for an N-terminal signal peptide and C-terminal hexa-histidine (6×His)-tag to facilitate antibody secretion into the periplasm and purification, respectively. The amino acid sequences of the VL and VH-domains from all anti-CD33 scFv clones are shown in Table 3 and Table 4.

Expression of Recombinant Anti-CD33 scFv Antibodies in E. coli

Recombinant scFv antibodies were expressed as soluble secreted proteins in the E. coli periplasm. In a first step a small medium culture supplemented with ampicillin was inoculated with transformed bacteria and incubated for 16 h at 28° C. Subsequently, optical density was adjusted by adding a second medium supplemented with ampicillin and incubated once more at 28° C. until an optical density in the range of 0.6-0.8 at 600 nm was reached. Protein expression was induced through addition of 50 μM IPTG and incubation of cultures at 21-28° C. and 200 rpm for up to 16 h. Following incubation, cells were pelleted (30 min, 4° C., 7500 rpm) and stored at −20° C. until further processing.

Purification of Anti-CD33 Single-Chain Fv Antibodies

Recombinant scFv were extracted from E. coli periplasm following centrifugation of bacterial cell cultures by resuspending cell pellets in buffer and incubation for 30 min at room temperature with gentle agitation. Cells were pelleted and supernatants containing recombinant proteins were kept. The procedure was repeated once more before supernatants were pooled and homogenized by ultrasonication. Homogenates were diluted, supplemented with low concentrations of imidazole and loaded onto a prepacked immobilized metal affinity chromatography (IMAC) column (GE Healthcare). The column was washed until baseline was reached and bound protein was then eluted with an imidazole buffer. Antibody containing fractions were pooled and subsequently purified by size-exclusion chromatography (SEC). Finally, protein eluates were concentrated by ultrafiltration and dialysed against storage buffer. Subsequent to low pH treatment (incubation at pH 3.0 for 20-24 h at 37° C.), samples were neutralized using Tris. Purified proteins were stored as aliquots at −80° C. until use.

Example 2

Cloning of DNA Expression Constructs Encoding Tandem Diabodies (TandAb®)

Figure 3:
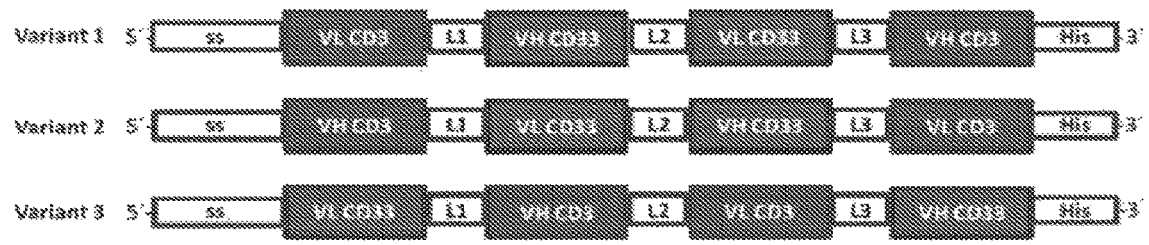
FIG. 3 Domain order variants of CD33/CD3 tandem diabodies. Variations of domain order of variable heavy (VH) and variable light (VL) chains within gene sequences encoding tandem diabodies allows production of antibodies with CD33 and CD3 specificities located on the inside or outside of the molecule. Domain specificities, location of signal sequences (ss) and linkers (L1, L2, L3) and affinity tags (His) as well as 5'- and 3'-ends are indicated.

For expression of bispecific tandem diabodies in CHO cells, coding sequences of all molecules were cloned into a mammalian expression vector system. The anti-CD33 scFv domains of Example 1 were used to construct CD33/CD3 tandem diabodies in combination with an anti-CD3 scFv domain, with domains organized as shown in Table 7 and FIG. 3. In brief, gene sequences encoding anti-CD33 VH and VL domains separated by a peptide linker (VH-linker-VL or VL-linker-VH) were synthesized and subcloned. The resulting construct was digested to generate separate VH and VL coding sequences utilizing a Bam HI restriction site located within the linker sequence. These VH and VL fragments were then ligated with a DNA fragment encoding VH and VL domains of anti-CD3 (VH-linker-VL or VL-linker-VH) to yield the final construct. Domain order variants 1 to 3 of CD33/CD3 tandem diabodies are shown in FIG. 3. All expression constructs were designed to contain coding sequences for an N-terminal signal peptide and a C-terminal hexahistidine (6×His)-tag to facilitate antibody secretion and purification, respectively.

Expression of Tandem Diabodies in Stably Transfected CHO Cells

A CHO cell expression system (Flp-In®, Life Technologies), a derivative of CHO-K1 Chinese Hamster ovary cells (ATCC, CCL-61) (Kao and Puck, Proc. Natl. Acad Sci USA 1968; 60(4):1275-81), was used. Adherent cells were subcultured according to standard cell culture protocols provided by Life Technologies.

For adaption to growth in suspension, cells were detached from tissue culture flasks and placed in serum-free medium. Suspension-adapted cells were cryopreserved in medium with 10% DMSO.

Recombinant CHO cell lines stably expressing secreted tandem diabodies were generated by transfection of suspension-adapted cells. During selection with the antibiotic Hygromycin B viable cell densities were measured twice a week, and cells were centrifuged and resuspended in fresh selection medium at a maximal density of $0.1 \times 10^6$ viable cells/mL. Cell pools stably expressing tandem diabodies were recovered after 2-3 weeks of selection at which point cells were transferred to standard culture medium in shake flasks. Expression of recombinant secreted proteins was confirmed by performing protein gel electrophoresis or flow cytometry. Stable cell pools were cryopreserved in DMSO containing medium.

Tandem diabodies were produced in 10-day fed-batch cultures of stably transfected CHO cell lines by secretion into the cell culture supernatant. Cell culture supernatants were harvested after 10 days at culture viabilities of typically >75%. Samples were collected from the production cultures every other day and cell density and viability were assessed. On day of harvest, cell culture supernatants were cleared by centrifugation and vacuum filtration before further use.

Protein expression titers and product integrity in cell culture supernatants were analyzed by SDS-PAGE.

Purification of Tandem Diabodies

Tandem diabodies were purified from CHO cell culture supernatants in a two-step procedure. The His6-tagged constructs were subjected to Ni-NTA Superflow chromatography in a first step followed by preparative size exclusion chromatography (SEC) on Superdex 200 in a second step. Eluted tandem diabodies were characterized with regards to their homodimer (tandem diabody) content and pooled if the homodimer content was 90% or higher. Finally, pooled samples were buffer-exchanged and concentrated by ultrafiltration to a typical concentration of >1 mg/mL. Purity and homogeneity (typically >90%) of final samples were assessed by SDS PAGE under reducing and non-reducing conditions, followed by immunoblotting using an anti-His-Tag antibody as well as by analytical SEC, respectively. Purified proteins were stored at aliquots at −80° C. until use.

Polypeptides of CD33/CD3 tandem diabodies are shown in Table 7 and FIG. 3. Each tandem diabody consists of two identical polypeptides (FIG. 1). Both outer linkers L1 and L3 were comprised of six amino acids GGSGGS (SEQ ID NO:95), whereas the central peptide linker 2 varied in length (4-6 amino acids) with the sequences GGSG (SEQ ID NO:96), GGSGG (SEQ ID NO:97), or GGSGGS (SEQ ID NO:95), respectively.

Using a series of anti-CD33 variable domains and anti-CD3 variable domains a large number of tandem diabody molecules was generated that could be stably produced in transfected cell lines and that maintained stability at body temperature as well as after repeated freeze/thaw cycles. To facilitate further development and preclinical toxicology studies, emphasis was placed on the selection of tandem diabody molecules that showed binding to both human and cynomolgus monkey CD33. Examples of complete amino acid sequences are shown for the single-chain of tandem diabodies 12 (SEQ ID NO:109), 14 (SEQ ID NO:111) and 16 (SEQ ID NO:113) in FIGS. 10L, 10N and 10P, respectively. In this example the order of the variable domains and their linkers for the structures is: VL (CD3)-L1-VH (CD33)-L2-VL (CD33)-L3-VH (CD3). The C-terminal hexa-histidine (6×His)-tag is cleaved during purification. Complete amino acid sequences for the above mentioned tandem diabodies, after removal of the hexa-histidine tag, are tandem diabody 12 (SEQ ID NO:134), tandem diabody 14 (SEQ ID NO:136) and tandem diabody 16 (SEQ ID NO:138), as shown in FIGS. 11L, 11N and 11P, respectively.

Example 3

Determination of Antibody Affinity by Flow Cytometry

Cells were incubated with 100 μL of serial dilutions of CD33/CD3 tandem diabodies. After washing three times with FACS buffer the cells were incubated with 0.1 mL of 10 μg/mL mouse monoclonal anti-His antibody in the same buffer for 45 min on ice. After a second washing cycle, the cells were incubated with 0.1 mL of 15 μg/mL FITC-conjugated goat anti-mouse IgG antibodies under the same conditions as before. As a control, cells were incubated with the anti-His IgG followed by the FITC-conjugated goat anti-mouse IgG antibodies without anti-CD33 tandem diabodies. The cells were then washed again and resuspended in 0.2 mL of FACS buffer containing 2 μg/mL propidium iodide (PI) in order to exclude dead cells. The fluorescence of $1 \times 10^4$ living cells was measured using a Beckman-Coulter FC500 MPL flow cytometer using the MXP software (Beckman-Coulter, Krefeld, Germany) or a Millipore Guava EasyCyte flow cytometer using the Incyte software (Merck Millipore, Schwalbach, Germany). Mean fluorescence intensities of the cell samples were calculated using CXP software (Beckman-Coulter, Krefeld, Germany) or Incyte software (Merck Millipore, Schwalbach, Germany). After subtracting the fluorescence intensity values of the cells stained with the secondary and tertiary reagents alone the values were used for calculation of the $K_D$ values with the equation for one-site binding (hyperbola) of the Graph-Pad Prism (version 6.00 for Windows, GraphPad Software, La Jolla Calif. USA).

The tandem diabodies were tested for their binding affinities to human CD3+ and CD33+ cells and cynomolgus CD3+ and CD33+ cells. Exemplary binding data for selected tandem diabodies are summarized in Table 8:

TABLE 8

CD3 and CD33 binding characteristics of CD33/CD3 tandem diabodies:

| TandAb | $K_D$ on T cells [nM] | $K_D$ on HL-60 [nM] | $K_D$ on KG-1 [nM] | $K_D$ on U-937 [nM] | $K_D$ ratio cynoCD33/ huCD33 | $EC_{50}$ on HL-60 [pM] |
|---|---|---|---|---|---|---|
| 01 | 94.2 | 0.6 | 0.9 | 7.1 | 0.7 | 1.9 |
| 02 | 69.8 | 0.2 | 0.3 | 0.9 | 1.1 | 0.5 |
| 03 | 81.9 | 1.1 | 1.8 | 8.9 | 0.6 | 3.6 |
| 04 | 79.3 | 0.5 | 0.5 | 1.7 | 1.1 | 1.8 |
| 05 | 69.5 | 1.0 | 1.2 | 6.2 | 0.8 | 2.7 |
| 06 | 86.3 | 0.4 | 0.5 | 1.6 | 0.8 | 1.6 |
| 07 | 49.7 | 13.7 | 47.9 | 47.1 | 45.8 | 17.8 |
| 08 | 2.4 | 0.3 | 0.5 | 1.8 | 0.6 | 1.8 |
| 09 | 2.4 | 0.5 | 0.3 | 2.2 | 1.0 | 6.8 |
| 10 | 1.9 | 0.5 | 1.0 | 1.7 | 0.8 | 7.0 |
| 11 | 2.6 | 0.3 | 0.5 | 0.6 | 1.2 | 5.9 |
| 12 | 1.5 | 0.3 | 0.9 | 0.5 | 1.7 | 1.3 |
| 13 | 55.7 | 0.2 | 0.3 | 0.5 | 1.6 | 1.1 |
| 14 | 2.1 | 0.3 | 0.3 | 1.2 | 1.0 | 1.6 |
| 15 | 1.3 | 0.4 | 0.3 | 0.9 | 1.1 | 1.8 |
| 16 | 2.1 | 0.3 | 0.2 | 0.3 | 1.4 | 1.5 |
| 17 | 3.3 | 5.0 | 52.5 | 24.4 | 1.9 | 18.4 |
| 18 | 1.9 | 3.4 | 16.3 | 15.1 | 3.1 | 6.3 |

TABLE 8-continued

CD3 and CD33 binding characteristics of CD33/CD3 tandem diabodies:

| TandAb | $K_D$ on T cells [nM] | $K_D$ on HL-60 [nM] | $K_D$ on KG-1 [nM] | $K_D$ on U-937 [nM] | $K_D$ ratio cynoCD33/ huCD33 | $EC_{50}$ on HL-60 [pM] |
|---|---|---|---|---|---|---|
| 19 | 6.3 | 2.8 | 3.6 | 5.4 | 37.3 | 5.7 |
| 20 | 143.8 | 4.1 | 7.0 | 7.2 | 33.8 | 10.0 |
| 21 | 2.1 | 9.7 | 25.1 | 80.2 | 0.9 | 7.6 |
| 22 | 4.1 | 0.7 | 2.0 | 8.6 | 0.6 | 3.2 |
| 23 | 97.2 | 0.4 | 1.0 | 5.1 | 1.9 | 2.8 |
| 24 | 2.3 | 5.6 | 12.4 | 39.5 | 1.8 | 9.6 |

$K_D$ ratio cyno CD33/human CD33 was calculated based on the $K_D$ values measured on CHO cells expressing cynomolgus CD33 and human CD33, respectively. ‡$K_D$ ratio hu CD3/hu CD33 was calculated based on the $K_D$ values measured on Jurkat cells (hu CD3) and the mean $K_D$ of three human CD33+ tumor cell lines (HL-60, KG-1, U937).

CD3 binding affinity and crossreactivity were evaluated in titration and flow cytometric experiments on CD3+ Jurkat cells (provided by Dr. Moldenhauer, DKFZ Heidelberg; human acute T-cell leukemia) and the cynomolgus CD3+ HSC-F cell line (JCRB, cat.: JCRB1164). CD33 binding and crossreactivity were assessed on the human CD33+ tumor cell lines: HL-60 (DSMZ, cat.: ACC 3, human B cell precursor leukemia), U-937 (DSMZ, cat.: ACC5; human histiocytic lymphoma), and KG-1 (DSMZ, cat.: ACC14; acute myeloid leukemia). The $K_D$ ratio of crossreactivity was calculated using the $K_D$ values determined on the CHO cell lines expressing either recombinant human or recombinant cynomolgus antigens.

The tandem diabodies exhibited a relatively high affinity to human CD33+ on most of the tested tumor cell lines below 1 nM. Affinities to human CD3 were determined to be equal or less than 2 nM.

Example 4

Cytotoxicity Assay

For the cytoxicity assay target cells cultured under standard conditions were harvested, washed and resuspended in diluent C, provided in the PKH67 Green Fluorescent Cell Linker Mini Kit, to a density of $2 \times 10^7$ cells/mL. The cell suspension was then mixed with an equal volume of a double concentrated PKH67-labeling solution and incubated for 2-5 min at RT. The staining reaction was performed by adding an equal volume of FCS and incubating for 1 min. After washing the labeled target cells with complete RPMI medium, cells were counted and resuspended to a density of $2 \times 10^5$ cells/mL in complete RPMI medium. $2 \times 10^4$ target cells were then seeded together with enriched human T-cells as effector cells at an E:T ratio of 5:1, in the presence of increasing concentrations of the indicated tandem diabodies in individual wells of a microtiter plate, in a total volume of 200 µL/well. Spontaneous cell death and killing of targets by T-cells in the absence of antibodies were determined for at least three replicates on each plate. After centrifugation the assay plates were incubated for the indicated periods of time at 37° C. in a humidified atmosphere with 5% $CO_2$. After incubation, cultures were washed once with FACS buffer and then resuspended in 150 µL FACS buffer supplemented with 2 µg/mL PI. The absolute amount of living target cells was measured by a positive green staining with PKH67 and negative staining for PI using a Beckman-Coulter FC500 MPL flow cytometer (Beckman-Coulter) or a Millipore Guava EasyCyte flow cytometer (Merck Millipore). Based on the measured remaining living target cells, the percentage of specific cell lysis was calculated according to the following formula: [1-(number of livingtargets$_{(sample)}$/number of living targets$_{(spontaneous)}$)]×100%. Sigmoidal dose response curves and $EC_{50}$ values were calculated by non-linear regression/4-parameter logistic fit using the GraphPad Software. The lysis values obtained for a given antibody concentration were used to calculate sigmoidal dose-response curves by 4 parameter logistic fit analysis using the Prism software.

$EC_{50}$ values were determined in 20-24 hour assay on CD33+ U-937 (DSMZ, cat.: ACC5; human histiocytic lymphoma) target cells with enriched human T-cells as effector cells at a ratio of 5:1. Some tandem diabodies were also tested in cytotoxicity assays on CD33+ KG-1 (DSMZ, cat.: ACC14; acute myeloid leukemia) and HL-60 target cells. Specifically, HL-60 cells were chosen as a model of an AML with relatively high cell surface expression of CD33 (arbitrary MFI [mean±SEM]: 3,133±215; n=3), and KG-1a was chosen as a model of an AML with very limited CD33 expression (arbitrary MFI: 277±11; n=3). Exemplary cytotoxicity data for selected tandem diabodies are summarized in Table 9. Additional cytotoxicity data for HL-60 cell lines is found on Table 8, last column.

TABLE 9

In vitro potency of CD33/CD3 tandem diabodies on different CD33+ tumor cell lines:

| Tandem diabody | $EC_{50}$ [pM (pg/mL)] on human CD33+ target cell lines | | | |
|---|---|---|---|---|
|  | HL-60 | U-937 | KG-1 | mean |
| 12 | 1.3 (137) | 0.8 (84) | 1.2 (126) | 1.1 (116) |
| 14 | 1.6 (168) | 3.6 (378) | 2.6 (273) | 2.6 (273) |
| 16 | 1.5 (158) | 1.9 (200) | 1.8 (189) | 1.7 (179) |

$EC_{50}$ values were determined in FACS-based cytotoxicity assays with primary human T-cells as effector cells at an E:T ratio of 5:1 on the indicated target cell lines incubated for 20-24 hours Each tandem diabody was tested on each tumor cell line in at least two independent experiments. Mean values are presented.

Example 5

Figure 4:
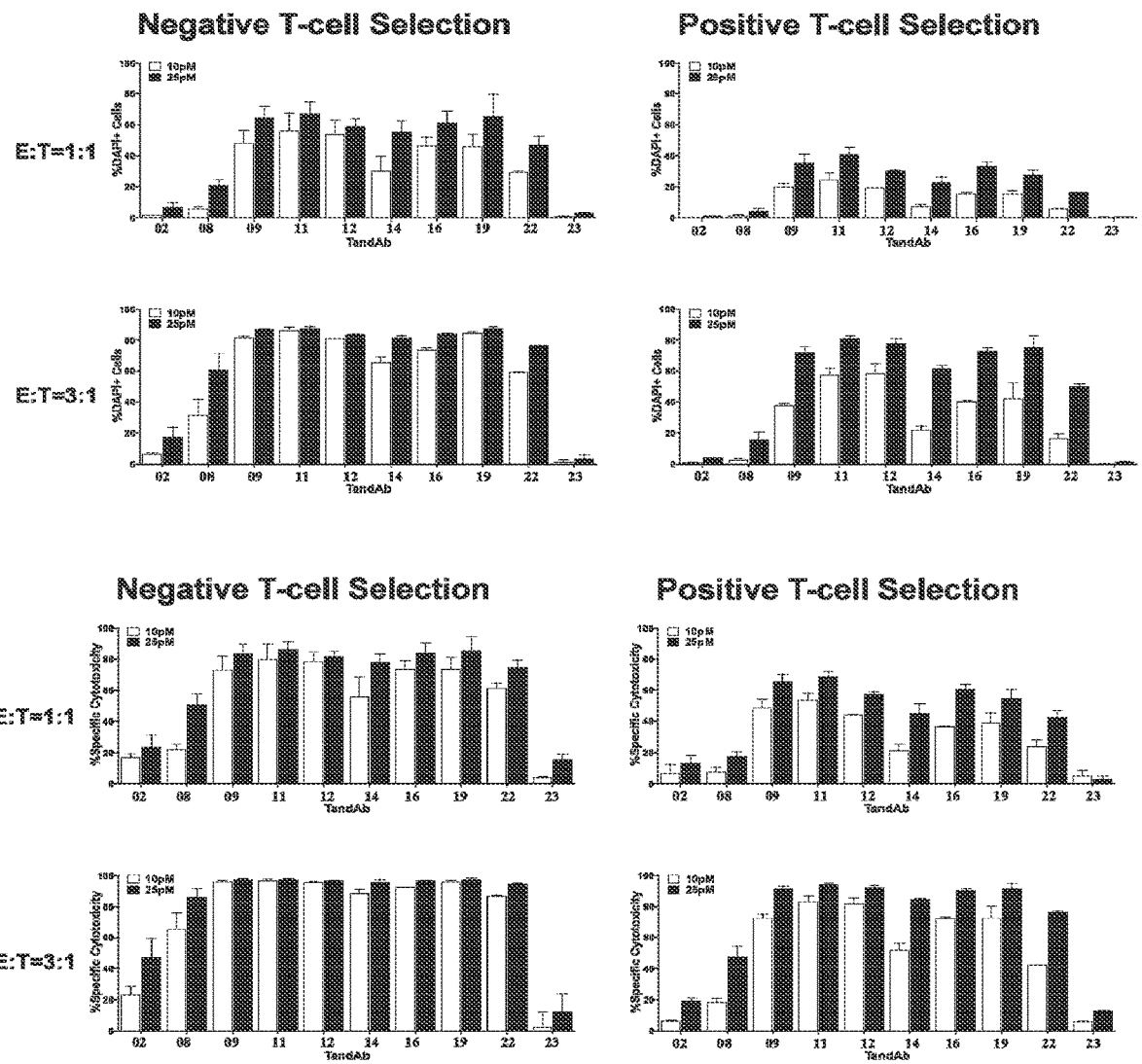
FIG. 4 Comparison of positively enriched vs. negatively selected healthy donor T-cells. KG-1a cells were incubated with 10 pM (approx. 1 ng/mL) and 25 pM (approx. 2.5 ng/mL) of one of 10 selected tandem diabodies and either negatively selected healthy donor T-cells or positively selected healthy donor T-cells at an E:T cell ratio of 1:1 or 3:1, as indicated. After 48 hours, cell counts were determined and cytotoxicity was assessed with DAPI staining. Results are shown as mean±SEM for the percentage of dead cells (upper panels) and the percentage of specific cytotoxicity (lower panels) from 3 independent experiments performed in duplicate wells.

Further Cytotoxicity Screening Experiments in Human CD33+ AML Cell Lines at 48 Hours As described above significant cytotoxicity was detected as early as 24 hours, however higher levels of toxicity can be detected at 48 hours. For the subsequent assays a 48-hour time point was chosen. The impact of T-cell selection on tandem diabody-induced cytotoxicity was tested. To accomplish this, unstimulated PBMCs from a healthy volunteer donor were obtained, and CD3+ cells were isolated both by simple "positive enrichment" via use of CD3 microbeads as well as by more complex "negative selection" via a microbead cocktail of antibodies against CD14, CD15, CD16, CD19, CD34, CD36, CD56, CD123, and CD235a. As depicted in FIG. 4, tandem diabody-induced cytotoxicity was greater with negatively selected healthy donor T-cells than positively selected T-cells. However, the relative cytotoxic activities of individual tandem diabodies were unaffected by the method of T-cell selection. Therefore the subsequent assays were performed with positively enriched healthy donor T-cells.

Unstimulated mononuclear cells were collected from healthy adult volunteers via leukapheresis by the Fred Hutchinson Cancer Research Center (FHCRC) Hematopoietic Cell Processing Core (Core Center of Excellence) under research protocols approved by the FHCRC Institutional Review Board. T-cells were enriched through magnetic cell sorting either via CD3 Microbeads ("positive enrichment") or via Pan T-Cell Isolation Kit ("negative selection"; both from Miltenyi Biotec, Auburn, Calif.), and then frozen in aliquots and stored in liquid nitrogen. Thawed cell aliquots were labeled with 3 μM CellVue Burgundy (eBioscience, San Diego, Calif.) according to the manufacturer's instructions. Purified PBMCs were cultured in the presence of various concentrations of tandem diabody molecules.

Figure 5:
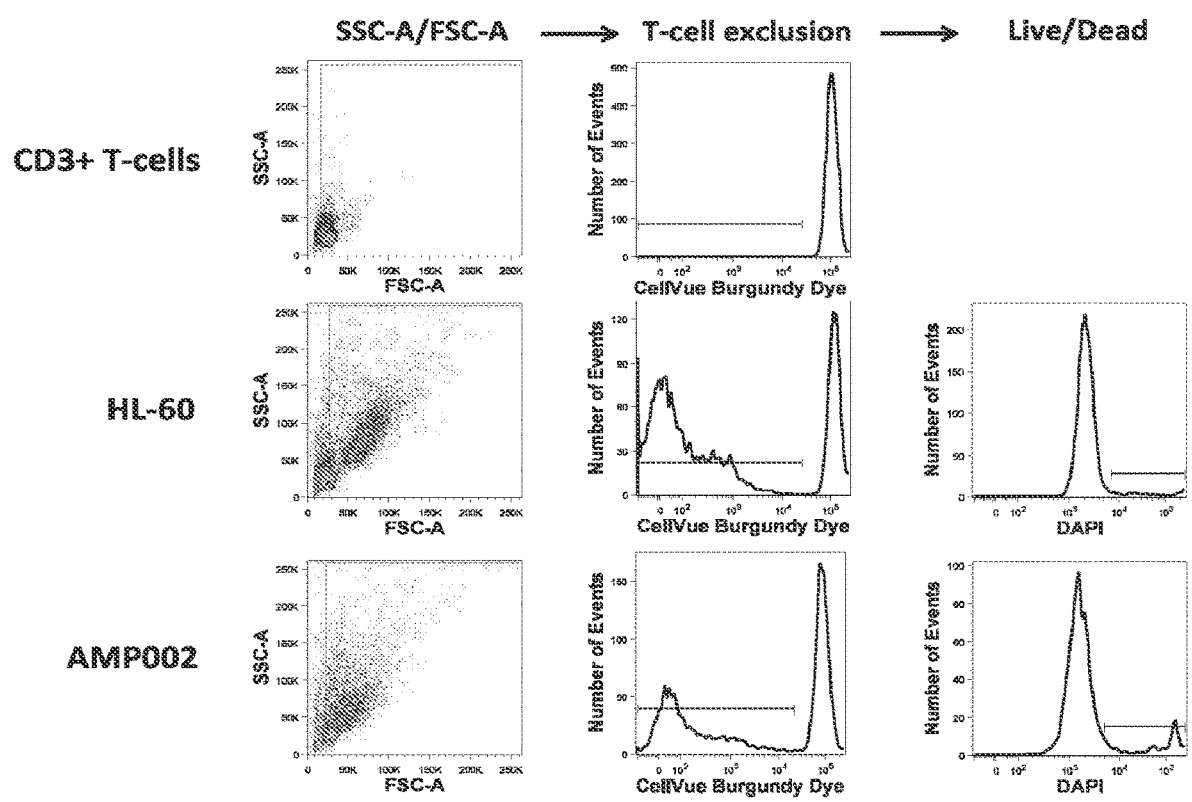
FIG. 5 Analysis strategy. Scatter and histogram plots from one healthy donor T-cell aliquot and 1 representative AML cell line (HL-60) and primary AML specimen (AMP002) each illustrating the strategy pursued to determine tandem diabody-induced cytotoxicity. FSC, forward scatter; SSC, side scatter.

For the quantification of drug-induced cytotoxicity cells were incubated at 37° C. (in 5% $CO_2$ and air), as in Example 4, at different E:T cell ratios. After 24-72 hours, cell numbers and drug-induced cytotoxicity, using DAPI to detect non-viable cells, were determined using a LSRII cytometer (BD Biosciences) and analyzed with FlowJo. AML cells were identified by forward/side scatter properties and, in experiments where healthy donor T-cells were added, negativity for CellVue Burgundy dye (FIG. 5). Drug-induced specific cytotoxicity is presented as: % cytotoxicity=100×(1−live target cells$_{treated}$/live target cells$_{control}$). Results from cytotoxicity assays are presented as mean values±standard error of the mean (SEM). Spearman nonparametric correlation was used to compute correlations between continuous sample characteristics. All P-values are two-sided. Statistical analyses were performed using GraphPad Prism software.

In the absence of healthy donor T-cells, neither of the CD33/CD tandem diabodies exerted any noticeable cytotoxic effect on AML cell lines in the absence of T-cells, confirming the absolute requirement for T-cells for their cytotoxic effects (data not shown). In the presence of T-cells, the extent of tandem diabody-induced specific cytotoxicity was dependent on the concentration of the tandem diabody as well as the E:T cell ratio. Direct head-to-head comparisons between the CD33/CD3-directed tandem diabody molecules and one control tandem diabody (00) indicated considerable differences in antibody-induced cytotoxicity in both HL-60 cells (FIG. 6A/B and Table 10) and KG-1a cells (FIG. 6C/D and Table 10), with results being highly reproducible in repeat experiments. Overall, the degree of tandem diabody-induced cytotoxicity correlated with the binding affinity for CD3 on primary human T-cells (for cytotoxicity in KG-1a cells at 25 pM (approx. 2.5 ng/mL) and E:T=5:1: r=−0.542, p=0.009; for cytotoxicity in HL-60 cells at 25 pM and E:T=5:1: r=−0.391, p=0.07). The tandem diabodies 12, 14, 16 were highly cytotoxic for both HL-60 and KG-1a cells.

TABLE 10

CD25 and CD69 induction and cytotoxicity at 48 h of CD33/CD3 tandem diabodies

| Tandem Diabody[1] | CD3 $K_D$ (nM) Human T-cells | CD33 $K_D$ (nM) HL-60 cells | CD25 Induction $EC_{50}$ (pM)[2] | CD69 Induction $EC_{50}$ (pM)[2] | T cell Proliferation in PBMC $EC_{50}$ (pM)[3] | Cytotoxicity HL-60 cells (% ± SEM)[4] | Cytotoxicity KG-1a cells (% ± SEM)[4] |
|---|---|---|---|---|---|---|---|
| 15 | 1.3 | 0.4 | 6 | 7 | 7 | 82.9 ± 3.7 | 80.2 ± 1.9 |
| 12 | 1.5 | 0.3 | 6 | 3 | 2 | 84.7 ± 2.3 | 85.6 ± 1.6 |
| 10 | 1.9 | 0.5 | 10 | 6 | 6 | 48.0 ± 2.4 | 78.6 ± 2.3 |
| 14 | 2.1 | 0.3 | 10 | 7 | 6 | 86.0 ± 0.4 | 69.8 ± 5.7 |
| 21 | 2.1 | 9.7 | ND | 225 | 500 | 12.4 ± 1.0 | 0.0 ± 0.2 |
| 24 | 2.3 | 5.6 | ND | 57 | 264 | 24.5 ± 1.9 | 1.1 ± 0.2 |
| 09 | 2.4 | 0.5 | 11 | 7 | 9 | 43.2 ± 15.8 | 74.6 ± 3.2 |
| 11 | 2.6 | 0.3 | 11 | 5 | 6 | 52.7 ± 8.1 | 84.7 ± 1.4 |
| 17 | 3.3 | 5.0 | 30 | 114 | 30 | 4.2 ± 0.2 | 0.7 ± 0.4 |
| 22 | 4.1 | 0.7 | 10 | 4 | 7 | 74.2 ± 7.4 | 44.4 ± 5.3 |
| 16 | 5.1 | 0.3 | 1 | 2 | 3 | 86.0 ± 1.4 | 81.3 ± 1.5 |
| 19 | 6.3 | 2.8 | 9 | 5 | 6 | 79.4 ± 3.5 | 83.8 ± 2.9 |
| 07 | 49.7 | 13.7 | 134 | 65 | 50 | 6.3 ± 3.3 | 2.1 ± 0.7 |
| 13 | 55.7 | 0.2 | 30 | 22 | 23 | 70.4 ± 2.5 | 1.3 ± 0.4 |
| 05 | 69.5 | 1 | 116 | 74 | 74 | 23.8 ± 6.9 | 0.3 ± 0.3 |
| 02 | 69.8 | 0.2 | 42 | 27 | 4 | 80.9 ± 3.6 | 4.6 ± 2.1 |
| 04 | 79.3 | 0.5 | 94 | 62 | 44 | 24.1 ± 4.0 | 0.7 ± 0.8 |
| 03 | 81.9 | 1.1 | 117 | 87 | 63 | 13.1 ± 3.6 | 0.0 ± 0.5 |
| 06 | 86.3 | 0.4 | 39 | 21 | 48 | 45.7 ± 6.4 | 1.4 ± 0.2 |
| 01 | 94.2 | 0.6 | 92 | 91 | 89 | 8.0 ± 1.6 | 0.4 ± 0.4 |
| 23 | 97.2 | 0.4 | 41 | 17 | 37 | 73.7 ± 2.6 | 1.5 ± 0.3 |
| 20 | 143.8 | 4.1 | 98 | 75 | 38 | 31.2 ± 3.9 | 1.1 ± 0.3 |

[1]Tandem Diabodies (TandAbs) are listed in order of increasing CD3 affinity.
[2]CD25 and CD69 induction was measured after 24 hours in unfractionated PBMC cultures.
[3]T cell proliferation induced by CD33/CD3 tandem diabodies in unfractionated PBMC with CD33+ cells present.
[4]Cytotoxicity (%) after 48 hours of DAPI+ cells at a tandem diabodies concentration of 25 pM in the presence of healthy donor T-cells at an E:T cell ratio of 5:1 from 3 independent experiments performed in duplicate wells.
ND: no CD25 activation detectable Example 6

Further Characterization of Tandem Diabodies in Primary Human AML Specimens

For a comprehensive characterization of the cytotoxic properties of these candidates, specimens from AML patients were obtained for the studies from a FHCRC specimen repository.

Frozen aliquots of Ficoll-isolated mononuclear cells from pretreatment ("diagnostic") peripheral blood or bone marrow specimens from adult patients with AML were obtained from repositories at FHCRC. We used the 2008 WHO criteria to define AML (Vardiman et al.; Blood. 2009; 114(5):937-951) and the refined United Kingdom Medical Research Council (MRC) criteria to assign cytogenetic risk (Grimwalde et al.; Blood. 2010; 116(3):354-365). Patients provided written informed consent for the collection and use of their biospecimens for research purposes under protocols approved by the FHCRC Institutional Review Board. Clinical data were de-identified in compliance with Health Insurance Portability and Accountability Act regulations. After thawing, cells were stained with directly labeled antibodies recognizing CD33 (clone P67.6; PE-Cy7-conjugated), CD3 (clone SK7; PerCP-conjugated), CD34 (clone 8G12; APC-conjugated; all from BD Biosciences, San Jose, Calif.), and CD45 (clone HI30; APC-eFluor®780-conjugated; eBioscience). To identify nonviable cells, samples were stained with 4',6-diamidino-2-phenylindole (DAPI). At least 10,000 events were acquired on a Canto II flow cytometer (BD Biosciences), and DAPI-cells analyzed using FlowJo (Tree Star, Ashland, Oreg.).

Figure 7:
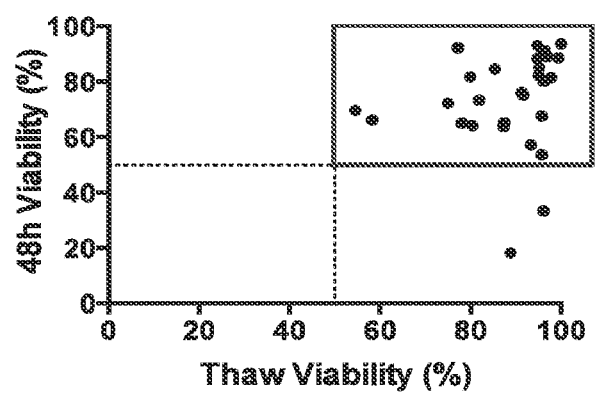
FIG. 7 Selection of primary AML specimens for study. Frozen aliquots from a total of primary human AML specimens were obtained for analysis. The percentage of AML blasts upon thaw was determined by flow cytometry based on CD45/side-scatter properties. Viability of the specimens was determined upon thaw as well after 48 hours in cytokine-containing liquid culture (without addition of tandem diabody molecules or healthy donor T-cells) via flow cytometry using DAPI as live/dead cell marker. Results for viability after thawing as well as after 48 hours are depicted for all specimens, which had >58% AML blasts. Square: Primary AML specimens that showed a viability of >50% at thaw as well as >50% after 48 hours in cytokine-containing liquid culture which were included in the final analyses.

After thawing, specimens had >58% AML blasts, as determined by flow cytometry based on CD45/side-scatter properties. Specimens had >50% viable cells immediately after thawing and >50% viable cells after 48 hours in cytokine-containing liquid culture (FIG. 7). Median age of the patients was 58.1 (range: 23.9-76.2) years; cytogenetic disease risk was favorable in 2, intermediate in 18, and adverse in 7. Information on the mutation status of NPM1, FLT3, and CEBPA was incomplete; however, one sample was known to be CEBPA$^{double-mutant}$, and another sample was NPM1$^{pos}$/FLT3-ITD$^{neg}$. The median percentage of myeloid blasts and CD3$^+$ T-cells in the studied specimens was 86.1% (range: 58.4-97.0%) and 2.0% (range: 0-11.9%), respectively, and the median sample viability after 48 hours in culture was 80.1% (range: 53.6-93.6%). Fifteen of the patients had newly diagnosed AML, whereas 12 either had relapsed (n=7) or refractory (n=5) disease at the time of specimen collection. As summarized in Table 11, basic characteristics of the specimens from patients with newly diagnosed AML were similar to those with relapsed/refractory disease with regard to CD33 expression on myeloid blasts, amount of autologous T-cells, proportion of myeloid blasts, and culture viability.

Figure 8A:
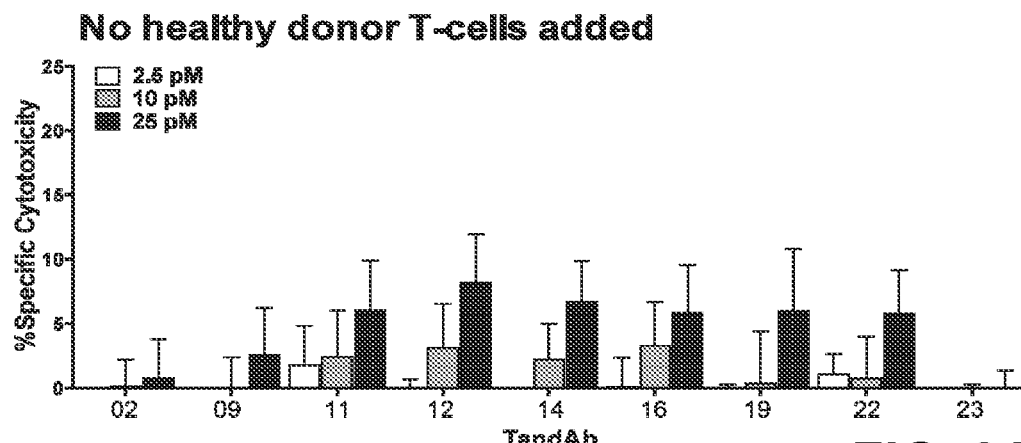
FIG. 8 Tandem diabody-induced cytotoxicity in primary AML specimens. Primary AML specimens were incubated with 2.5 pM (approx. 250 pg/mL), 10 pM (approx. 1 ng/mL), and 25 pM (approx. 2.5 ng/mL) of one of 9 tandem diabody molecules without healthy donor T-cells added (A) or with healthy donor T-cells at an E:T cell ratio of either 1:3 (B) or 1:1 (C) as indicated. After 48 hours, cell counts were determined and cytotoxicity was assessed with DAPI staining to quantify drug-specific cytotoxicity. Results are shown as mean±SEM for the percentage of specific cytotoxicity from experiments performed in duplicate wells.
Figure 8B:
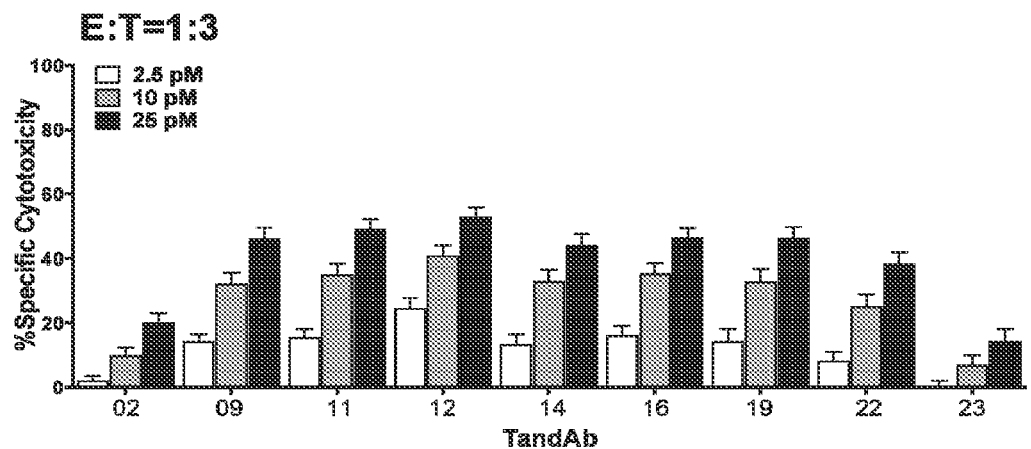
Figure 8C:
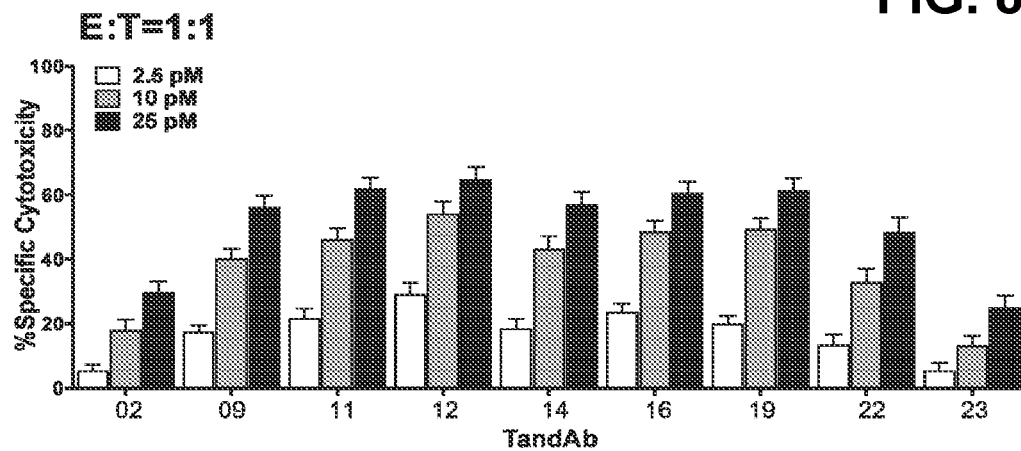

The addition of tandem diabody molecules to AML specimen cultures resulted in modest, dose-dependent cytotoxicity (FIG. 8A), demonstrating that autologous T-cells, contained in the specimens from patients with active AML, can be engaged to lyse leukemic cells. In the presence of healthy donor T-cells, the cytotoxic activity of individual tandem diabodies was strictly dependent on the drug dose and the E:T cell ratio (FIG. 8B/C). However, high activity of tandem diabodies was observed even in some specimens with very low CD33 expression on AML blasts. Among the tandem diabody molecules, 12 appeared to be the most active, since it had the highest cytotoxicity at low concentrations (2.5 pM (approx. 250 ng/mL) and, to a less pronounced degree, also 10 pM (approx. 1 ng/mL)) at both E:T=1:3 and E:T=1:1.

Figure 17:
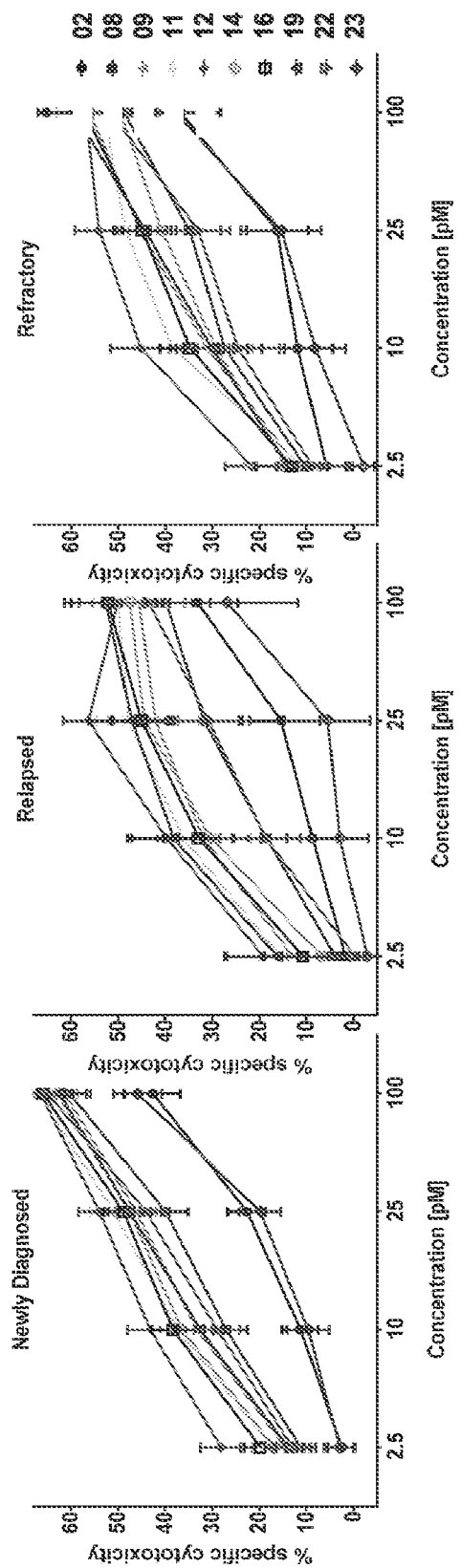
FIG. 17 Cytotoxic activity in newly diagnosed, relapsed and refractory AML patient samples.

The CD33/CD3 tandem diabodies have been screened in representative AML patient blood samples, which varied in terms of patient sex, age, disease stage (newly diagnosed, relapsed, refractory), degree of CD33 expression and cytogenic risk (Table 11). Remarkably, a number of examined tandem diabodies (e.g., 02, 08, 09, 11, 12, 14, 16, 19, 22 and 23) were highly active in nearly all patient samples across the disease spectrum as shown in FIG. 17. Moreover, the extent and scope of activity is similar in all stages of AML, including newly-diagnosed, relapsed and refractory patients.

TABLE 11

Characteristics of primary AML specimens

|  | All patients (n = 27) | Newly diagnosed AML (n = 15) | Relapsed/refractory AML (n = 12) |
|---|---|---|---|
| Median age (range), years | 58.1 (23.9-76.2) | 64.0 (40.2-76.2) | 44.4 (23.9-67.4) |
| Cytogenetic/molecular risk |  |  |  |
| Favorable | 2 | 2 | — |
| Intermediate | 18 | 10 | 8 |
| CEBPA$^{double-mutant}$ | 1 | 1 | — |
| NPM1$^{pos}$/FLT3-ITD$^{neg}$ | 1 | — | 1 |
| NPM1$^{pos}$/FLT3-ITD$^{pos}$ or NPM1$^{neg}$/FLT3-ITD$^{pos}$ | 10 | 5 | 5 |
| Adverse | 7 | 3 | 4 |
| Specimen source |  |  |  |
| Bone marrow | 11 | 4 | 7 |
| Peripheral blood | 16 | 11 | 5 |
| Median % blasts (range) | 86.1 (58.4-97.0) | 86.1 (66.7-95.5) | 86.7 (58.4-97.0) |
| Median CD33 expression on blasts (range) | 849 (5-5, 356) | 849 (5-5, 356) | 788 (7-2, 242) |
| Median % T-cells (range) | 2.0 (0-11.9) | 1.6 (0-11.9) | 2.1 (0.7-8.7) |
| Median % viability at 48 hours (range) | 80.1 (53.6-93.6) | 76.0 (53.6-93.6) | 83.5 (63.9-93.1) |

Example 7

Potency and Efficacy of CD33/CD3 Tandem Diabody 12 and Tandem Diabody 16 on Different CD33$^+$ Cell Lines of Various Origin Expressing Different Levels of CD33

In order to assess whether potency and efficacy of CD33/CD3 tandem diabodies depend on the CD33 density on the target cells, various human CD33$^+$ tumor cell lines and CHO cells expressing recombinant human CD33 were tested for their CD33 expression levels using the QIFIKIT quantification kit and anti-CD33 mAb WM53. The results in Table 12 show that the CD33 densities on the tumor cell lines were in the range between ~1300 SABC (standardized antibody binding capacity) and ~46000 SABC. The expression on CHO-CD33 cells was ~197000 SABC, substantially higher than on the tumor cell lines. All tested CD33$^+$ cell lines were used as target cells in at least 3 independent FACS-based cytotoxicity assays with human T-cells as effector cells at an effector-to-target ratio of 5:1 in the presence of serial dilutions of CD33/CD3 tandem diabody 12 and tandem diabody 16. In each assay EC$_{50}$ and tandem diabody-mediated lysis values were calculated by non-linear regression. The results demonstrate that neither the potency (EC$_{50}$ values) nor the efficacy (% lysis) of 12 and 16 correlates with the CD33 density on the surface of target cells.

Noteworthy, at least 12 and 16 exhibit their cytotoxic activity also against cells like SEM with very low CD33 densities of below 1500 SABC.

TABLE 12

CD33 target cell surface expression and cytotoxic potency of CD33/CD3 tandem diabody 12 and tandem diabody 16:

| Cell line | CD33 density [SABC] | | 12 $EC_{50}$ [pM] | | 16 $EC_{50}$ [pM] | |
|---|---|---|---|---|---|---|
| | mean | SD | mean | SD | mean | SD |
| CHO-CD33 | 196990 | 28053 | 11.8 | 11.2 | 24.0 | 19.5 |
| HL-60 | 45948 | 4478 | 1.4 | 0.5 | 1.6 | 0.4 |
| KG-1 | 42828 | 6923 | 1.0 | 0.6 | 1.9 | 2.0 |
| KASUMI-1 | 25922 | 6484 | 1.3 | 0.6 | 2.4 | 1.4 |
| THP-1 | 22065 | 415 | 1.9 | 0.2 | 6.0 | 1.2 |
| RPMI-8226 | 19931 | 2604 | 14.0 | 17.8 | 2.8 | 2.0 |
| U-937 | 17669 | 4593 | 0.9 | 0.1 | 1.3 | 0.6 |
| K562 | 13789 | 2156 | 4.5 | 1.3 | 4.8 | 2.7 |
| BV-173 | 8518 | 1231 | 1.4 | 0.6 | 3.2 | 1.6 |
| SEM | 1306 | 144.2 | 2.2 | 0.5 | 5.1 | 3.0 |

The standardized antibody binding capacity (SABC) on $CD33^+$ cell lines was determined using QIFIKIT and the anti-CD33 mAb WM53. $EC_{50}$ values for tandem diabody 12 and tandem diabody 16 redirected target cell lysis were determined in FACS-based cytotoxicity assays with human primary T-cells as effector cells at E:T ratios of 5:1 and 20-24 h incubation; assays with CD33-expressing CHO cells were incubated for 40-48 h. Mean and SD of at least 3 independent assays are shown.

Example 8

TandAb-Activation of T-Cells and In Vitro Killing of AML Cells

TandAbs were incubated with purified human T cells and a VPD-450-labeled human $CD33^+$ leukemia cell line, KG-1, or the $CD33^-$ human ALL cell line, G2 (E:T 5:1). Flow cytometry was used to evaluate target cell lysis by TandAbs ($10^{-15}$ to $10^{-8}$M; 24 h, 37° C.).

Incubation of TandAbs 12, 16, and 19 with human T cells efficiently lysed KG-1 cells (IC50 ~0.01, 0.5, and 5 pM respectively). Up to 40% of T cells were activated (CD25+) rising with cytotoxic activity. A control TandAb with an irrelevant target, 00 ($>10^{-7}$ M), did not result in significant killing of KG-1 in vitro. Separately, 16 induced lysis of KG-1 cells (IC50=$5\times10^{-12}$M) while $1\times10^{-8}$M had no effect on CD33-G2 cells. The results indicate thats T cells become activated and potently lyse tumor cells when targeted to CD33+ leukemic cells (KG-1) and primary CD33+ AML blasts by CD33/CD3 TandAbs.

Example 9

Epitope Mapping

Tandem diabodies containing different CD33 binding moieties were subjected to epitope mapping using CLIPS Technology (Pepscan) in order to identify CD33-binding epitopes.

CLIPS Technology facilitates the structuring of peptides into single loops, double-loops, triple loops, sheet-like folds, helix-like folds, and combinations thereof, offering the possibility to map discontinuous epitopes of the target molecule.

An array of more than 7000 independent peptides was synthesized and the binding of each antibody to the peptides was tested in an ELISA.

The tandem diabodies 12, 14, 16 and 22 bind to the stretch $_{62}$DQEVQEETQ$_{70}$ (SEQ ID NO:94) in the first Ig like domain of human CD33. The respective amino acid stretches are shown underlined and in bold in FIGS. 10 and 11. It is contemplated that tandem diabodies 01, 02, 04, 06, 08, 09, 13 and 23 also bind to this epitope as these tandem diabodies share the same CD33 binding domains (SEQ ID NOs:2 and 12, 3 and 13, 5 and 15, 9 and 19) as tandem diabodies 12, 14 16 and 12.

Example 10

Dose-Response in a Prophylactic In Vivo Tumor Model

Tandem diabodies 12 and 16 are compared at different dose levels in a prophylactic HL-60 tumor xenograft model in NOD/scid mice reconstituted with human T-cells. In order to achieve a dose-response three dose levels at 10, 1 and 0.1 μg (0.5, 0.05, and 0.005 mg/kg) were selected.

Eight experimental groups of immunodeficient NOD/scid mice were xenotransplanted by subcutaneous injection with a suspension of $4\times10^6$ HL-60 cells. Prior to injection cells were mixed with $3\times10^6$ T-cells isolated from buffy coats (healthy donors) employing negative selection. To account for potential donor variability of the T-cells, each of the experimental groups was subdivided into three cohorts each receiving T-cells of one individual donor only. All animals of the experimental groups transplanted with tumor cells and T-cells received an intravenous bolus on days 0, 1, 2, 3 and 4 (qdxd5) of either vehicle (control) or 16 or 12 at three different dose levels as indicated (0.1 μg, 1 μg, and 10 μg). One group without effector cells and vehicle treatment served as an additional control. Table 13 summarizes group allocation and dosing schedule.

TABLE 13

| Group | treatment | dose | Cell concentration/animal | Cohort | Schedule (iv) | n |
|---|---|---|---|---|---|---|
| 1 | Vehicle | — | 4 × 106 HL-60 | | | 4 |
| 2 | Vehicle | — | $4 \times 10^6$ HL-60 + $3 \times 10^6$ T-cells | Cohort 1 | Day 0, 1, 2, 3, 4 | 3 |
| | | | $4 \times 10^6$ HL-60 + $3 \times 10^6$ T-cells | Cohort 2 | | 3 |
| | | | $4 \times 10^6$ HL-60 + $3 \times 10^6$ T-cells | Cohort 3 | | 3 |
| 3 | 16 | 10 μg | $4 \times 10^6$ HL-60 + $3 \times 10^6$ T-cells | Cohort 1 | Day 0, 1, 2, 3, 4 | 3 |
| | | | $4 \times 10^6$ HL-60 + $3 \times 10^6$ T-cells | Cohort 2 | | 3 |
| | | | $4 \times 10^6$ HL-60 + $3 \times 10^6$ T-cells | Cohort 3 | | 3 |
| 4 | 16 | 1 μg | $4 \times 10^6$ HL-60 + $3 \times 10^6$ T-cells | Cohort 1 | Day 0, 1, 2, | 3 |
| | | | $4 \times 10^6$ HL-60 + $3 \times 10^6$ T-cells | Cohort 2 | 3, 4 | 3 |
| | | | $4 \times 10^6$ HL-60 + $3 \times 10^6$ T-cells | Cohort 3 | | 3 |

TABLE 13-continued

| Group | treatment | dose | Cell concentration/animal | Cohort | Schedule (iv) | n |
|---|---|---|---|---|---|---|
| 5 | 16 | 0.1 µg | $4 \times 10^6$ HL-60 + $3 \times 10^6$ T-cells | Cohort 1 | Day 0, 1, 2, | 3 |
|   |    |        | $4 \times 10^6$ HL-60 + $3 \times 10^6$ T-cells | Cohort 2 | 3, 4 | 3 |
|   |    |        | $4 \times 10^6$ HL-60 + $3 \times 10^6$ T-cells | Cohort 3 |      | 3 |
| 6 | 12 | 10 µg  | $4 \times 10^6$ HL-60 + $3 \times 10^6$ T-cells | Cohort 1 | Day 0, 1, 2, | 3 |
|   |    |        | $4 \times 10^6$ HL-60 + $3 \times 10^6$ T-cells | Cohort 2 | 3, 4 | 3 |
|   |    |        | $4 \times 10^6$ HL-60 + $3 \times 10^6$ T-cells | Cohort 3 |      | 3 |
| 7 | 12 | 1 µg   | $4 \times 10^6$ HL-60 + $3 \times 10^6$ T-cells | Cohort 1 | Day 0, 1, 2, | 3 |
|   |    |        | $4 \times 10^6$ HL-60 + $3 \times 10^6$ T-cells | Cohort 2 | 3, 4 | 3 |
|   |    |        | $4 \times 10^6$ HL-60 + $3 \times 10^6$ T-cells | Cohort 3 |      | 3 |
| 8 | 12 | 0.1 µg | $4 \times 10^6$ HL-60 + $3 \times 10^6$ T-cells | Cohort 1 | Day 0, 1, 2, | 3 |
|   |    |        | $4 \times 10^6$ HL-60 + $3 \times 10^6$ T-cells | Cohort 2 | 3, 4 | 3 |
|   |    |        | $4 \times 10^6$ HL-60 + $3 \times 10^6$ T-cells | Cohort 3 |      | 3 |

Treatment groups for the in vivo dose-response study in a HL-60 xenograft model. All animals in the control groups reliably developed a tumor and exhibited homogeneous tumor growth. The presence of T-cells had no influence on tumor development. No difference in HL-60 growth was observed in the presence or absence of T-cells in the vehicle-treated control groups.

Figure 12:
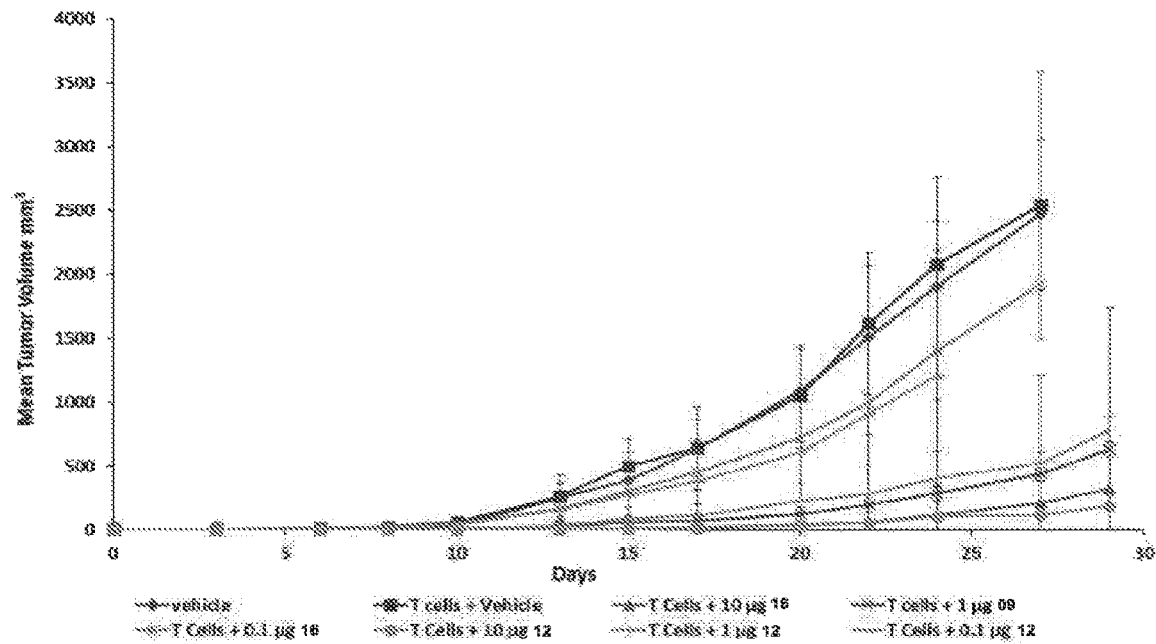
FIG. 12 Effect of tandem diabodies 16 and 12 on the growth of HL-60 cells in NOD/scid mice. Eight experimental groups of immunodeficient NOD/scid mice were xenotransplanted by subcutaneous injection with a suspension of $4 \times 10^6$ HL-60 cells on day 0. Prior to injection HL-60 cells were mixed with $3 \times 10^6$ purified T-cells from healthy donors. All animals of the experimental groups transplanted with tumor cells and T-cells received an intravenous bolus on days 0, 1, 2, 3 and 4 of either vehicle (control) or tandem diabody 16 or 12 at three different dose levels as indicated (0.1 µg, 1 µg, and 10 µg). One group without effector cells and vehicle treatment served as an additional negative control.

Treatment with both test items revealed a clear dose-dependent anti-tumor effect (FIG. 12). No substantial difference was found between the two tandem diabodies. Plotting of mean tumor volumes in FIG. 12 was restricted to day 29 when most of the treatment groups were complete. The study was continued until day 45 and animals were observed for tumor-free survival. In the groups treated with 10 or 1 µg of 16, 6 of 9 animals were tumor-free at the end of the observation period and 5 of 9 animals receiving 10 µg of 12 were tumor-free on day 45. One animal remained tumor-free when treated with 1 µg of 12.

All animals in the control groups reliably developed a tumor and exhibited homogeneous tumor growth. Treatment with either of the tandem diabodies revealed a dose-dependent anti-tumor effect and no substantial difference was found between the two tandem diabodies until day 29.

Detectable differences were observed only after prolonged observation (day 45), at which time the low dose and control groups had already been terminated due to the growth of large tumors. Groups treated with 16 had more tumor-free animals.

Example 11

Established Tumor Model

A xenograft model in NOD/scid mice with pre-established HL-60 tumors employing 16 was developed to demonstrate proof of concept.

In brief, female immune-deficient NOD/scid mice were sub-lethally irradiated (2 Gy) and subcutaneously inoculated with $4 \times 10^6$ HL-60 cells. On day 9 the animals received a single bolus injection of anti-asialo GM1 rabbit antibody (Wako, Neuss, Germany) to deplete murine natural killer (NK) cells. On day 10, when the tumor reached a volume between 50-150 mm³ (mean 73±11 mm³) animals were allocated to 3 treatment groups. Groups 2 and 3 (8 animals each) were intraperitoneally injected with $1.5 \times 10^7$ activated human T-cells. Prior to injection T-cells were isolated from buffy coats (healthy donors) employing negative selection. T-cells were expanded and activated with the T-Cell Activation/Expansion Kit according to the manufacturer's specification (Miltenyi Biotech). In order to address potential donor variability Groups 2 and 3 were subdivided into two cohorts each receiving expanded and activated T-cells from an individual donor. Each cohort received T-cells from one individual T-cell donor only.

TABLE 14

Treatment groups for the established HL-60 xenograft model.

| Group | Animals (n) | Inoculated cells Day 0, sc. | Day 10, ip. | Cohort | Treatment Day 13 to 21, once daily |
|---|---|---|---|---|---|
| 1 | 5 | $4 \times 10^6$ HL-60 |   |   | Vehicle (iv) |
| 2 | 4 | $4 \times 10^6$ HL-60 | $1.5 \times 10^7$ T-cells (Donor 1) | 1 | Vehicle (iv) |
|   | 4 | $4 \times 10^6$ HL-60 | $1.5 \times 10^7$ T-cells (Donor 2) | 2 |   |
| 3 | 4 | $4 \times 10^6$ HL-60 | $1.5 \times 10^7$ T-cells (Donor 1) | 1 | TandAb 16 (iv) 50 µg |
|   | 4 | $4 \times 10^6$ HL-60 | $1.5 \times 10^7$ T-cells (Donor 2) | 2 |   |

Starting on day 13 animals in Group 3 displayed a mean tumor volume of 105 mm³ and were treated with a total of 9 intravenous doses of 50 µg tandem diabody 16 (qdx9d). Table 14 illustrates group allocation and dosing schedule. Groups 1 and 2 were only treated with the vehicle. Body weight and tumor volume were determined until day 27.

Figure 13:
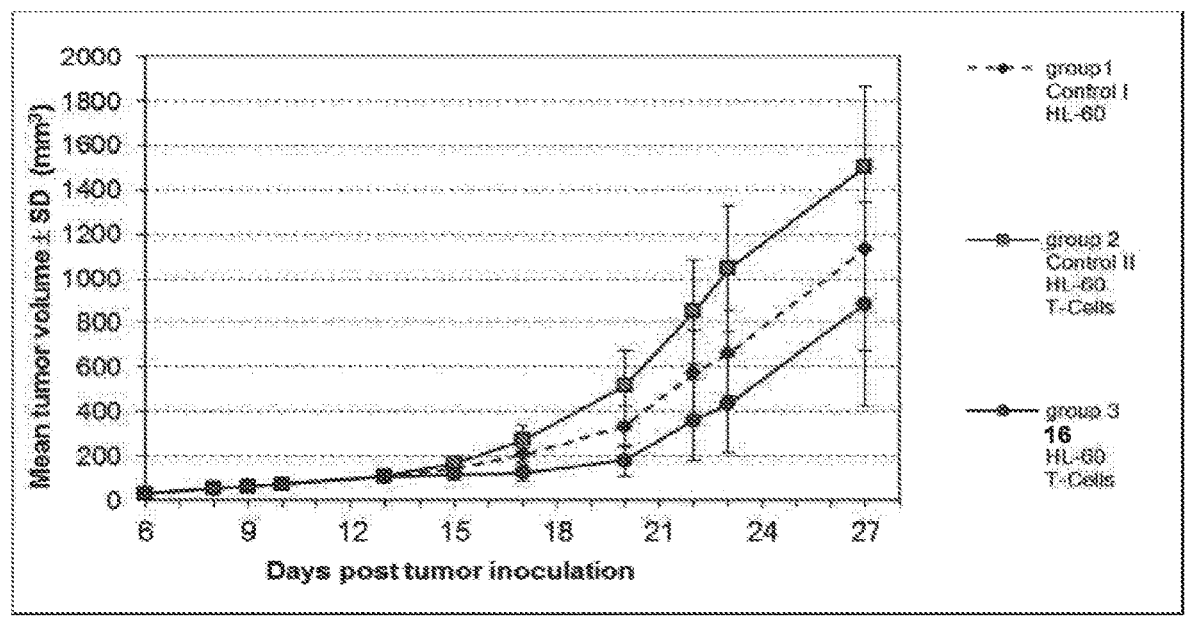
FIG. 13 Anti-tumor activity of tandem diabody 16 in an AML Xenograft Model. NOD/scid mice were sublethally irradiated (2 Gy) and subcutaneously inoculated with $4 \times 10^6$ HL-60 cells. On day 9 the animals received a single bolus injection of anti-asialo GM1 rabbit Ab. When tumors reached a volume between 50-150 mm³ (mean 73±11 mm³) on day 10 animals were allocated to 3 treatment groups. Groups 2 and 3 (n=8) were intraperitoneally injected with $1.5 \times 10^7$ expanded and activated human T-cells. From day 13 to day 21 (qdxd9) animals received either tandem diabody 16 (Group 3) or vehicle into the lateral tail vein (Group 1 and Group 2).

All animals reliably developed a tumor, which was palpable on day 6. The mean tumor volume of vehicle-treated Group 1 and 2 (HL-60) animals continually increased until study termination on day 27 (FIG. 13). In Group 2 animals that received primary activated human T-cells in addition to HL-60 tumor cells, the mean tumor volume increased faster compared to Group 1 (HL-60 only).

Repeated intravenous treatment from days 13 to 21 (qdx9) with tandem diabody 16 (50 µg/animal; 2.5 mg/kg)

in the presence of human T-cells (Group 3) rapidly delayed tumor growth relative to Group 1 and Group 2. Tandem diabody 16 delayed tumor growth in Group 3 by approximately 4-5 days compared to vehicle-treated control group (Group 2). Statistically significant differences in the time period from day 6 to day 27 were identified between Group 2 (HL-60, T-cells, vehicle) and Group 3 (HL-60, T-cells, 16) on day 22 ($p<0.05$), day 23 ($p<0.01$) and day 27 ($p<0.01$) (Two-way Repeated Measures ANOVA with Bonferroni post-tests). No statistically significant differences were present between Group 1 and Group 3 due to unusual slow growth of the tumor in Group 1.

No donor variability with regard to T-cell activity was observed, when comparing tumor development in Cohort 1 and Cohort 2 within a group, which received T-cells from different donors (see Table 14).

Example 10 shows that a xenograft model in NOD/scid mice with a pre-established HL-60 tumor (AML) and intraperitoneally-engrafted human T-cells was successfully developed. Repeated dosing with tandem diabody 16 at a single dose level lead to a statistically significant delay in tumor growth in comparison to the respective vehicle-treated control group. The data generated are comparable to results published for a similar study with a CD33/CD3 BiTE™ (Aigner et al., 2012; Leukemia, 2013, April; 27(5): 1107-15).

Example 12

Efficacy of CD33/CD3 Tandem Diabodies in an AML PDX Model in NSG Mice

Cryopreserved cells from an AML patient whose $CD33^+$ leukemia contained 2-4% $CD3^+$ T-cells were used to establish an AML PDX model in NSG mice. One hour post-injection of tumor cells into irradiated (250 cGy) NSG mice, CD33/CD3 tandem diabodies, 16 or 12, at either of two i.v. doses (50 µg or 5 µg; n=8 mice/group) were injected in a 200 µL bolus. Additional injections of tandem diabodies were performed on each of the following 4 days. Mice were weighed once weekly, and subsequently were sacrificed on day 38 to permit collection of peripheral blood, bone marrow, and spleen for analysis by flow cytometry (huCD33, huCD34, huCD45, muCD45, huCD14, huCD3, huCD4, huCD8, and 7AAD). The results are shown in FIG. 14.

Figure 14A:
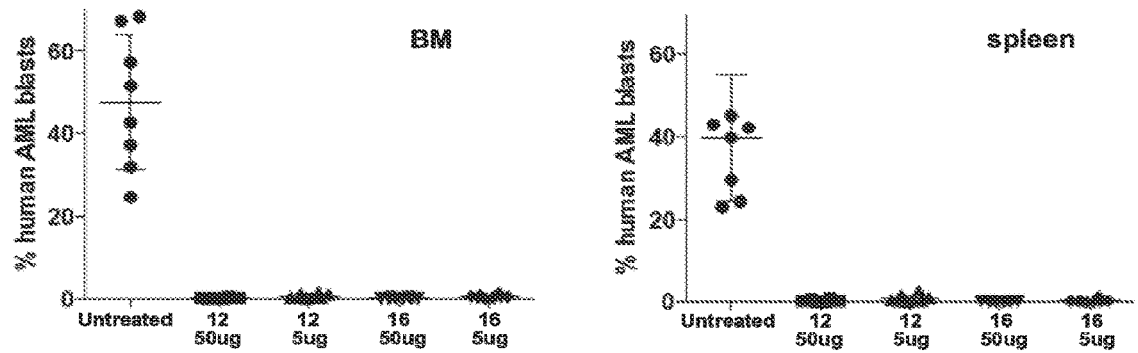
FIG. 14 Relative amount (A) and absolute counts (B) of human AML blasts in the bone marrow (BM) and spleen of NSG mice at day 38 after treatment with 5 µg (0.25 mg/kg) or 50 µg (2.5 mg/kg) CD33/CD3 tandem diabody 12 and 16.
Figure 14B:
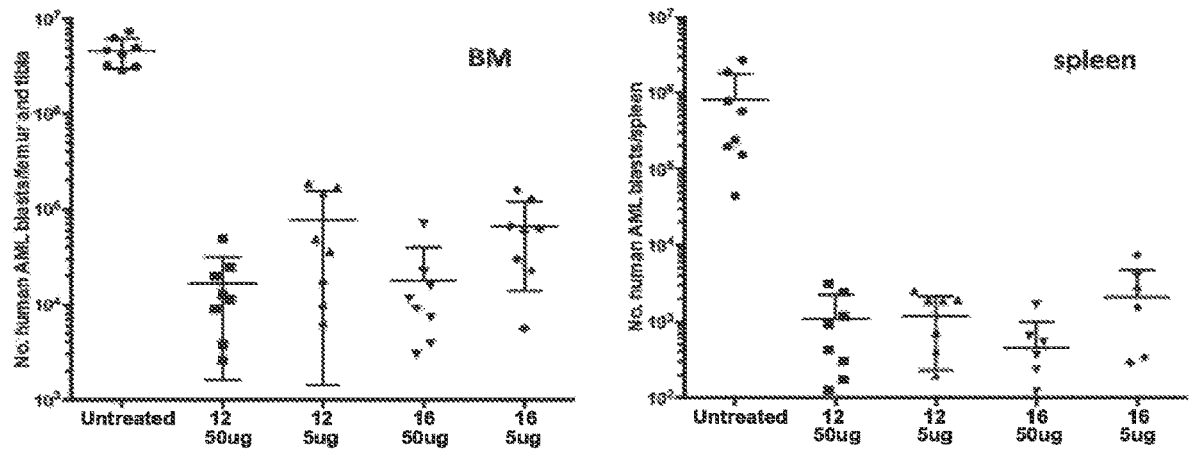

FIG. 14 shows that untreated mice had substantial amounts of human blasts in the bone marrow and spleen after 38 days. In contrast, mice treated with daily i.v. injections of tandem diabodies 12 or 16 exhibited substantially lower numbers of human AML blasts in the bone marrow and in the spleen. The strong anti-AML effect of the CD33/CD3 tandem diabody was observed at both dose levels (5 and 50 µg/injection).

The observed anti-AML effect for both CD33/CD3 tandem diabodies, 12 and 16, was much stronger than the effect of a CD123/CD3 DART® antibody targeting AML in an identical mouse model (Hussaini et al.: "Targeting CD123 In Leukemic Stem Cells Using Dual Affinity Re-Targeting Molecules (DARTS®) Nov. 15, 2013; Blood: 122 (21)). In contrast to the CD33/CD3 tandem diabodies which eliminated nearly all AML blasts in bone marrow and spleen, Hussaini et al. reported that the CD123/CD3 DART® reduced the number of AML blasts in the bone marrow and spleen in the PDX model only by factor 50-1000 at 2.5 and 0.25 mg/kg, the authors further reported that the CD123/CD3 DART™ reduced the number of AML blasts in bone marrow and spleen in the PDX model only by 40-78% at 0.5 mg/kg.

Example 13

Fast Onset of CD33/CD3 Tandem Diabody 16-Mediated Target Cell Lysis

Figure 15:
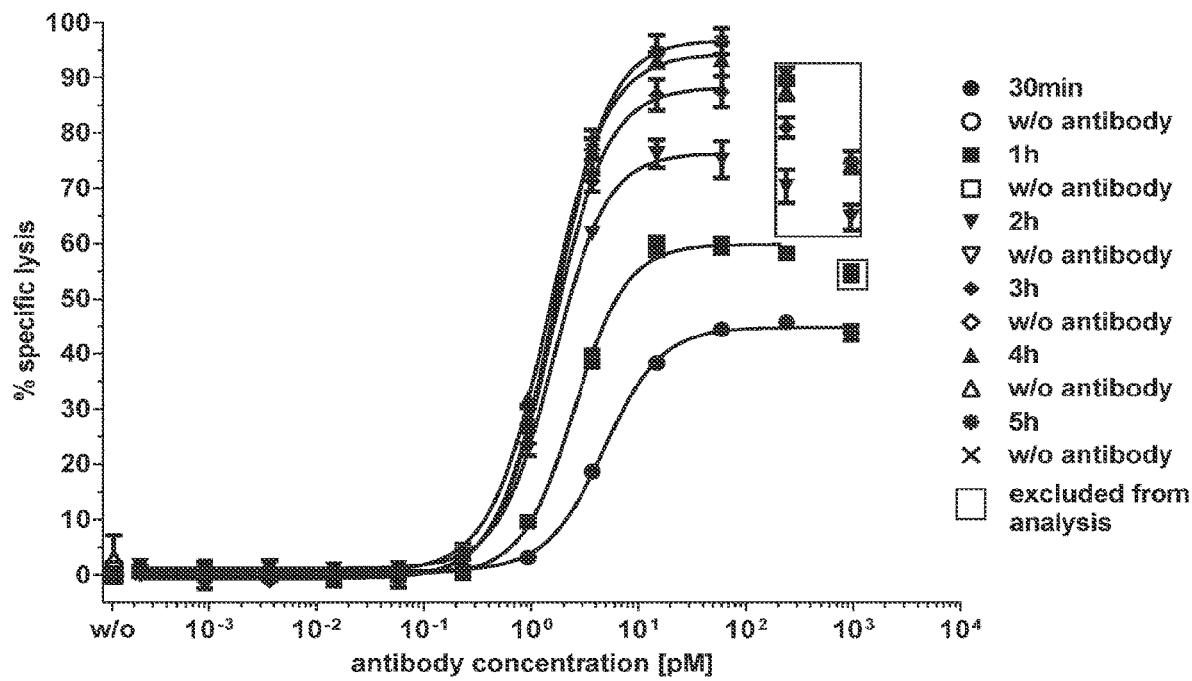
FIG. 15 Kinetics of CD33/CD3 tandem diabody 16-mediated target cell lysis. $1 \times 10^4$ calcein-labeled HL-60 target cells were incubated with primary human T-cells as effector cells at an E:T ratio of 25:1 in the presence of serial dilutions of tandem diabody 16 or without antibody (w/o) for 30 min, 1 h, 2 h, 3 h, 4 h, or 5 h. At each time point, the fluorescent calcein released from lysed target cells was used to calculated specific lysis. Mean and SD of three replicates are plotted.
Figure 16:
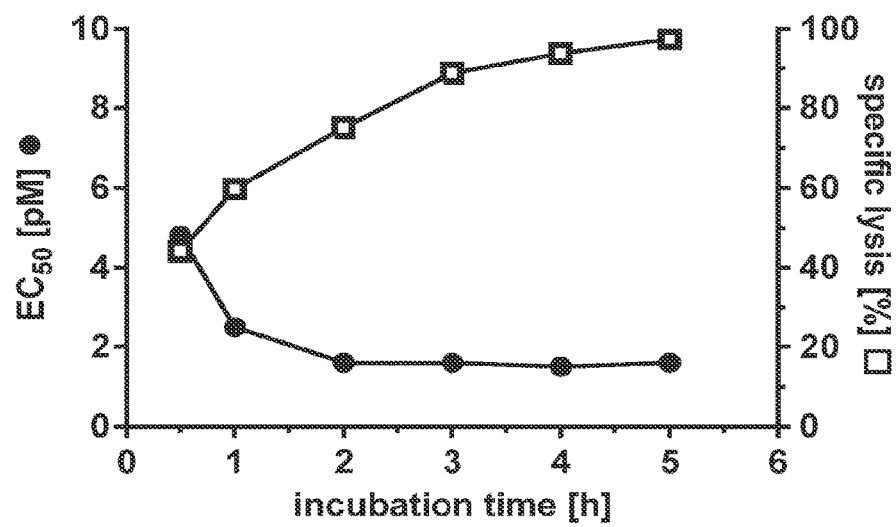
FIG. 16 Kinetics of $EC_{50}$ and specific lysis values for CD33/CD3 tandem diabody 16. $EC_{50}$ values (black solid circles) and tandem diabody 16-mediated target cell lysis (open squares) were determined in calcein-release cytotoxicity assays at the indicated incubation times by non-linear regression/sigmoidal dose-response and plotted.

In order to assess the kinetics of CD33/CD3 tandem diabody-mediated target cell lysis, calcein-release cytotoxicity assays with different incubation times were performed. Calcein-labeled $CD33^+$ HL-60 target cells were incubated with serial dilutions of tandem diabody 16 in the presence of primary human T cells as effector cells at an E:T ratio of 25:1 for 30 min, 1 h, 2 h, 3 h, 4 h, or 5 h. At each time point the calcein that was released from lysed target cells was used to calculate the $EC_{50}$ value and tandem diabody 16-mediated target cell lysis using non-linear regression/sigmoidal dose-response. FIG. 15 shows an unexpected fast onset of tandem diabody-mediated target cells lysis with more than 40% lysis after 30 min incubation at saturating tandem diabody concentrations. After 4 hours incubation more than 90% target cell lysis was reached. Table 15 and FIG. 16 summarize the $EC_{50}$ and specific lysis values determined for tandem diabody 16 at incubation times between 30 min and 5 hours. The results further demonstrate that under the used assay conditions maximal potency (lowest $EC_{50}$ value) was reached after 2 hours incubation and that after 5 hours incubation almost all target cells were lysed. Altogether these results demonstrate a very fast, potent and efficacious target cell lysis mediated by CD33/CD3 tandem diabodies.

TABLE 15

Kinetics of $EC_{50}$ and lysis values determined for tandem diabody 16

| incubation time [min] | $EC_{50}$ [pM] | tandem diabody-mediated lysis [%] |
| --- | --- | --- |
| 30 | 4.8 | 44.1 |
| 60 | 2.5 | 59.8 |
| 120 | 1.6 | 75.1 |
| 180 | 1.6 | 88.8 |
| 240 | 1.5 | 93.7 |
| 300 | 1.6 | 97.4 |

Example 14

Proof-of-Concept Clinical Trial Protocol for Administration of CD33/CD3 Tandem Diabodies to AML Patients This Phase I/II clinical trial for studying CD33/CD3 tandem diabody 16 as a treatment for with acute myeloid leukemia (AML).

Study Outcomes:

Primary: Maximum tolerated dose of CD33/CD3 tandem diabody 16

Secondary: To determine whether in vitro response of CD33/CD3 tandem diabody 16 is associated with clinical response Phase I The maximum tolerated dose (MTD) will be determined in the phase I section of the trial.
  1.1 The maximum tolerated dose (MTD) will be determined in the phase I section of the trial.
  1.2 Patients who fulfill eligibility criteria will be entered into the trial to CD33/CD3 tandem diabody 16.
  1.3 The goal is to identify the highest dose of CD33/CD3 tandem diabody 16 that can be administered safely without severe or unmanageable side effects in participants. The dose given will depend on the number of participants who have been enrolled in the study prior and how well the dose was tolerated. Not all participants will receive the same dose.

Phase II 2.1 A subsequent phase II section will be treated at the MTD with a goal of determining if therapy with therapy of CD33/CD3 tandem diabody 16 results in at least a 20% response rate.

Primary Outcome for the Phase II—To determine if therapy of CD33/CD3 tandem diabody 16 results in at least 20% of patients achieving a clinical response (blast response, minor response, partial response, or complete response)

Eligibility:

Documented AML by peripheral blood and bone marrow analyses meeting WHO criteria, excluding patients with acute promyelocytic leukemia (APL)

Patients with AML refractory to primary induction chemotherapy, relapsed disease, or age ≥60 and not appropriate for standard cytotoxic therapy due to age, performance status, and/or adverse risk factors according to the treating physician Age ≥18 years Karnofsky performance status ≥50% or ECOG performance status 0-2

Life expectancy ≥6 weeks

While certain embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the embodiments. It is intended that the following claims define the scope of the invention and that methods and structures within the scope of these claims and their equivalents be covered thereby.

What is claimed is:

1. A method for the treatment of acute myelogenous leukemia (AML) in a patient having received hematopoietic stem cell transplantation comprising administering a therapeutically effective amount of a homodimeric protein that binds to human CD33 and human CD3,
   wherein the protein comprises a first polypeptide and a second polypeptide, each polypeptide comprising at least four variable chain domains linked one after another, wherein each polypeptide comprises:
   (i) a variable heavy chain (VH) domain specific to human CD33;
   (ii) a variable light chain (VL) domain specific to human CD33;
   (iii) a VH domain specific for human CD3, and
   (iv) a VL domain specific for human CD3,
   linked with one another by peptide linkers L1, L2 and L3 in the order:
   VL(CD3)-L1-VH(CD33)-L2-VL(CD33)-L3-VH(CD3);
   VH(CD3)-L1-VL(CD33)-L2-VH(CD33)-L3-VL(CD3);
   VL(CD33)-L1-VH(CD3)-L2-VL(CD3)-L3-VH(CD33); or
   VH(CD33)-L1-VL(CD3)-L2-VH(CD3)-L3-VL(CD3),
   wherein the VL domain specific to human CD33 comprises a CDR1 consisting of a sequence selected from the group consisting of SEQ ID NOs:21-27, a CDR2 consisting of a sequence selected from the group consisting of SEQ ID NOs:28-34 and a CDR3 consisting of a sequence of the group consisting of SEQ ID NOs: 35-41, and
   wherein the VH domain specific to human CD33 comprises a CDR1 consisting of a sequence selected from the group consisting of SEQ ID NOs:42-48, a CDR2 consisting of a sequence selected from the group consisting of SEQ ID NOs:49-55 and a CDR3 consisting of a sequence selected from the group consisting of SEQ ID NOs:56-63.

2. The method according to claim 1, wherein the transplantation is allogenic.

3. The method according to claim 1, wherein the transplantation is autologous.

4. The method according to claim 1, wherein the patient does not receive a conditioning regimen.

5. The method according to claim 1, further comprising administering a conditioning regimen to the patient.

6. The method according to claim 5, wherein the conditioning regimen is myeloablative.

7. The method according to claim 5, wherein the conditioning regimen is non-myeloablative.

8. The method according to claim 1, wherein the protein is administered at time of progression in allogeneic setting with donor lymphocytes.

9. The method according to claim 1, wherein the protein is administered at time of progression in allogeneic setting without donor lymphocytes.

10. The method according to claim 1, wherein the CDR1, CDR2 and CDR3 of the VL domain specific to human CD33 are sequences selected from the group consisting of:
    (i) SEQ ID NOs: 21, 28 and 35, respectively;

(ii) SEQ ID NOs 22, 29 and 36, respectively;
(iii) SEQ ID NOs: 23, 30 and 37, respectively;
(iv) SEQ ID NOs: 24, 31 and 38, respectively;
(v) SEQ ID NOs: 25, 32 and 39, respectively;
(vi) SEQ ID NOs: 26, 33 and 40, respectively; and
(vii) SEQ ID NOs: 27, 34 and 41, respectively.

11. The method according to claim 1, wherein the CDR1, CDR2 and CDR3 of the VH domain specific to CD33 are sequences selected from the group consisting of:
(i) SEQ ID NOs: 42, 49 and 56, respectively;
(ii) SEQ ID NOs: 43, 50 and 57, respectively;
(iii) SEQ ID NOs: 43, 50 and 58, respectively;
(iv) SEQ ID NOs: 43, 50 and 59, respectively;
(v) SEQ ID NOs: 43, 50 and 60, respectively;
(vi) SEQ ID NOs: 44, 51 and 61, respectively;
(vii) SEQ ID NOs: 45, 52 and 62, respectively;
(viii) SEQ ID NOs: 46, 53 and 63, respectively;
(ix) SEQ ID NOs: 47, 54 and 63, respectively; and
(x) SEQ ID NOs: 48, 55 and 63, respectively.

12. The method according to claim 1, wherein the VL and VH domains specific to CD33 are sequences selected from the group consisting of:
(i) SEQ ID NO: 1 and SEQ ID NO: 11, respectively;
(ii) SEQ ID NO: 2 and SEQ ID NO: 12, respectively;
(iii) SEQ ID NO: 3 and SEQ ID NO: 13, respectively;
(iv) SEQ ID NO: 4 and SEQ ID NO: 14, respectively;
(v) SEQ ID NO: 5 and SEQ ID NO: 15, respectively;
(vi) SEQ ID NO: 6 and SEQ ID NO: 16, respectively;
(vii) SEQ ID NO: 7 and SEQ ID NO: 17, respectively;
(viii) SEQ ID NO: 8 and SEQ ID NO:18, respectively;
(ix) SEQ ID NO: 9 and SEQ ID NO: 19, respectively; and
(x) SEQ ID NO: 10 and SEQ ID NO: 20, respectively.

13. The method according to claim 1, wherein the VH domain specific for human CD3 comprises a CDR1 sequence of STYAMN (SEQ ID NO: 72), a CDR2 sequence of RIRSKYNNYATYYADSVKD (SEQ ID NO: 73) and a CDR3 sequence of HGNFGNSYVSWFAY (SEQ ID NO: 74) or HGNFGNSYVSYFAY (SEQ ID NO: 75).

14. The method according to claim 1, wherein the VL domain specific for human CD3 comprises a CDR1 sequence of RSSTGAVTTSNYAN (SEQ ID NO: 90), a CDR2 sequence of GTNKRAP (SEQ ID NO: 91), and a CDR3 sequence of ALWYSNL (SEQ ID NO: 92).

15. The method according to claim. 1, wherein the VH and VL domains specific to CD3 are sequences selected from the group consisting of:
(i) SEQ ID NO: 64 and SEQ ID NO: 68, respectively;
iii) SEQ ID NO: 65 and SEQ ID NO: 69, respectively;
(iii) SEQ ID NO: 66 and SEQ ID NO: 70, respectively; and
(iv) SEQ ID NO: 67 and SEQ ID NO: 71, respectively.

16. The method according to claim 1, wherein the VH domain specific to human CD33, the VL domain specific to human CD33, the VH domain specific for human CD3, and the VL domain specific for human CD3 are selected from the group consisting of:
(i) SEQ ID NOs: 2, 12, 65 and 69, respectively;
(ii) SEQ ID NOs: 3, 13, 65 and 69, respectively;
(iii) SEQ ID NOs: 4, 14, 65 and 69, respectively;
(iv) SEQ ID NOs: 5, 15, 65 and 69, respectively
(v) SEQ ID NOs: 1, 11, 64 and 68, respectively;
(vi) SEQ ID NOs: 2, 12, 64 and 68, respectively;
(vii) SEQ ID NOs: 2, 12, 66 and 70, respectively;
(viii) SEQ ID NOs: 4, 14, 66 and 70, respectively;
(ix) SEQ ID NOs: 5, 15, 66 and 70, respectively;
(x) SEQ ID NOs: 3, 13, 64 and 63, respectively;
(xi) SEQ ID NOs: 3, 13, 67 and 71, respectively;
(xii) SEQ ID NOs: 4, 14, 64 and 63, respectively;
(xiii) SEQ ID NOs: 5, 15, 64 and 68, respectively;
(xiv) SEQ ID NOs: 7, 17, 64 and 68, respectively;
(xv) SEQ ID NOs: 6, 16, 64 and 68, respectively;
(xvi) SEQ ID NOs: 6, 16, 67 and 71, respectively;
(xvii) SEQ ID NOs: 8, 18, 64 and 68, respectively;
(xviii) SEQ ID NOs: 9, 19, 64 and 68, respectively;
(xix) SEQ ID NOs: 9, 19, 67 and 71, respectively; and
(xx) SEQ ID NOs: 10, 20, 64 and 68, respectively.

17. The method according to claim 1, wherein linkers L1, L2 and L3 consist of 3 to 10 amino acid residues.

18. The method according to claim 1, wherein linkers L1, L2 and L3 are each independently selected from the group consisting of: GGSGGS (SEQ ID NO: 95), GGSG (SEQ ID NO: 96) and GGSGG (SEQ ID NO: 97).

19. The method according to any one of claims 1-7, 8 and 9, wherein each of the first and second polypeptides comprise a sequence selected from the group consisting of SEQ ID NOs: 123-146.

20. The method according to any one of claims 1-7, 8 and 9 wherein each of the first and second polypeptides consist of a sequence selected from the group consisting of SEQ ID NOs: 123-146.

21. The method according to any one of claims 1-7, 8, 9 and 10-17, wherein linkers L1, L2 and L3 consist of 4, 5 or 6 amino acid residues.

* * * * *

UNITED STATES PATENT AND TRADEMARK OFFICE
CERTIFICATE OF CORRECTION

PATENT NO. : 10,738,118 B2
APPLICATION NO. : 15/578185
DATED : August 11, 2020
INVENTOR(S) : Evnin et al.

It is certified that error appears in the above-identified patent and that said Letters Patent is hereby corrected as shown below:

In the Specification

Column 1, Line 9, delete "U.S" and insert --U.S.--

In the Claims

Column 219, Line 63, in Claim 1, delete "SEO" and insert --SEQ--

Column 219, Line 65, in Claim 1, delete "SEO" and insert --SEQ--

Column 219, Line 66, in Claim 1, delete "SEO" and insert --SEQ--

Column 220, Line 41, in Claim 1, delete "SEO" and insert --SEQ--

Column 220, Line 43, in Claim 1, delete "SEO" and insert --SEQ--

Column 221, Line 1, in Claim 10, delete "Nos" and insert --Nos:--

Column 221, Line 45, in Claim 15, delete "claim." and insert --claim--

Column 222, Line 2, in Claim 15, delete "iii)" and insert --(ii)--

Column 222, Line 13, in Claim 16, delete "respectively" and insert --respectively;--

Column 222, Line 19, in Claim 16, delete "63," and insert --68,--

Column 222, Line 21, in Claim 16, delete "63," and insert --68,--

Signed and Sealed this
Twenty-seventh Day of October, 2020

Andrei Iancu
*Director of the United States Patent and Trademark Office*

SEQUENCE LISTING

```
<160> NUMBER OF SEQ ID NOS: 146

<210> SEQ ID NO 1
<211> LENGTH: 108
<212> TYPE: PRT
<213> ORGANISM: Homo sapiens

<400> SEQUENCE: 1

Ser Tyr Glu Leu Thr Gln Pro Pro Ser Val Ser Val Ala Pro Gly Gln
1               5                   10                  15

Thr Ala Met Ile Thr Cys Gly Gly Asn Asn Ile Gly Ser Thr Thr Val
            20                  25                  30

His Trp Tyr Gln Gln Lys Pro Gly Gln Ala Pro Val Leu Val Val Tyr
        35                  40                  45

Asp Asp Asn Glu Arg Pro Ser Gly Ile Pro Glu Arg Phe Ser Gly Ser
    50                  55                  60

Asn Ser Gly Ser Thr Ala Thr Leu Thr Ile Asn Arg Val Glu Ala Gly
65                  70                  75                  80

Asp Glu Ala Asp Tyr Tyr Cys Gln Val Trp Asp Ser Gly Ser Asp His
                85                  90                  95

Val Val Phe Gly Gly Thr Lys Leu Thr Val Leu
                100                 105

<210> SEQ ID NO 2
<211> LENGTH: 110
<212> TYPE: PRT
<213> ORGANISM: Homo sapiens

<400> SEQUENCE: 2

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Asn Gln Arg Pro Ser Gly Val Pro Asp Arg Phe Ser
    50                  55                  60

Gly Ser Lys Ser Gly Ser Ser Ala Ser Leu Ala Ile Ser Gly Leu Gln
65                  70                  75                  80
```

```
Ser Glu Asp Glu Ala Asp Tyr Tyr Cys Ala Thr Trp Asp Asp Ser Leu
                85                  90                  95

Ile Gly Trp Val Phe Gly Gly Gly Thr Lys Leu Thr Val Leu
            100                 105                 110

<210> SEQ ID NO 3
<211> LENGTH: 110
<212> TYPE: PRT
<213> ORGANISM: Homo sapiens

<400> SEQUENCE: 3

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Ile Gly Trp Val Phe Gly Gly Gly Thr Lys Leu Thr Val Leu
            100                 105                 110

<210> SEQ ID NO 4
<211> LENGTH: 110
<212> TYPE: PRT
<213> ORGANISM: Homo sapiens

<400> SEQUENCE: 4

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Ile Gly Trp Val Phe Gly Gly Gly Thr Lys Leu Thr Val Leu
            100                 105                 110

<210> SEQ ID NO 5
<211> LENGTH: 110
<212> TYPE: PRT
<213> ORGANISM: Homo sapiens

<400> SEQUENCE: 5

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30
```

Thr Val Asn Trp Tyr Gln Gln Leu Pro Gly Thr Ala Pro Lys Leu Leu
                35                  40                  45

Ile Tyr Gly Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Thr Trp Asp Asp Ser Leu
                 85                  90                  95

Ile Gly Trp Val Phe Gly Gly Gly Thr Lys Leu Thr Val Leu
                100                 105                 110

<210> SEQ ID NO 6
<211> LENGTH: 110
<212> TYPE: PRT
<213> ORGANISM: Homo sapiens

<400> SEQUENCE: 6

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
                20                  25                  30

Thr Val Asn Trp Tyr Gln Gln Leu Pro Gly Thr Ala Pro Lys Leu Leu
                35                  40                  45

Ile Tyr Ser Asp Asn Gln Arg Pro Ser Gly Val Pro Asp Arg Phe Ser
 50                  55                  60

Gly Ser Lys Ser Gly Ser Ser Ala Ser Leu Ala Ile Ser Gly Leu Gln
 65                  70                  75                  80

Ser Asp Asp Glu Ala Asp Tyr Tyr Cys Ala Thr Trp Asp Asp Ser Leu
                 85                  90                  95

Asn Gly Ala Val Phe Gly Gly Gly Thr Lys Leu Thr Val Leu
                100                 105                 110

<210> SEQ ID NO 7
<211> LENGTH: 111
<212> TYPE: PRT
<213> ORGANISM: Homo sapiens

<400> SEQUENCE: 7

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
                35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Asp Val Val Phe Gly Gly Gly Thr Lys Leu Thr Val Leu
                100                 105                 110

<210> SEQ ID NO 8
<211> LENGTH: 110
<212> TYPE: PRT
<213> ORGANISM: Homo sapiens

<400> SEQUENCE: 8

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Ile Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Lys Gly Tyr Val Phe Gly Gly Gly Thr Lys Leu Thr Val Leu
            100                 105                 110

<210> SEQ ID NO 9
<211> LENGTH: 110
<212> TYPE: PRT
<213> ORGANISM: Homo sapiens

<400> SEQUENCE: 9

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Lys Trp Tyr Gln Gln Leu Pro Gly Thr Ala Pro Lys Leu Leu
            35                  40                  45

Ile Tyr Ser Asn Asn Gln Arg Ser Gly Val Pro Asp Arg Phe Ser
        50                  55                  60

Gly Ser Lys Ser Gly Ser Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Gly Gly Thr Lys Leu Thr Val Leu
            100                 105                 110

<210> SEQ ID NO 10
<211> LENGTH: 110
<212> TYPE: PRT
<213> ORGANISM: Homo sapiens

<400> SEQUENCE: 10

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asp Asn
            20                  25                  30

Val Val Asn Trp Tyr Gln Gln Leu Pro Gly Thr Ala Pro Lys Leu Leu
            35                  40                  45

Ile Tyr Ser Thr Asn Lys Arg Pro Ser Gly Val Pro Asp Arg Phe Ser
        50                  55                  60

Gly Ser Lys Ser Gly Ser Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Ala Tyr Val Phe Gly Gly Gly Thr Lys Leu Thr Val Leu

<210> SEQ ID NO 11
<211> LENGTH: 119
<212> TYPE: PRT
<213> ORGANISM: Homo sapiens

<400> SEQUENCE: 11

Gln Val Gln Leu Gln Glu Ser Gly Gly Val Val Gln Pro Gly Arg
1               5                   10                  15

Ser Leu Arg Leu Ser Cys Ala Ala Ser Gly Phe Ser Phe Ser Asn Tyr
                20                  25                  30

Gly Ile His Trp Val Arg Gln Ala Pro Gly Lys Gly Leu Glu Trp Val
            35                  40                  45

Ala Leu Ile Ser Tyr Asp Gly Asn Lys Lys Phe Tyr Ala Asp Ser Val
        50                  55                  60

Lys Gly Arg Phe Ala Ile Ser Arg Asp Thr Ser Lys Asn Thr Val Asp
65                  70                  75                  80

Leu Gln Met Thr Ser Leu Arg Pro Glu Asp Thr Ala Val Tyr Tyr Cys
                85                  90                  95

Ala Lys Asp Arg Leu Glu Ser Ala Ala Phe Asp Tyr Trp Gly Gln Gly
            100                 105                 110

Thr Leu Val Thr Val Ser Ser
        115

<210> SEQ ID NO 12
<211> LENGTH: 122
<212> TYPE: PRT
<213> ORGANISM: Homo sapiens

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Pro Gly Gln Gly Leu Glu Trp Met
            35                  40                  45

Gly Trp Met Asn Pro Asn Ser Gly Asn Thr Gly Phe Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Ala Asn Thr Asp Phe Ser Tyr Gly Met Asp Val Trp
            100                 105                 110

Gly Gln Gly Thr Leu Val Thr Val Ser Ser
        115                 120

<210> SEQ ID NO 13
<211> LENGTH: 122
<212> TYPE: PRT
<213> ORGANISM: Homo sapiens

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Pro Gly Gln Gly Leu Glu Trp Met
            35                  40                  45

Gly Trp Met Asn Pro Asn Ser Gly Asn Thr Gly Phe Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Ala Val Thr Asp Tyr Tyr Tyr Gly Met Asp Val Trp
                100                 105                 110

Gly Gln Gly Thr Leu Val Thr Val Ser Ser
            115                 120

<210> SEQ ID NO 14
<211> LENGTH: 122
<212> TYPE: PRT
<213> ORGANISM: Homo sapiens

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Pro Gly Gln Gly Leu Glu Trp Met
            35                  40                  45

Gly Trp Met Asn Pro Asn Ser Gly Asn Thr Gly Phe Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Ala Asn Thr Asp Tyr Ser Phe Gly Met Asp Val Trp
                100                 105                 110

Gly Gln Gly Thr Leu Val Thr Val Ser Ser
            115                 120

<210> SEQ ID NO 15
<211> LENGTH: 122
<212> TYPE: PRT
<213> ORGANISM: Homo sapiens

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Pro Gly Gln Gly Leu Glu Trp Met
            35                  40                  45

Gly Trp Met Asn Pro Asn Ser Gly Asn Thr Gly Phe Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Ala Asn Thr Asp Tyr Ser Leu Gly Met Asp Val Trp
                100                 105                 110

```
Gly Gln Gly Thr Leu Val Thr Val Ser Ser
        115                 120

<210> SEQ ID NO 16
<211> LENGTH: 123
<212> TYPE: PRT
<213> ORGANISM: Homo sapiens

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Val Val Pro Ala Ala Ile Asp Tyr Tyr Gly Met Asp Val
            100                 105                 110

Trp Gly Gln Gly Thr Thr Val Thr Val Ser Ser
        115                 120

<210> SEQ ID NO 17
<211> LENGTH: 119
<212> TYPE: PRT
<213> ORGANISM: Homo sapiens

<400> SEQUENCE: 17

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Lys Arg Gly Ser Asp Ala Phe Asp Ile Trp Gly Gln Gly
            100                 105                 110

Thr Thr Val Thr Val Ser Ser
        115

<210> SEQ ID NO 18
<211> LENGTH: 122
<212> TYPE: PRT
<213> ORGANISM: Homo sapiens

<400> SEQUENCE: 18

Gln Val Gln Leu Val Gln Ser Gly Ala Glu Val Lys Lys Pro Gly Ser
1               5                   10                  15
```

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Tyr Pro Ile Phe Gly Ser Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Tyr Asp Ser Ser Glu Trp Ala Phe Asp Ile Trp
            100                 105                 110

Gly Gln Gly Thr Leu Val Thr Val Ser Ser
            115                 120

<210> SEQ ID NO 19
<211> LENGTH: 122
<212> TYPE: PRT
<213> ORGANISM: Homo sapiens

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Ser Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Tyr Asp Ser Ser Glu Trp Ala Phe Asp Ile Trp
            100                 105                 110

Gly Gln Gly Thr Leu Val Thr Val Ser Ser
            115                 120

<210> SEQ ID NO 20
<211> LENGTH: 122
<212> TYPE: PRT
<213> ORGANISM: Homo sapiens

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asp Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Ser Ala His Tyr Ser Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Glu Tyr Tyr Asp Ser Ser Glu Trp Ala Phe Asp Ile Trp
            100                 105                 110

Gly Gln Gly Thr Leu Val Thr Val Ser Ser
        115                 120

<210> SEQ ID NO 21
<211> LENGTH: 11
<212> TYPE: PRT
<213> ORGANISM: Homo sapiens

<400> SEQUENCE: 21

Gly Gly Asn Asn Ile Gly Ser Thr Thr Val His
1               5                   10

<210> SEQ ID NO 22
<211> LENGTH: 13
<212> TYPE: PRT
<213> ORGANISM: Homo sapiens

<400> SEQUENCE: 22

Ser Gly Ser Arg Ser Asn Ile Gly Ser Asn Thr Val Asn
1               5                   10

<210> SEQ ID NO 23
<211> LENGTH: 13
<212> TYPE: PRT
<213> ORGANISM: Homo sapiens

<400> SEQUENCE: 23

Ser Gly Ser Ser Ser Asn Ile Gly Ser Asn Thr Val Asn
1               5                   10

<210> SEQ ID NO 24
<211> LENGTH: 14
<212> TYPE: PRT
<213> ORGANISM: Homo sapiens

<400> SEQUENCE: 24

Thr Gly Ser Ser Ser Asn Ile Gly Ala Gly Tyr Asp Val His
1               5                   10

<210> SEQ ID NO 25
<211> LENGTH: 13
<212> TYPE: PRT
<213> ORGANISM: Homo sapiens

<400> SEQUENCE: 25

Ser Gly Ser Ser Ser Asn Ile Gly Ser Asn Ile Val Asn
1               5                   10

<210> SEQ ID NO 26
<211> LENGTH: 13
<212> TYPE: PRT
<213> ORGANISM: Homo sapiens

<400> SEQUENCE: 26

Ser Gly Ser Ser Ser Asn Ile Gly Ser Asn Thr Val Lys
1               5                   10

<210> SEQ ID NO 27
<211> LENGTH: 13
<212> TYPE: PRT
<213> ORGANISM: Homo sapiens

<400> SEQUENCE: 27
```

Ser Gly Ser Ser Ser Asn Ile Gly Asp Asn Val Val Asn
1               5                   10

<210> SEQ ID NO 28
<211> LENGTH: 7
<212> TYPE: PRT
<213> ORGANISM: Homo sapiens

<400> SEQUENCE: 28

Asp Asp Asn Glu Arg Pro Ser
1               5

<210> SEQ ID NO 29
<211> LENGTH: 7
<212> TYPE: PRT
<213> ORGANISM: Homo sapiens

<400> SEQUENCE: 29

Gly Asn Asn Gln Arg Pro Ser
1               5

<210> SEQ ID NO 30
<211> LENGTH: 7
<212> TYPE: PRT
<213> ORGANISM: Homo sapiens

<400> SEQUENCE: 30

Ser Asp Asn Gln Arg Pro Ser
1               5

<210> SEQ ID NO 31
<211> LENGTH: 7
<212> TYPE: PRT
<213> ORGANISM: Homo sapiens

<400> SEQUENCE: 31

Gly Asn Ser Asn Arg Pro Ser
1               5

<210> SEQ ID NO 32
<211> LENGTH: 7
<212> TYPE: PRT
<213> ORGANISM: Homo sapiens

<400> SEQUENCE: 32

Ser Asn Asn Gln Arg Pro Ser
1               5

<210> SEQ ID NO 33
<211> LENGTH: 7
<212> TYPE: PRT
<213> ORGANISM: Homo sapiens

<400> SEQUENCE: 33

Ser Asn Asn Gln Arg Ser Ser
1               5

<210> SEQ ID NO 34
<211> LENGTH: 7
<212> TYPE: PRT
<213> ORGANISM: Homo sapiens

<400> SEQUENCE: 34

Ser Thr Asn Lys Arg Pro Ser

```
<210> SEQ ID NO 35
<211> LENGTH: 9
<212> TYPE: PRT
<213> ORGANISM: Homo sapiens

<400> SEQUENCE: 35

Gln Val Trp Asp Ser Gly Ser Asp His
1               5

<210> SEQ ID NO 36
<211> LENGTH: 9
<212> TYPE: PRT
<213> ORGANISM: Homo sapiens

<400> SEQUENCE: 36

Ala Thr Trp Asp Asp Ser Leu Ile Gly
1               5

<210> SEQ ID NO 37
<211> LENGTH: 9
<212> TYPE: PRT
<213> ORGANISM: Homo sapiens

<400> SEQUENCE: 37

Ala Thr Trp Asp Asp Ser Leu Asn Gly
1               5

<210> SEQ ID NO 38
<211> LENGTH: 9
<212> TYPE: PRT
<213> ORGANISM: Homo sapiens

<400> SEQUENCE: 38

Gln Ser Tyr Asp Ser Ser Leu Ser Asp
1               5

<210> SEQ ID NO 39
<211> LENGTH: 9
<212> TYPE: PRT
<213> ORGANISM: Homo sapiens

<400> SEQUENCE: 39

Ala Ala Trp Asp Asp Ser Leu Lys Gly
1               5

<210> SEQ ID NO 40
<211> LENGTH: 9
<212> TYPE: PRT
<213> ORGANISM: Homo sapiens

<400> SEQUENCE: 40

Ala Ala Trp Asp Asp Ser Leu Asn Gly
1               5

<210> SEQ ID NO 41
<211> LENGTH: 9
<212> TYPE: PRT
<213> ORGANISM: Homo sapiens

<400> SEQUENCE: 41

Ala Ala Trp Asp Asp Ser Leu Ser Ala
1               5
```

<210> SEQ ID NO 42
<211> LENGTH: 6
<212> TYPE: PRT
<213> ORGANISM: Homo sapiens

<400> SEQUENCE: 42

Ser Asn Tyr Gly Ile His
1               5

<210> SEQ ID NO 43
<211> LENGTH: 6
<212> TYPE: PRT
<213> ORGANISM: Homo sapiens

<400> SEQUENCE: 43

Thr Ser Tyr Asp Ile Asn
1               5

<210> SEQ ID NO 44
<211> LENGTH: 6
<212> TYPE: PRT
<213> ORGANISM: Homo sapiens

<400> SEQUENCE: 44

Thr Ser Tyr Tyr Met His
1               5

<210> SEQ ID NO 45
<211> LENGTH: 6
<212> TYPE: PRT
<213> ORGANISM: Homo sapiens

<400> SEQUENCE: 45

Thr Ser Tyr Trp Ile Gly
1               5

<210> SEQ ID NO 46
<211> LENGTH: 6
<212> TYPE: PRT
<213> ORGANISM: Homo sapiens

<400> SEQUENCE: 46

Ser Ser Tyr Ala Ile Ser
1               5

<210> SEQ ID NO 47
<211> LENGTH: 6
<212> TYPE: PRT
<213> ORGANISM: Homo sapiens

<400> SEQUENCE: 47

Ser Ser Tyr Gly Ile Ser
1               5

<210> SEQ ID NO 48
<211> LENGTH: 6
<212> TYPE: PRT
<213> ORGANISM: Homo sapiens

<400> SEQUENCE: 48

Asp Ser Tyr Ala Ile Ser
1               5

<210> SEQ ID NO 49

<211> LENGTH: 17
<212> TYPE: PRT
<213> ORGANISM: Homo sapiens

<400> SEQUENCE: 49

Leu Ile Ser Tyr Asp Gly Asn Lys Lys Phe Tyr Ala Asp Ser Val Lys
1               5                   10                  15
Gly

<210> SEQ ID NO 50
<211> LENGTH: 17
<212> TYPE: PRT
<213> ORGANISM: Homo sapiens

<400> SEQUENCE: 50

Trp Met Asn Pro Asn Ser Gly Asn Thr Gly Phe Ala Gln Lys Phe Gln
1               5                   10                  15
Gly

<210> SEQ ID NO 51
<211> LENGTH: 18
<212> TYPE: PRT
<213> ORGANISM: Homo sapiens

<400> SEQUENCE: 51

Gly Ile Ile Asn Pro Ser Gly Gly Ser Thr Ser Tyr Ala Gln Lys Phe
1               5                   10                  15
Gln Gly

<210> SEQ ID NO 52
<211> LENGTH: 17
<212> TYPE: PRT
<213> ORGANISM: Homo sapiens

<400> SEQUENCE: 52

Ile Ile Tyr Pro Gly Asp Ser Asp Thr Arg Tyr Ser Pro Ser Phe Gln
1               5                   10                  15
Gly

<210> SEQ ID NO 53
<211> LENGTH: 17
<212> TYPE: PRT
<213> ORGANISM: Homo sapiens

<400> SEQUENCE: 53

Gly Ile Tyr Pro Ile Phe Gly Ser Ala Asn Tyr Ala Gln Lys Phe Gln
1               5                   10                  15
Gly

<210> SEQ ID NO 54
<211> LENGTH: 17
<212> TYPE: PRT
<213> ORGANISM: Homo sapiens

<400> SEQUENCE: 54

Gly Ile Ile Pro Ile Phe Gly Ser Ala His Tyr Ala Gln Lys Phe Gln
1               5                   10                  15
Gly

<210> SEQ ID NO 55
<211> LENGTH: 17

```
<212> TYPE: PRT
<213> ORGANISM: Homo sapiens

<400> SEQUENCE: 55

Gly Ile Ile Pro Ile Phe Gly Ser Ala His Tyr Ser Gln Lys Phe Gln
1               5                   10                  15
Gly

<210> SEQ ID NO 56
<211> LENGTH: 10
<212> TYPE: PRT
<213> ORGANISM: Homo sapiens

<400> SEQUENCE: 56

Asp Arg Leu Glu Ser Ala Ala Phe Asp Tyr
1               5                   10

<210> SEQ ID NO 57
<211> LENGTH: 13
<212> TYPE: PRT
<213> ORGANISM: Homo sapiens

<400> SEQUENCE: 57

Asp Arg Ala Asn Thr Asp Phe Ser Tyr Gly Met Asp Val
1               5                   10

<210> SEQ ID NO 58
<211> LENGTH: 13
<212> TYPE: PRT
<213> ORGANISM: Homo sapiens

<400> SEQUENCE: 58

Asp Arg Ala Val Thr Asp Tyr Tyr Tyr Gly Met Asp Val
1               5                   10

<210> SEQ ID NO 59
<211> LENGTH: 13
<212> TYPE: PRT
<213> ORGANISM: Homo sapiens

<400> SEQUENCE: 59

Asp Arg Ala Asn Thr Asp Tyr Ser Phe Gly Met Asp Val
1               5                   10

<210> SEQ ID NO 60
<211> LENGTH: 13
<212> TYPE: PRT
<213> ORGANISM: Homo sapiens

<400> SEQUENCE: 60

Asp Arg Ala Asn Thr Asp Tyr Ser Leu Gly Met Asp Val
1               5                   10

<210> SEQ ID NO 61
<211> LENGTH: 14
<212> TYPE: PRT
<213> ORGANISM: Homo sapiens

<400> SEQUENCE: 61

Asp Val Val Pro Ala Ala Ile Asp Tyr Tyr Gly Met Asp Val
1               5                   10

<210> SEQ ID NO 62
<211> LENGTH: 10
```

```
<212> TYPE: PRT
<213> ORGANISM: Homo sapiens

<400> SEQUENCE: 62

His Lys Arg Gly Ser Asp Ala Phe Asp Ile
1               5                   10

<210> SEQ ID NO 63
<211> LENGTH: 13
<212> TYPE: PRT
<213> ORGANISM: Homo sapiens

<400> SEQUENCE: 63

Glu Tyr Tyr Tyr Asp Ser Ser Glu Trp Ala Phe Asp Ile
1               5                   10

<210> SEQ ID NO 64
<211> LENGTH: 125
<212> TYPE: PRT
<213> ORGANISM: Homo sapiens

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Tyr Phe
            100                 105                 110

Ala Tyr Trp Gly Gln Gly Thr Leu Val Thr Val Ser Ser
        115                 120                 125

<210> SEQ ID NO 65
<211> LENGTH: 125
<212> TYPE: PRT
<213> ORGANISM: Homo sapiens

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110
```

```
Ala Tyr Trp Gly Gln Gly Thr Leu Val Thr Val Ser Ser
            115                 120                 125

<210> SEQ ID NO 66
<211> LENGTH: 125
<212> TYPE: PRT
<213> ORGANISM: Homo sapiens

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 67
<211> LENGTH: 125
<212> TYPE: PRT
<213> ORGANISM: Homo sapiens

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 68
<211> LENGTH: 110
<212> TYPE: PRT
<213> ORGANISM: Homo sapiens

<400> SEQUENCE: 68

Asp Ile Gln Met Thr Gln Ser Pro Ser Ser Leu Ser Ala Ser Val Gly
1               5                   10                  15
```

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
            35                  40                  45

Ala Leu Ile Gly Gly Thr Asn Lys Arg Ala Pro Gly Val Pro Ser Arg
50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
            85                  90                  95

Asn Leu Trp Val Phe Gly Gln Gly Thr Lys Val Glu Ile Lys
            100                 105                 110

<210> SEQ ID NO 69
<211> LENGTH: 110
<212> TYPE: PRT
<213> ORGANISM: Homo sapiens

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
            35                  40                  45

Gly Leu Ile Gly Gly Thr Asn Lys Arg Ala Pro Gly Val Pro Ala Arg
50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
            85                  90                  95

Asn Leu Trp Val Phe Gly Gln Gly Thr Lys Val Glu Ile Lys
            100                 105                 110

<210> SEQ ID NO 70
<211> LENGTH: 110
<212> TYPE: PRT
<213> ORGANISM: Homo sapiens

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
            35                  40                  45

Gly Leu Ile Gly Gly Thr Asn Lys Arg Ala Pro Gly Val Pro Ser Arg
50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
            85                  90                  95

Asn Leu Trp Val Phe Gly Gln Gly Thr Lys Val Glu Ile Lys
            100                 105                 110

<210> SEQ ID NO 71
<211> LENGTH: 110

```
<212> TYPE: PRT
<213> ORGANISM: Homo sapiens

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ser Arg
    50                  55                  60

Phe Ser Gly Ser Leu Ile Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys
            100                 105                 110

<210> SEQ ID NO 72
<211> LENGTH: 6
<212> TYPE: PRT
<213> ORGANISM: Homo sapiens

<400> SEQUENCE: 72

Ser Thr Tyr Ala Met Asn
1               5

<210> SEQ ID NO 73
<211> LENGTH: 19
<212> TYPE: PRT
<213> ORGANISM: Homo sapiens

<400> SEQUENCE: 73

Arg Ile Arg Ser Lys Tyr Asn Asn Tyr Ala Thr Tyr Tyr Ala Asp Ser
1               5                   10                  15

Val Lys Asp

<210> SEQ ID NO 74
<211> LENGTH: 14
<212> TYPE: PRT
<213> ORGANISM: Homo sapiens

<400> SEQUENCE: 74

His Gly Asn Phe Gly Asn Ser Tyr Val Ser Trp Phe Ala Tyr
1               5                   10

<210> SEQ ID NO 75
<211> LENGTH: 14
<212> TYPE: PRT
<213> ORGANISM: Homo sapiens

<400> SEQUENCE: 75

His Gly Asn Phe Gly Asn Ser Tyr Val Ser Tyr Phe Ala Tyr
1               5                   10

<210> SEQ ID NO 76
<211> LENGTH: 6
<212> TYPE: PRT
<213> ORGANISM: Homo sapiens

<400> SEQUENCE: 76
```

```
Asn Thr Tyr Ala Met Asn
1               5
```

<210> SEQ ID NO 77
<211> LENGTH: 6
<212> TYPE: PRT
<213> ORGANISM: Homo sapiens

<400> SEQUENCE: 77

```
Asn Thr Tyr Ala Met His
1               5
```

<210> SEQ ID NO 78
<211> LENGTH: 6
<212> TYPE: PRT
<213> ORGANISM: Homo sapiens

<400> SEQUENCE: 78

```
Asn Lys Tyr Ala Met Asn
1               5
```

<210> SEQ ID NO 79
<211> LENGTH: 19
<212> TYPE: PRT
<213> ORGANISM: Homo sapiens

<400> SEQUENCE: 79

```
Arg Ile Arg Asn Lys Tyr Asn Asn Tyr Ala Thr Tyr Ala Asp Ser
1               5                   10                  15

Val Lys Asp
```

<210> SEQ ID NO 80
<211> LENGTH: 19
<212> TYPE: PRT
<213> ORGANISM: Homo sapiens

<400> SEQUENCE: 80

```
Arg Ile Arg Asn Lys Tyr Asn Asn Tyr Ala Thr Glu Tyr Ala Asp Ser
1               5                   10                  15

Val Lys Asp
```

<210> SEQ ID NO 81
<211> LENGTH: 19
<212> TYPE: PRT
<213> ORGANISM: Homo sapiens

<400> SEQUENCE: 81

```
Arg Ile Arg Ser Lys Tyr Asn Asn Tyr Ala Thr Glu Tyr Ala Ala Ser
1               5                   10                  15

Val Lys Asp
```

<210> SEQ ID NO 82
<211> LENGTH: 19
<212> TYPE: PRT
<213> ORGANISM: Homo sapiens

<400> SEQUENCE: 82

```
Arg Ile Arg Asn Lys Tyr Asn Asn Tyr Ala Thr Glu Tyr Ala Ala Ser
1               5                   10                  15

Val Lys Asp
```

```
<210> SEQ ID NO 83
<211> LENGTH: 19
<212> TYPE: PRT
<213> ORGANISM: Homo sapiens

<400> SEQUENCE: 83

Arg Ile Arg Ser Lys Tyr Asn Asn Tyr Ala Thr Tyr Tyr Ala Asp Ser
1               5                   10                  15

Val Lys Gly

<210> SEQ ID NO 84
<211> LENGTH: 19
<212> TYPE: PRT
<213> ORGANISM: Homo sapiens

<400> SEQUENCE: 84

Arg Ile Arg Ser Lys Tyr Asn Asn Tyr Ala Thr Glu Tyr Ala Asp Ser
1               5                   10                  15

Val Lys Ser

<210> SEQ ID NO 85
<211> LENGTH: 14
<212> TYPE: PRT
<213> ORGANISM: Homo sapiens

<400> SEQUENCE: 85

His Gly Asn Phe Gly Asp Ser Tyr Val Ser Trp Phe Ala Tyr
1               5                   10

<210> SEQ ID NO 86
<211> LENGTH: 14
<212> TYPE: PRT
<213> ORGANISM: Homo sapiens

<400> SEQUENCE: 86

His Gly Asn Phe Gly Asn Thr Tyr Val Ser Trp Phe Ala Tyr
1               5                   10

<210> SEQ ID NO 87
<211> LENGTH: 14
<212> TYPE: PRT
<213> ORGANISM: Homo sapiens

<400> SEQUENCE: 87

His Gly Asn Phe Gly Cys Ser Tyr Val Ser Trp Phe Ala Tyr
1               5                   10

<210> SEQ ID NO 88
<211> LENGTH: 14
<212> TYPE: PRT
<213> ORGANISM: Homo sapiens

<400> SEQUENCE: 88

His Gly Asn Phe Gly Asn Ser Tyr Ile Ser Tyr Trp Ala Tyr
1               5                   10

<210> SEQ ID NO 89
<211> LENGTH: 14
<212> TYPE: PRT
<213> ORGANISM: Homo sapiens

<400> SEQUENCE: 89

His Gly Asn Phe Gly Asn Ser Tyr Val Ser Phe Phe Ala Tyr
1               5                   10
```

<210> SEQ ID NO 90
<211> LENGTH: 14
<212> TYPE: PRT
<213> ORGANISM: Homo sapiens

<400> SEQUENCE: 90

Arg Ser Ser Thr Gly Ala Val Thr Thr Ser Asn Tyr Ala Asn
1               5                   10

<210> SEQ ID NO 91
<211> LENGTH: 7
<212> TYPE: PRT
<213> ORGANISM: Homo sapiens

<400> SEQUENCE: 91

Gly Thr Asn Lys Arg Ala Pro
1               5

<210> SEQ ID NO 92
<211> LENGTH: 7
<212> TYPE: PRT
<213> ORGANISM: Homo sapiens

<400> SEQUENCE: 92

Ala Leu Trp Tyr Ser Asn Leu
1               5

<210> SEQ ID NO 93
<211> LENGTH: 242
<212> TYPE: PRT
<213> ORGANISM: Homo sapiens

<400> SEQUENCE: 93

Asp Pro Asn Phe Trp Leu Gln Val Gln Glu Ser Val Thr Val Gln Glu
1               5                   10                  15

Gly Leu Cys Val Leu Val Pro Cys Thr Phe Phe His Pro Ile Pro Tyr
                20                  25                  30

Tyr Asp Lys Asn Ser Pro Val His Gly Tyr Trp Phe Arg Glu Gly Ala
            35                  40                  45

Ile Ile Ser Arg Asp Ser Pro Val Ala Thr Asn Lys Leu Asp Gln Glu
        50                  55                  60

Val Gln Glu Glu Thr Gln Gly Arg Phe Arg Leu Leu Gly Asp Pro Ser
65                  70                  75                  80

Arg Asn Asn Cys Ser Leu Ser Ile Val Asp Ala Arg Arg Arg Asp Asn
                85                  90                  95

Gly Ser Tyr Phe Phe Arg Met Glu Arg Gly Ser Thr Lys Tyr Ser Tyr
                100                 105                 110

Lys Ser Pro Gln Leu Ser Val His Val Thr Asp Leu Thr His Arg Pro
            115                 120                 125

Lys Ile Leu Ile Pro Gly Thr Leu Glu Pro Gly His Ser Lys Asn Leu
        130                 135                 140

Thr Cys Ser Val Ser Trp Ala Cys Glu Gln Gly Thr Pro Pro Ile Phe
145                 150                 155                 160

Ser Trp Leu Ser Ala Ala Pro Thr Ser Leu Gly Pro Arg Thr Thr His
                165                 170                 175

Ser Ser Val Leu Ile Ile Thr Pro Arg Pro Gln Asp His Gly Thr Asn
                180                 185                 190

Leu Thr Cys Gln Val Lys Phe Ala Gly Ala Gly Val Thr Thr Glu Arg

```
                195                 200                 205
Thr Ile Gln Leu Asn Val Thr Tyr Val Pro Gln Asn Pro Thr Thr Gly
    210                 215                 220

Ile Phe Pro Gly Asp Gly Ser Gly Lys Gln Glu Thr Arg Ala Gly Val
225                 230                 235                 240

Val His

<210> SEQ ID NO 94
<211> LENGTH: 9
<212> TYPE: PRT
<213> ORGANISM: Homo sapiens

<400> SEQUENCE: 94

Asp Gln Glu Val Gln Glu Glu Thr Gln
1               5

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Gly Ser Gly Gly Ser
1               5

<210> SEQ ID NO 96
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Gly Ser Gly
1

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Ser Gly Gly
1               5

<210> SEQ ID NO 98
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30
```

Ser Asn Tyr Ala Asn Trp Val Gln Gln Lys Pro Gly Lys Ala Pro Lys
            35                  40                  45

Gly Leu Ile Gly Gly Thr Asn Lys Arg Ala Pro Gly Val Pro Ala Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
                100                 105                 110

Ser Gly Gly Ser Gln Val Gln Leu Val Gln Ser Gly Ala Glu Val Lys
            115                 120                 125

Lys Pro Gly Ala Ser Val Lys Val Ser Cys Lys Ala Ser Gly Tyr Thr
130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
                180                 185                 190

Ser Thr Val Tyr Met Glu Leu Ser Ser Leu Arg Ser Glu Asp Thr Ala
            195                 200                 205

Val Tyr Tyr Cys Ala Arg Asp Arg Ala Asn Thr Asp Phe Ser Tyr Gly
210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
                260                 265                 270

Ser Asn Thr Val Asn Trp Tyr Gln Gln Leu Pro Gly Thr Ala Pro Lys
            275                 280                 285

Leu Leu Ile Tyr Gly Asn Asn Gln Arg Pro Ser Gly Val Pro Asp Arg
            290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
                340                 345                 350

Gly Gly Ser Gly Gly Ser Glu Val Gln Leu Val Glu Ser Gly Gly Gly
            355                 360                 365

Leu Val Gln Pro Gly Gly Ser Leu Arg Leu Ser Cys Ala Ala Ser Gly
            370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
                420                 425                 430

Asp Asp Ser Lys Asn Ser Leu Tyr Leu Gln Met Asn Ser Leu Lys Thr
            435                 440                 445

```
Glu Asp Thr Ala Val Tyr Tyr Cys Ala Arg His Gly Asn Phe Gly Asn
            450                 455                 460

Ser Tyr Val Ser Trp Phe Ala Tyr Trp Gly Gln Gly Thr Leu Val Thr
465                 470                 475                 480

Val Ser Ser Ala Ala Ala Gly Ser His His His His His His
            485                 490

<210> SEQ ID NO 99
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
            35                  40                  45

Gly Leu Ile Gly Gly Thr Asn Lys Arg Ala Pro Gly Val Pro Ala Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
            115                 120                 125

Lys Pro Gly Ala Ser Val Lys Val Ser Cys Lys Ala Ser Gly Tyr Thr
    130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
            195                 200                 205

Val Tyr Tyr Cys Ala Arg Asp Arg Ala Val Thr Asp Tyr Tyr Tyr Gly
    210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
            260                 265                 270

Ser Asn Thr Val Asn Trp Tyr Gln Gln Leu Pro Gly Thr Ala Pro Lys
            275                 280                 285

Leu Leu Ile Tyr Gly Asn Asn Gln Arg Pro Ser Gly Val Pro Asp Arg
    290                 295                 300

Phe Ser Gly Ser Lys Ser Gly Thr Ser Ala Ser Leu Ala Ile Ser Gly
305                 310                 315                 320
```

```
Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
            340                 345                 350

Gly Gly Ser Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
    450                 455                 460

Ser Tyr Val Ser Trp Phe Ala Tyr Trp Gly Gln Gly Thr Leu Val Thr
465                 470                 475                 480

Val Ser Ser Ala Ala Ala Gly Ser His His His His His
                485                 490

<210> SEQ ID NO 100
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ala Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
    130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
```

```
                180             185                 190
Ser Thr Val Tyr Met Glu Leu Ser Ser Leu Arg Ser Glu Asp Thr Ala
            195                 200             205
Val Tyr Tyr Cys Ala Arg Asp Arg Ala Asn Thr Asp Tyr Ser Phe Gly
            210                 215             220
Met Asp Val Trp Gly Gln Gly Thr Leu Val Thr Val Ser Ser Gly Gly
225                 230                 235                 240
Ser Gly Gln Ser Val Leu Thr Gln Pro Pro Ser Ala Ser Gly Thr Pro
            245                 250             255
Gly Gln Arg Val Thr Ile Ser Cys Ser Gly Ser Arg Ser Asn Ile Gly
            260                 265             270
Ser Asn Thr Val Asn Trp Tyr Gln Gln Leu Pro Gly Thr Ala Pro Lys
            275                 280             285
Leu Leu Ile Tyr Gly Asn Asn Gln Arg Pro Ser Gly Val Pro Asp Arg
            290                 295             300
Phe Ser Gly Ser Lys Ser Gly Thr Ser Ala Ser Leu Ala Ile Ser Gly
305                 310                 315                 320
Leu Gln Ser Glu Asp Glu Ala Asp Tyr Tyr Cys Ala Thr Trp Asp Asp
            325                 330             335
Ser Leu Ile Gly Trp Val Phe Gly Gly Gly Thr Lys Leu Thr Val Leu
            340                 345             350
Gly Gly Ser Gly Gly Ser Glu Val Gln Leu Val Glu Ser Gly Gly Gly
            355                 360             365
Leu Val Gln Pro Gly Gly Ser Leu Arg Leu Ser Cys Ala Ala Ser Gly
            370                 375             380
Phe Thr Phe Ser Thr Tyr Ala Met Asn Trp Val Arg Gln Ala Pro Gly
385                 390                 395                 400
Lys Gly Leu Glu Trp Val Gly Arg Ile Arg Ser Lys Tyr Asn Asn Tyr
            405                 410             415
Ala Thr Tyr Tyr Ala Asp Ser Val Lys Asp Arg Phe Thr Ile Ser Arg
            420                 425             430
Asp Asp Ser Lys Asn Ser Leu Tyr Leu Gln Met Asn Ser Leu Lys Thr
            435                 440             445
Glu Asp Thr Ala Val Tyr Tyr Cys Ala Arg His Gly Asn Phe Gly Asn
            450                 455             460
Ser Tyr Val Ser Trp Phe Ala Tyr Trp Gly Gln Gly Thr Leu Val Thr
465                 470                 475                 480
Val Ser Ser Ala Ala Ala Gly Ser His His His His His
            485                 490

<210> SEQ ID NO 101
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Asp Ile Gln Met Thr Gln Ser Pro Ser Ser Leu Ser Ala Ser Val Gly
1               5                   10                  15
Asp Arg Val Thr Ile Thr Cys Arg Ser Ser Thr Gly Ala Val Thr Thr
            20                  25                  30
Ser Asn Tyr Ala Asn Trp Val Gln Gln Lys Pro Gly Lys Ala Pro Lys
            35                  40                  45
```

-continued

Gly Leu Ile Gly Gly Thr Asn Lys Arg Ala Pro Gly Val Pro Ala Arg
 50                  55                  60

Phe Ser Gly Ser Gly Ser Gly Thr Asp Phe Thr Leu Thr Ile Ser Ser
 65                  70                  75                  80

Leu Gln Pro Glu Asp Phe Ala Thr Tyr Tyr Cys Ala Leu Trp Tyr Ser
                 85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205

Val Tyr Tyr Cys Ala Arg Asp Arg Ala Asn Thr Asp Tyr Ser Leu Gly
210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
            260                 265                 270

Ser Asn Thr Val Asn Trp Tyr Gln Gln Leu Pro Gly Thr Ala Pro Lys
        275                 280                 285

Leu Leu Ile Tyr Gly Asn Asn Gln Arg Pro Ser Gly Val Pro Asp Arg
290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
            340                 345                 350

Gly Gly Ser Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
450                 455                 460

Ser Tyr Val Ser Trp Phe Ala Tyr Trp Gly Gln Gly Thr Leu Val Thr

```
                465                 470                 475                 480
Val Ser Ser Ala Ala Ala Gly Ser His His His His His
                        485                 490

<210> SEQ ID NO 102
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ala Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
    130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205

Val Tyr Tyr Cys Ala Arg Asp Arg Ala Asn Thr Asp Tyr Ser Phe Gly
    210                 215                 220

Met Asp Val Trp Gly Gln Gly Thr Leu Val Thr Val Ser Ser Gly Gly
225                 230                 235                 240

Ser Gly Gly Gln Ser Val Leu Thr Gln Pro Pro Ser Ala Ser Gly Thr
                245                 250                 255

Pro Gly Gln Arg Val Thr Ile Ser Cys Ser Gly Ser Arg Ser Asn Ile
            260                 265                 270

Gly Ser Asn Thr Val Asn Trp Tyr Gln Gln Leu Pro Gly Thr Ala Pro
        275                 280                 285

Lys Leu Leu Ile Tyr Gly Asn Asn Gln Arg Pro Ser Gly Val Pro Asp
    290                 295                 300

Arg Phe Ser Gly Ser Lys Ser Gly Thr Ser Ala Ser Leu Ala Ile Ser
305                 310                 315                 320

Gly Leu Gln Ser Glu Asp Glu Ala Asp Tyr Tyr Cys Ala Thr Trp Asp
                325                 330                 335
```

```
Asp Ser Leu Ile Gly Trp Val Phe Gly Gly Thr Lys Leu Thr Val
            340                 345                 350

Leu Gly Gly Ser Gly Ser Glu Val Gln Leu Val Glu Ser Gly Gly
        355                 360                 365

Gly Leu Val Gln Pro Gly Gly Ser Leu Arg Leu Ser Cys Ala Ala Ser
    370                 375                 380

Gly Phe Thr Phe Ser Thr Tyr Ala Met Asn Trp Val Arg Gln Ala Pro
385                 390                 395                 400

Gly Lys Gly Leu Glu Trp Val Gly Arg Ile Arg Ser Lys Tyr Asn Asn
                405                 410                 415

Tyr Ala Thr Tyr Tyr Ala Asp Ser Val Lys Asp Arg Phe Thr Ile Ser
            420                 425                 430

Arg Asp Asp Ser Lys Asn Ser Leu Tyr Leu Gln Met Asn Ser Leu Lys
        435                 440                 445

Thr Glu Asp Thr Ala Val Tyr Tyr Cys Ala Arg His Gly Asn Phe Gly
    450                 455                 460

Asn Ser Tyr Val Ser Trp Phe Ala Tyr Trp Gly Gln Gly Thr Leu Val
465                 470                 475                 480

Thr Val Ser Ser Ala Ala Ala Gly Ser His His His His His His
                485                 490                 495

<210> SEQ ID NO 103
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ala Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
    130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205
```

Val Tyr Tyr Cys Ala Arg Asp Arg Ala Asn Thr Asp Tyr Ser Leu Gly
    210                 215                 220

Met Asp Val Trp Gly Gln Gly Thr Leu Val Thr Val Ser Ser Gly Gly
225                 230                 235                 240

Ser Gly Gly Gln Ser Val Leu Thr Gln Pro Pro Ser Ala Ser Gly Thr
                245                 250                 255

Pro Gly Gln Arg Val Thr Ile Ser Cys Ser Gly Ser Arg Ser Asn Ile
            260                 265                 270

Gly Ser Asn Thr Val Asn Trp Tyr Gln Gln Leu Pro Gly Thr Ala Pro
        275                 280                 285

Lys Leu Leu Ile Tyr Gly Asn Asn Gln Arg Pro Ser Gly Val Pro Asp
    290                 295                 300

Arg Phe Ser Gly Ser Lys Ser Gly Thr Ser Ala Ser Leu Ala Ile Ser
305                 310                 315                 320

Gly Leu Gln Ser Glu Asp Glu Ala Asp Tyr Tyr Cys Ala Thr Trp Asp
                325                 330                 335

Asp Ser Leu Ile Gly Trp Val Phe Gly Gly Gly Thr Lys Leu Thr Val
            340                 345                 350

Leu Gly Gly Ser Gly Gly Ser Glu Val Gln Leu Val Glu Ser Gly Gly
        355                 360                 365

Gly Leu Val Gln Pro Gly Gly Ser Leu Arg Leu Ser Cys Ala Ala Ser
    370                 375                 380

Gly Phe Thr Phe Ser Thr Tyr Ala Met Asn Trp Val Arg Gln Ala Pro
385                 390                 395                 400

Gly Lys Gly Leu Glu Trp Val Gly Arg Ile Arg Ser Lys Tyr Asn Asn
                405                 410                 415

Tyr Ala Thr Tyr Tyr Ala Asp Ser Val Lys Asp Arg Phe Thr Ile Ser
            420                 425                 430

Arg Asp Asp Ser Lys Asn Ser Leu Tyr Leu Gln Met Asn Ser Leu Lys
        435                 440                 445

Thr Glu Asp Thr Ala Val Tyr Tyr Cys Ala Arg His Gly Asn Phe Gly
    450                 455                 460

Asn Ser Tyr Val Ser Trp Phe Ala Tyr Trp Gly Gln Gly Thr Leu Val
465                 470                 475                 480

Thr Val Ser Ser Ala Ala Ala Gly Ser His His His His His
                485                 490                 495

<210> SEQ ID NO 104
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
                20                  25                  30

Ser Asn Tyr Ala Asn Trp Val Gln Gln Lys Pro Gly Lys Ala Pro Lys
            35                  40                  45

Ala Leu Ile Gly Gly Thr Asn Lys Arg Ala Pro Gly Val Pro Ser Arg
        50                  55                  60

Phe Ser Gly Ser Leu Ile Gly Asp Lys Ala Thr Leu Thr Ile Ser Ser

```
                65                  70                  75                  80
Leu Gln Pro Glu Asp Phe Ala Thr Tyr Tyr Cys Ala Leu Trp Tyr Ser
                        85                  90                  95
Asn Leu Trp Val Phe Gly Gln Gly Thr Lys Val Glu Ile Lys Gly Gly
                    100                 105                 110
Ser Gly Gly Ser Gln Val Gln Leu Gln Glu Ser Gly Gly Gly Val Val
                115                 120                 125
Gln Pro Gly Arg Ser Leu Arg Leu Ser Cys Ala Ala Ser Gly Phe Ser
130                 135                 140
Phe Ser Asn Tyr Gly Ile His Trp Val Arg Gln Ala Pro Gly Lys Gly
145                 150                 155                 160
Leu Glu Trp Val Ala Leu Ile Ser Tyr Asp Gly Asn Lys Lys Phe Tyr
                    165                 170                 175
Ala Asp Ser Val Lys Gly Arg Phe Ala Ile Ser Arg Asp Thr Ser Lys
                180                 185                 190
Asn Thr Val Asp Leu Gln Met Thr Ser Leu Arg Pro Glu Asp Thr Ala
            195                 200                 205
Val Tyr Tyr Cys Ala Lys Asp Arg Leu Glu Ser Ala Ala Phe Asp Tyr
        210                 215                 220
Trp Gly Gln Gly Thr Leu Val Thr Val Ser Ser Gly Gly Ser Gly Gly
225                 230                 235                 240
Ser Ser Tyr Glu Leu Thr Gln Pro Pro Ser Val Ser Val Ala Pro Gly
                245                 250                 255
Gln Thr Ala Met Ile Thr Cys Gly Gly Asn Asn Ile Gly Ser Thr Thr
                260                 265                 270
Val His Trp Tyr Gln Gln Lys Pro Gly Gln Ala Pro Val Leu Val Val
            275                 280                 285
Tyr Asp Asp Asn Glu Arg Pro Ser Gly Ile Pro Glu Arg Phe Ser Gly
        290                 295                 300
Ser Asn Ser Gly Ser Thr Ala Thr Leu Thr Ile Asn Arg Val Glu Ala
305                 310                 315                 320
Gly Asp Glu Ala Asp Tyr Tyr Cys Gln Val Trp Asp Ser Gly Ser Asp
                325                 330                 335
His Val Val Phe Gly Gly Thr Lys Leu Thr Val Leu Gly Gly Ser
                340                 345                 350
Gly Gly Ser Glu Val Gln Leu Val Glu Ser Gly Gly Gly Leu Val Gln
            355                 360                 365
Pro Gly Gly Ser Leu Arg Leu Ser Cys Ala Ala Ser Gly Phe Thr Phe
        370                 375                 380
Ser Thr Tyr Ala Met Asn Trp Val Arg Gln Ala Pro Gly Lys Gly Leu
385                 390                 395                 400
Glu Trp Val Gly Arg Ile Arg Ser Lys Tyr Asn Asn Tyr Ala Thr Tyr
                405                 410                 415
Tyr Ala Asp Ser Val Lys Asp Arg Phe Thr Ile Ser Arg Asp Asp Ser
                420                 425                 430
Lys Asn Ser Leu Tyr Leu Gln Met Asn Ser Leu Lys Thr Glu Asp Thr
            435                 440                 445
Ala Val Tyr Tyr Cys Ala Arg His Gly Asn Phe Gly Asn Ser Tyr Val
        450                 455                 460
Ser Tyr Phe Ala Tyr Trp Gly Gln Gly Thr Leu Val Thr Val Ser Ser
465                 470                 475                 480
Ala Ala Ala Gly Ser His His His His His
                485                 490
```

<210> SEQ ID NO 105
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Ile Gly Trp Val Phe Gly Gly Gly Thr Lys Leu Thr Val Leu Gly Gly
            100                 105                 110

Ser Gly Gly Ser Glu Val Gln Leu Val Glu Ser Gly Gly Gly Leu Val
        115                 120                 125

Gln Pro Gly Gly Ser Leu Arg Leu Ser Cys Ala Ala Ser Gly Phe Thr
    130                 135                 140

Phe Ser Thr Tyr Ala Met Asn Trp Val Arg Gln Ala Pro Gly Lys Gly
145                 150                 155                 160

Leu Glu Trp Val Gly Arg Ile Arg Ser Lys Tyr Asn Asn Tyr Ala Thr
                165                 170                 175

Tyr Tyr Ala Asp Ser Val Lys Asp Arg Phe Thr Ile Ser Arg Asp Asp
            180                 185                 190

Ser Lys Asn Ser Leu Tyr Leu Gln Met Asn Ser Leu Lys Thr Glu Asp
        195                 200                 205

Thr Ala Val Tyr Tyr Cys Ala Arg His Gly Asn Phe Gly Asn Ser Tyr
    210                 215                 220

Val Ser Tyr Phe Ala Tyr Trp Gly Gln Gly Thr Leu Val Thr Val Ser
225                 230                 235                 240

Ser Gly Gly Ser Gly Gly Ser Asp Ile Gln Met Thr Gln Ser Pro Ser
                245                 250                 255

Ser Leu Ser Ala Ser Val Gly Asp Arg Val Thr Ile Thr Cys Arg Ser
            260                 265                 270

Ser Thr Gly Ala Val Thr Thr Ser Asn Tyr Ala Asn Trp Val Gln Gln
        275                 280                 285

Lys Pro Gly Lys Ala Pro Lys Ala Leu Ile Gly Gly Thr Asn Lys Arg
    290                 295                 300

Ala Pro Gly Val Pro Ser Arg Phe Ser Gly Ser Leu Ile Gly Asp Lys
305                 310                 315                 320

Ala Thr Leu Thr Ile Ser Ser Leu Gln Pro Glu Asp Phe Ala Thr Tyr
                325                 330                 335

Tyr Cys Ala Leu Trp Tyr Ser Asn Leu Trp Val Phe Gly Gln Gly Thr
            340                 345                 350

Lys Val Glu Ile Lys Gly Gly Ser Gly Gly Ser Gln Val Gln Leu Val
```

```
                    355                 360                 365
Gln Ser Gly Ala Glu Val Lys Lys Pro Gly Ala Ser Val Lys Val Ser
            370                 375                 380

Cys Lys Ala Ser Gly Tyr Thr Phe Thr Ser Tyr Asp Ile Asn Trp Val
385                 390                 395                 400

Arg Gln Ala Pro Gly Gln Gly Leu Glu Trp Met Gly Trp Met Asn Pro
                405                 410                 415

Asn Ser Gly Asn Thr Gly Phe Ala Gln Lys Phe Gln Gly Arg Val Thr
            420                 425                 430

Met Thr Arg Asp Thr Ser Thr Ser Thr Val Tyr Met Glu Leu Ser Ser
                435                 440                 445

Leu Arg Ser Glu Asp Thr Ala Val Tyr Tyr Cys Ala Arg Asp Arg Ala
            450                 455                 460

Asn Thr Asp Phe Ser Tyr Gly Met Asp Val Trp Gly Gln Gly Thr Leu
465                 470                 475                 480

Val Thr Val Ser Ser Ala Ala Ala Gly Ser His His His His His His
                485                 490                 495

<210> SEQ ID NO 106
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
    130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205

Val Tyr Tyr Cys Ala Arg Asp Arg Ala Asn Thr Asp Phe Ser Tyr Gly
    210                 215                 220
```

```
Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
            260                 265                 270

Ser Asn Thr Val Asn Trp Tyr Gln Gln Leu Pro Gly Thr Ala Pro Lys
        275                 280                 285

Leu Leu Ile Tyr Gly Asn Asn Gln Arg Pro Ser Gly Val Pro Asp Arg
    290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
            340                 345                 350

Gly Gly Ser Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
    450                 455                 460

Ser Tyr Val Ser Trp Phe Ala Tyr Trp Gly Gln Gly Thr Leu Val Thr
465                 470                 475                 480

Val Ser Ser Ala Ala Ala Gly Ser His His His His His His
                485                 490

<210> SEQ ID NO 107
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95
```

```
Asn Leu Trp Val Phe Gly Gln Gly Thr Lys Val Glu Ile Lys Gly Gly
                100                 105                 110

Ser Gly Gly Ser Gln Val Gln Leu Val Gln Ser Gly Ala Glu Val Lys
            115                 120                 125

Lys Pro Gly Ala Ser Val Lys Val Ser Cys Lys Ala Ser Gly Tyr Thr
        130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205

Val Tyr Tyr Cys Ala Arg Asp Arg Ala Asn Thr Asp Tyr Ser Phe Gly
210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
            245                 250                 255

Gly Gln Arg Val Thr Ile Ser Cys Ser Gly Ser Arg Ser Asn Ile Gly
        260                 265                 270

Ser Asn Thr Val Asn Trp Tyr Gln Gln Leu Pro Gly Thr Ala Pro Lys
    275                 280                 285

Leu Leu Ile Tyr Gly Asn Asn Gln Arg Pro Ser Gly Val Pro Asp Arg
290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
            325                 330                 335

Ser Leu Ile Gly Trp Val Phe Gly Gly Gly Thr Lys Leu Thr Val Leu
        340                 345                 350

Gly Gly Ser Gly Gly Ser Glu Val Gln Leu Val Glu Ser Gly Gly Gly
    355                 360                 365

Leu Val Gln Pro Gly Gly Ser Leu Arg Leu Ser Cys Ala Ala Ser Gly
370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
            405                 410                 415

Ala Thr Tyr Tyr Ala Asp Ser Val Lys Asp Arg Phe Thr Ile Ser Arg
        420                 425                 430

Asp Asp Ser Lys Asn Ser Leu Tyr Leu Gln Met Asn Ser Leu Lys Thr
    435                 440                 445

Glu Asp Thr Ala Val Tyr Tyr Cys Ala Arg His Gly Asn Phe Gly Asn
450                 455                 460

Ser Tyr Val Ser Trp Phe Ala Tyr Trp Gly Gln Gly Thr Leu Val Thr
465                 470                 475                 480

Val Ser Ser Ala Ala Ala Gly Ser His His His His His
            485                 490

<210> SEQ ID NO 108
<211> LENGTH: 494
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
    130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205

Val Tyr Tyr Cys Ala Arg Asp Arg Ala Asn Thr Asp Tyr Ser Leu Gly
    210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
            260                 265                 270

Ser Asn Thr Val Asn Trp Tyr Gln Gln Leu Pro Gly Thr Ala Pro Lys
        275                 280                 285

Leu Leu Ile Tyr Gly Asn Asn Gln Arg Pro Ser Gly Val Pro Asp Arg
    290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
            340                 345                 350

Gly Gly Ser Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380
```

```
Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
450                 455                 460

Ser Tyr Val Ser Trp Phe Ala Tyr Trp Gly Gln Gly Thr Leu Val Thr
465                 470                 475                 480

Val Ser Ser Ala Ala Ala Gly Ser His His His His His His
                485                 490

<210> SEQ ID NO 109
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Ala Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
    130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205

Val Tyr Tyr Cys Ala Arg Asp Arg Ala Val Thr Asp Tyr Tyr Tyr Gly
    210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
```

```
                    245                 250                 255
Gly Gln Arg Val Thr Ile Ser Cys Ser Gly Ser Arg Ser Asn Ile Gly
            260                 265                 270

Ser Asn Thr Val Asn Trp Tyr Gln Gln Leu Pro Gly Thr Ala Pro Lys
        275                 280                 285

Leu Leu Ile Tyr Gly Asn Asn Gln Arg Pro Ser Gly Val Pro Asp Arg
    290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
            340                 345                 350

Gly Gly Ser Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
    450                 455                 460

Ser Tyr Val Ser Tyr Phe Ala Tyr Trp Gly Gln Gly Thr Leu Val Thr
465                 470                 475                 480

Val Ser Ser Ala Ala Ala Gly Ser His His His His His His
                485                 490

<210> SEQ ID NO 110
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
                20                  25                  30

Ser Asn Tyr Ala Asn Trp Val Gln Gln Lys Pro Gly Lys Ala Pro Lys
            35                  40                  45

Gly Leu Ile Gly Gly Thr Asn Lys Arg Ala Pro Gly Val Pro Ser Arg
        50                  55                  60

Phe Ser Gly Ser Leu Ile Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110
```

-continued

Ser Gly Gly Ser Gln Val Gln Leu Val Gln Ser Gly Ala Glu Val Lys
            115                 120                 125

Lys Pro Gly Ala Ser Val Lys Val Ser Cys Lys Ala Ser Gly Tyr Thr
    130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205

Val Tyr Tyr Cys Ala Arg Asp Arg Ala Val Thr Asp Tyr Tyr Tyr Gly
    210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
            260                 265                 270

Ser Asn Thr Val Asn Trp Tyr Gln Gln Leu Pro Gly Thr Ala Pro Lys
        275                 280                 285

Leu Leu Ile Tyr Gly Asn Asn Gln Arg Pro Ser Gly Val Pro Asp Arg
    290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
            340                 345                 350

Gly Gly Ser Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
    450                 455                 460

Ser Tyr Val Ser Trp Phe Ala Tyr Trp Gly Gln Gly Thr Leu Val Thr
465                 470                 475                 480

Val Ser Ser Ala Ala Ala Gly Ser His His His His His His
                485                 490

<210> SEQ ID NO 111
<211> LENGTH: 494
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Ala Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205

Val Tyr Tyr Cys Ala Arg Asp Arg Ala Asn Thr Asp Phe Ser Tyr Gly
    210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
            260                 265                 270

Ser Asn Thr Val Asn Trp Tyr Gln Gln Leu Pro Gly Thr Ala Pro Lys
        275                 280                 285

Leu Leu Ile Tyr Gly Asn Asn Gln Arg Pro Ser Gly Val Pro Asp Arg
    290                 295                 300

Phe Ser Gly Ser Lys Ser Gly Ser Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
            340                 345                 350

Gly Gly Ser Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380

Phe Thr Phe Ser Thr Tyr Ala Met Asn Trp Val Arg Gln Ala Pro Gly
385                 390                 395                 400
```

-continued

```
Lys Gly Leu Glu Trp Val Gly Arg Ile Arg Ser Lys Tyr Asn Asn Tyr
                405                 410                 415
Ala Thr Tyr Tyr Ala Asp Ser Val Lys Asp Arg Phe Thr Ile Ser Arg
            420                 425                 430
Asp Asp Ser Lys Asn Ser Leu Tyr Leu Gln Met Asn Ser Leu Lys Thr
        435                 440                 445
Glu Asp Thr Ala Val Tyr Tyr Cys Ala Arg His Gly Asn Phe Gly Asn
    450                 455                 460
Ser Tyr Val Ser Tyr Phe Ala Tyr Trp Gly Gln Gly Thr Leu Val Thr
465                 470                 475                 480
Val Ser Ser Ala Ala Ala Gly Ser His His His His His His
            485                 490
```

<210> SEQ ID NO 112
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Asp Ile Gln Met Thr Gln Ser Pro Ser Ser Leu Ser Ala Ser Val Gly
1               5                   10                  15
Asp Arg Val Thr Ile Thr Cys Arg Ser Ser Thr Gly Ala Val Thr Thr
            20                  25                  30
Ser Asn Tyr Ala Asn Trp Val Gln Gln Lys Pro Gly Lys Ala Pro Lys
        35                  40                  45
Ala Leu Ile Gly Gly Thr Asn Lys Arg Ala Pro Gly Val Pro Ser Arg
    50                  55                  60
Phe Ser Gly Ser Leu Ile Gly Asp Lys Ala Thr Leu Thr Ile Ser Ser
65                  70                  75                  80
Leu Gln Pro Glu Asp Phe Ala Thr Tyr Tyr Cys Ala Leu Trp Tyr Ser
                85                  90                  95
Asn Leu Trp Val Phe Gly Gln Gly Thr Lys Val Glu Ile Lys Gly Gly
            100                 105                 110
Ser Gly Gly Ser Gln Val Gln Leu Val Gln Ser Gly Ala Glu Val Lys
        115                 120                 125
Lys Pro Gly Ala Ser Val Lys Val Ser Cys Lys Ala Ser Gly Tyr Thr
    130                 135                 140
Phe Thr Ser Tyr Asp Ile Asn Trp Val Arg Gln Ala Pro Gly Gln Gly
145                 150                 155                 160
Leu Glu Trp Met Gly Trp Met Asn Pro Asn Ser Gly Asn Thr Gly Phe
                165                 170                 175
Ala Gln Lys Phe Gln Gly Arg Val Thr Met Thr Arg Asp Thr Ser Thr
            180                 185                 190
Ser Thr Val Tyr Met Glu Leu Ser Ser Leu Arg Ser Glu Asp Thr Ala
        195                 200                 205
Val Tyr Tyr Cys Ala Arg Asp Arg Ala Asn Thr Asp Tyr Ser Phe Gly
    210                 215                 220
Met Asp Val Trp Gly Gln Gly Thr Leu Val Thr Val Ser Ser Gly Gly
225                 230                 235                 240
Ser Gly Gln Ser Val Leu Thr Gln Pro Pro Ser Ala Ser Gly Thr Pro
                245                 250                 255
Gly Gln Arg Val Thr Ile Ser Cys Ser Gly Ser Arg Ser Asn Ile Gly
            260                 265                 270
```

Ser Asn Thr Val Asn Trp Tyr Gln Gln Leu Pro Gly Thr Ala Pro Lys
            275                 280                 285

Leu Leu Ile Tyr Gly Asn Asn Gln Arg Pro Ser Gly Val Pro Asp Arg
        290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
            340                 345                 350

Gly Gly Ser Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
    450                 455                 460

Ser Tyr Val Ser Tyr Phe Ala Tyr Trp Gly Gln Gly Thr Leu Val Thr
465                 470                 475                 480

Val Ser Ser Ala Ala Ala Gly Ser His His His His His His
                485                 490

<210> SEQ ID NO 113
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Ala Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr

```
            130                 135                 140
Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205

Val Tyr Tyr Cys Ala Arg Asp Arg Ala Asn Thr Asp Tyr Ser Leu Gly
    210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
            260                 265                 270

Ser Asn Thr Val Asn Trp Tyr Gln Gln Leu Pro Gly Thr Ala Pro Lys
        275                 280                 285

Leu Leu Ile Tyr Gly Asn Asn Gln Arg Pro Ser Gly Val Pro Asp Arg
    290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
            340                 345                 350

Gly Gly Ser Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
    450                 455                 460

Ser Tyr Val Ser Tyr Phe Ala Tyr Trp Gly Gln Gly Thr Leu Val Thr
465                 470                 475                 480

Val Ser Ser Ala Ala Gly Ser His His His His His
                485                 490

<210> SEQ ID NO 114
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114
```

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Ala Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Glu Ser Leu Lys Ile Ser Cys Lys Gly Ser Gly Tyr Ser
    130                 135                 140

Phe Thr Ser Tyr Trp Ile Gly Trp Val Arg Gln Met Pro Gly Lys Gly
145                 150                 155                 160

Leu Glu Trp Met Gly Ile Ile Tyr Pro Gly Asp Ser Asp Thr Arg Tyr
                165                 170                 175

Ser Pro Ser Phe Gln Gly Gln Val Thr Ile Ser Ala Asp Lys Ser Ile
            180                 185                 190

Ser Thr Ala Tyr Leu Gln Trp Ser Ser Leu Lys Ala Ser Asp Thr Ala
        195                 200                 205

Met Tyr Tyr Cys Ala Arg His Lys Arg Gly Ser Asp Ala Phe Asp Ile
    210                 215                 220

Trp Gly Gln Gly Thr Thr Val Thr Val Ser Ser Gly Ser Gly Gly Gln
225                 230                 235                 240

Ser Val Leu Thr Gln Pro Pro Ser Val Ser Gly Ala Pro Gly Gln Arg
                245                 250                 255

Val Thr Ile Ser Cys Thr Gly Ser Ser Ser Asn Ile Gly Ala Gly Tyr
            260                 265                 270

Asp Val His Trp Tyr Gln Gln Leu Pro Gly Thr Ala Pro Lys Leu Leu
        275                 280                 285

Ile Tyr Gly Asn Ser Asn Arg Pro Ser Gly Val Pro Asp Arg Phe Ser
    290                 295                 300

Gly Ser Lys Ser Gly Thr Ser Ala Ser Leu Ala Ile Thr Gly Leu Gln
305                 310                 315                 320

Ala Glu Asp Glu Ala Asp Tyr Tyr Cys Gln Ser Tyr Asp Ser Ser Leu
                325                 330                 335

Ser Asp Val Val Phe Gly Gly Thr Lys Leu Thr Val Leu Gly Gly Gly
            340                 345                 350

Ser Gly Gly Ser Glu Val Gln Leu Val Glu Ser Gly Gly Gly Leu Val
        355                 360                 365

Gln Pro Gly Gly Ser Leu Arg Leu Ser Cys Ala Ala Ser Gly Phe Thr
    370                 375                 380

Phe Ser Thr Tyr Ala Met Asn Trp Val Arg Gln Ala Pro Gly Lys Gly
385                 390                 395                 400

Leu Glu Trp Val Gly Arg Ile Arg Ser Lys Tyr Asn Asn Tyr Ala Thr
                405                 410                 415

Tyr Tyr Ala Asp Ser Val Lys Asp Arg Phe Thr Ile Ser Arg Asp Asp
```

Ser Lys Asn Ser Leu Tyr Leu Gln Met Asn Ser Leu Lys Thr Glu Asp
            435                 440                 445

Thr Ala Val Tyr Tyr Cys Ala Arg His Gly Asn Phe Gly Asn Ser Tyr
    450                 455                 460

Val Ser Tyr Phe Ala Tyr Trp Gly Gln Gly Thr Leu Val Thr Val Ser
465                 470                 475                 480

Ser Ala Ala Gly Ser His His His His His
                485                 490

<210> SEQ ID NO 115
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Tyr Phe
            100                 105                 110

Ala Tyr Trp Gly Gln Gly Thr Leu Val Thr Val Ser Ser Gly Gly Ser
        115                 120                 125

Gly Gly Ser Gln Ser Val Leu Thr Gln Pro Ser Val Ser Gly Ala
    130                 135                 140

Pro Gly Gln Arg Val Thr Ile Ser Cys Thr Gly Ser Ser Ser Asn Ile
145                 150                 155                 160

Gly Ala Gly Tyr Asp Val His Trp Tyr Gln Gln Leu Pro Gly Thr Ala
                165                 170                 175

Pro Lys Leu Leu Ile Tyr Gly Asn Ser Asn Arg Pro Ser Gly Val Pro
            180                 185                 190

Asp Arg Phe Ser Gly Ser Lys Ser Gly Thr Ser Ala Ser Leu Ala Ile
        195                 200                 205

Thr Gly Leu Gln Ala Glu Asp Glu Ala Asp Tyr Tyr Cys Gln Ser Tyr
    210                 215                 220

Asp Ser Ser Leu Ser Asp Val Val Phe Gly Gly Thr Lys Leu Thr
225                 230                 235                 240

Val Leu Gly Gly Ser Gly Gln Val Gln Leu Val Gln Ser Gly Ala Glu
                245                 250                 255

Val Lys Lys Pro Gly Glu Ser Leu Lys Ile Ser Cys Lys Gly Ser Gly
            260                 265                 270

Tyr Ser Phe Thr Ser Tyr Trp Ile Gly Trp Val Arg Gln Met Pro Gly
        275                 280                 285

```
Lys Gly Leu Glu Trp Met Gly Ile Ile Tyr Pro Gly Asp Ser Asp Thr
    290                 295                 300

Arg Tyr Ser Pro Ser Phe Gln Gly Gln Val Thr Ile Ser Ala Asp Lys
305                 310                 315                 320

Ser Ile Ser Thr Ala Tyr Leu Gln Trp Ser Ser Leu Lys Ala Ser Asp
                325                 330                 335

Thr Ala Met Tyr Tyr Cys Ala Arg His Lys Arg Gly Ser Asp Ala Phe
                340                 345                 350

Asp Ile Trp Gly Gln Gly Thr Thr Val Thr Val Ser Ser Gly Gly Ser
            355                 360                 365

Gly Gly Ser Asp Ile Gln Met Thr Gln Ser Pro Ser Ser Leu Ser Ala
    370                 375                 380

Ser Val Gly Asp Arg Val Thr Ile Thr Cys Arg Ser Ser Thr Gly Ala
385                 390                 395                 400

Val Thr Thr Ser Asn Tyr Ala Asn Trp Val Gln Gln Lys Pro Gly Lys
                405                 410                 415

Ala Pro Lys Ala Leu Ile Gly Gly Thr Asn Lys Arg Ala Pro Gly Val
            420                 425                 430

Pro Ser Arg Phe Ser Gly Ser Leu Ile Gly Asp Lys Ala Thr Leu Thr
    435                 440                 445

Ile Ser Ser Leu Gln Pro Glu Asp Phe Ala Thr Tyr Tyr Cys Ala Leu
450                 455                 460

Trp Tyr Ser Asn Leu Trp Val Phe Gly Gln Gly Thr Lys Val Glu Ile
465                 470                 475                 480

Lys Ala Ala Ala Gly Ser His His His His His His
                485                 490

<210> SEQ ID NO 116
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Ala Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
    130                 135                 140

Phe Thr Ser Tyr Tyr Met His Trp Val Arg Gln Ala Pro Gly Gln Gly
145                 150                 155                 160
```

Leu Glu Trp Met Gly Ile Ile Asn Pro Ser Gly Ser Thr Ser Tyr
            165                 170                 175

Ala Gln Lys Phe Gln Gly Arg Val Thr Met Thr Arg Asp Thr Ser Thr
        180                 185                 190

Ser Thr Val Tyr Met Glu Leu Ser Ser Leu Arg Ser Glu Asp Thr Ala
    195                 200                 205

Val Tyr Tyr Cys Ala Arg Asp Val Pro Ala Ala Ile Asp Tyr Tyr
210                 215                 220

Gly Met Asp Val Trp Gly Gln Gly Thr Thr Val Thr Val Ser Ser Gly
225                 230                 235                 240

Gly Ser Gly Gln Ser Val Leu Thr Gln Pro Pro Ser Ala Ser Gly Thr
                245                 250                 255

Pro Gly Gln Arg Val Thr Ile Ser Cys Ser Gly Ser Ser Ser Asn Ile
            260                 265                 270

Gly Ser Asn Thr Val Asn Trp Tyr Gln Gln Leu Pro Gly Thr Ala Pro
        275                 280                 285

Lys Leu Leu Ile Tyr Ser Asp Asn Gln Arg Pro Ser Gly Val Pro Asp
    290                 295                 300

Arg Phe Ser Gly Ser Lys Ser Gly Ser Ser Ala Ser Leu Ala Ile Ser
305                 310                 315                 320

Gly Leu Gln Ser Asp Asp Glu Ala Asp Tyr Tyr Cys Ala Thr Trp Asp
                325                 330                 335

Asp Ser Leu Asn Gly Ala Val Phe Gly Gly Gly Thr Lys Leu Thr Val
            340                 345                 350

Leu Gly Gly Ser Gly Gly Ser Glu Val Gln Leu Val Glu Ser Gly Gly
        355                 360                 365

Gly Leu Val Gln Pro Gly Gly Ser Leu Arg Leu Ser Cys Ala Ala Ser
    370                 375                 380

Gly Phe Thr Phe Ser Thr Tyr Ala Met Asn Trp Val Arg Gln Ala Pro
385                 390                 395                 400

Gly Lys Gly Leu Glu Trp Val Gly Arg Ile Arg Ser Lys Tyr Asn Asn
                405                 410                 415

Tyr Ala Thr Tyr Tyr Ala Asp Ser Val Lys Asp Arg Phe Thr Ile Ser
            420                 425                 430

Arg Asp Asp Ser Lys Asn Ser Leu Tyr Leu Gln Met Asn Ser Leu Lys
        435                 440                 445

Thr Glu Asp Thr Ala Val Tyr Tyr Cys Ala Arg His Gly Asn Phe Gly
    450                 455                 460

Asn Ser Tyr Val Ser Tyr Phe Ala Tyr Trp Gly Gln Gly Thr Leu Val
465                 470                 475                 480

Thr Val Ser Ser Ala Ala Ala Gly Ser His His His His His
                485                 490                 495

<210> SEQ ID NO 117
<211> LENGTH: 495
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr

```
                20                  25                  30
Ser Asn Tyr Ala Asn Trp Val Gln Gln Lys Pro Gly Lys Ala Pro Lys
            35                  40                  45
Gly Leu Ile Gly Gly Thr Asn Lys Arg Ala Pro Gly Val Pro Ser Arg
50                  55                  60
Phe Ser Gly Ser Leu Ile Gly Thr Asp Phe Thr Leu Thr Ile Ser Ser
65                  70                  75                  80
Leu Gln Pro Glu Asp Phe Ala Thr Tyr Tyr Cys Ala Leu Trp Tyr Ser
                85                  90                  95
Asn Leu Trp Val Phe Gly Gln Gly Thr Lys Val Glu Ile Lys Gly Gly
            100                 105                 110
Ser Gly Gly Ser Gln Val Gln Leu Val Gln Ser Gly Ala Glu Val Lys
            115                 120                 125
Lys Pro Gly Ala Ser Val Lys Val Ser Cys Lys Ala Ser Gly Tyr Thr
            130                 135                 140
Phe Thr Ser Tyr Tyr Met His Trp Val Arg Gln Ala Pro Gly Gln Gly
145                 150                 155                 160
Leu Glu Trp Met Gly Ile Ile Asn Pro Ser Gly Gly Ser Thr Ser Tyr
                165                 170                 175
Ala Gln Lys Phe Gln Gly Arg Val Thr Met Thr Arg Asp Thr Ser Thr
            180                 185                 190
Ser Thr Val Tyr Met Glu Leu Ser Ser Leu Arg Ser Glu Asp Thr Ala
            195                 200                 205
Val Tyr Tyr Cys Ala Arg Asp Val Val Pro Ala Ala Ile Asp Tyr Tyr
            210                 215                 220
Gly Met Asp Val Trp Gly Gln Gly Thr Thr Val Thr Val Ser Ser Gly
225                 230                 235                 240
Gly Ser Gly Gln Ser Val Leu Thr Gln Pro Pro Ser Ala Ser Gly Thr
                245                 250                 255
Pro Gly Gln Arg Val Thr Ile Ser Cys Ser Gly Ser Ser Ser Asn Ile
            260                 265                 270
Gly Ser Asn Thr Val Asn Trp Tyr Gln Gln Leu Pro Gly Thr Ala Pro
            275                 280                 285
Lys Leu Leu Ile Tyr Ser Asp Asn Gln Arg Pro Ser Gly Val Pro Asp
            290                 295                 300
Arg Phe Ser Gly Ser Lys Ser Gly Ser Ser Ala Ser Leu Ala Ile Ser
305                 310                 315                 320
Gly Leu Gln Ser Asp Asp Glu Ala Asp Tyr Tyr Cys Ala Thr Trp Asp
                325                 330                 335
Asp Ser Leu Asn Gly Ala Val Phe Gly Gly Gly Thr Lys Leu Thr Val
            340                 345                 350
Leu Gly Gly Ser Gly Gly Ser Glu Val Gln Leu Val Glu Ser Gly Gly
            355                 360                 365
Gly Leu Val Gln Pro Gly Gly Ser Leu Arg Leu Ser Cys Ala Ala Ser
            370                 375                 380
Gly Phe Thr Phe Ser Thr Tyr Ala Met Asn Trp Val Arg Gln Ala Pro
385                 390                 395                 400
Gly Lys Gly Leu Glu Trp Val Gly Arg Ile Arg Ser Lys Tyr Asn Asn
                405                 410                 415
Tyr Ala Thr Tyr Tyr Ala Asp Ser Val Lys Asp Arg Phe Thr Ile Ser
            420                 425                 430
Arg Asp Asp Ser Lys Asn Ser Leu Tyr Leu Gln Met Asn Ser Leu Lys
            435                 440                 445
```

```
Thr Glu Asp Thr Ala Val Tyr Tyr Cys Ala Arg His Gly Asn Phe Gly
    450                 455                 460

Asn Ser Tyr Val Ser Trp Phe Ala Tyr Trp Gly Gln Gly Thr Leu Val
465                 470                 475                 480

Thr Val Ser Ser Ala Ala Ala Gly Ser His His His His His His
                485                 490                 495

<210> SEQ ID NO 118
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
                20                  25                  30

Ser Asn Tyr Ala Asn Trp Val Gln Gln Lys Pro Gly Lys Ala Pro Lys
            35                  40                  45

Ala Leu Ile Gly Gly Thr Asn Lys Arg Ala Pro Gly Val Pro Ser Arg
        50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ser Ser Val Lys Val Ser Cys Lys Ala Ser Gly Gly Thr
130                 135                 140

Phe Ser Ser Tyr Ala Ile Ser Trp Val Arg Gln Ala Pro Gly Gln Gly
145                 150                 155                 160

Leu Glu Trp Met Gly Gly Ile Tyr Pro Ile Phe Gly Ser Ala Asn Tyr
                165                 170                 175

Ala Gln Lys Phe Gln Gly Arg Val Thr Ile Thr Ala Asp Glu Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Arg Glu Tyr Tyr Asp Ser Ser Glu Trp Ala
210                 215                 220

Phe Asp Ile Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Ser Ser Asn Ile Gly
            260                 265                 270

Ser Asn Ile Val Asn Trp Tyr Gln Gln Leu Pro Gly Thr Ala Pro Lys
        275                 280                 285

Leu Leu Ile Tyr Ser Asn Asn Gln Arg Pro Ser Gly Val Pro Asp Arg
290                 295                 300

Phe Ser Gly Ser Lys Ser Gly Thr Ser Ala Ser Leu Ala Ile Ser Gly
```

```
305                 310                 315                 320
Leu Gln Ser Glu Asp Glu Ala Asp Tyr Tyr Cys Ala Ala Trp Asp Asp
                325                 330                 335

Ser Leu Lys Gly Tyr Val Phe Gly Gly Gly Thr Lys Leu Thr Val Leu
                340                 345                 350

Gly Gly Ser Gly Gly Ser Glu Val Gln Leu Val Glu Ser Gly Gly Gly
                355                 360                 365

Leu Val Gln Pro Gly Gly Ser Leu Arg Leu Ser Cys Ala Ala Ser Gly
370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
                420                 425                 430

Asp Asp Ser Lys Asn Ser Leu Tyr Leu Gln Met Asn Ser Leu Lys Thr
                435                 440                 445

Glu Asp Thr Ala Val Tyr Tyr Cys Ala Arg His Gly Asn Phe Gly Asn
                450                 455                 460

Ser Tyr Val Ser Tyr Phe Ala Tyr Trp Gly Gln Gly Thr Leu Val Thr
465                 470                 475                 480

Val Ser Ser Ala Ala Ala Gly Ser His His His His His His
                485                 490

<210> SEQ ID NO 119
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
                20                  25                  30

Ser Asn Tyr Ala Asn Trp Val Gln Gln Lys Pro Gly Lys Ala Pro Lys
                35                  40                  45

Ala Leu Ile Gly Gly Thr Asn Lys Arg Ala Pro Gly Val Pro Ser Arg
50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
                100                 105                 110

Ser Gly Gly Ser Gln Val Gln Leu Val Gln Ser Gly Ala Glu Val Lys
                115                 120                 125

Lys Pro Gly Ser Ser Val Lys Val Ser Cys Lys Ala Ser Gly Gly Thr
130                 135                 140

Phe Ser Ser Tyr Gly Ile Ser Trp Val Arg Gln Ala Pro Gly Gln Gly
145                 150                 155                 160

Leu Glu Trp Met Gly Gly Ile Ile Pro Ile Phe Gly Ser Ala His Tyr
                165                 170                 175
```

Ala Gln Lys Phe Gln Gly Arg Val Thr Ile Thr Ala Asp Glu Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Arg Glu Tyr Tyr Asp Ser Ser Glu Trp Ala
    210                 215                 220

Phe Asp Ile Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Ser Asn Ile Gly
        260                 265                 270

Ser Asn Thr Val Lys Trp Tyr Gln Gln Leu Pro Gly Thr Ala Pro Lys
    275                 280                 285

Leu Leu Ile Tyr Ser Asn Asn Gln Arg Ser Ser Gly Val Pro Asp Arg
290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Ala Trp Asp Asp
                325                 330                 335

Ser Leu Asn Gly Tyr Val Phe Gly Gly Gly Thr Lys Leu Thr Val Leu
            340                 345                 350

Gly Gly Ser Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
450                 455                 460

Ser Tyr Val Ser Tyr Phe Ala Tyr Trp Gly Gln Gly Thr Leu Val Thr
465                 470                 475                 480

Val Ser Ser Ala Ala Ala Gly Ser His His His His His His
                485                 490

<210> SEQ ID NO 120
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

```
Gly Leu Ile Gly Gly Thr Asn Lys Arg Ala Pro Val Pro Ser Arg
 50                  55                  60

Phe Ser Gly Ser Leu Ile Gly Thr Asp Phe Thr Leu Thr Ile Ser Ser
 65                  70                  75                  80

Leu Gln Pro Glu Asp Phe Ala Thr Tyr Tyr Cys Ala Leu Trp Tyr Ser
                 85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ser Ser Val Lys Val Ser Cys Lys Ala Ser Gly Gly Thr
    130                 135                 140

Phe Ser Ser Tyr Gly Ile Ser Trp Val Arg Gln Ala Pro Gly Gln Gly
145                 150                 155                 160

Leu Glu Trp Met Gly Gly Ile Ile Pro Ile Phe Gly Ser Ala His Tyr
                165                 170                 175

Ala Gln Lys Phe Gln Gly Arg Val Thr Ile Thr Ala Asp Glu Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Arg Glu Tyr Tyr Asp Ser Ser Glu Trp Ala
    210                 215                 220

Phe Asp Ile Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Ser Ser Asn Ile Gly
            260                 265                 270

Ser Asn Thr Val Lys Trp Tyr Gln Gln Leu Pro Gly Thr Ala Pro Lys
        275                 280                 285

Leu Leu Ile Tyr Ser Asn Asn Gln Arg Ser Ser Gly Val Pro Asp Arg
290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Ala Trp Asp Asp
                325                 330                 335

Ser Leu Asn Gly Tyr Val Phe Gly Gly Gly Thr Lys Leu Thr Val Leu
            340                 345                 350

Gly Gly Ser Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
    450                 455                 460
```

```
Ser Tyr Val Ser Trp Phe Ala Tyr Trp Gly Gln Gly Thr Leu Val Thr
465                 470                 475                 480

Val Ser Ser Ala Ala Ala Gly Ser His His His His His His
                485                 490
```

<210> SEQ ID NO 121
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Ala Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ser Ser Val Lys Val Ser Cys Lys Ala Ser Gly Gly Thr
    130                 135                 140

Phe Asp Ser Tyr Ala Ile Ser Trp Val Arg Gln Ala Pro Gly Gln Gly
145                 150                 155                 160

Leu Glu Trp Met Gly Gly Ile Ile Pro Ile Phe Gly Ser Ala His Tyr
                165                 170                 175

Ser Gln Lys Phe Gln Gly Arg Val Thr Ile Thr Ala Asp Glu Ser Thr
            180                 185                 190

Ser Thr Ala Tyr Met Glu Leu Ser Leu Arg Ser Glu Asp Thr Ala
        195                 200                 205

Val Tyr Tyr Cys Ala Arg Glu Tyr Tyr Asp Ser Ser Glu Trp Ala
    210                 215                 220

Phe Asp Ile Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Ser Asn Ile Gly
            260                 265                 270

Asp Asn Val Val Asn Trp Tyr Gln Gln Leu Pro Gly Thr Ala Pro Lys
        275                 280                 285

Leu Leu Ile Tyr Ser Thr Asn Lys Arg Pro Ser Gly Val Pro Asp Arg
    290                 295                 300

Phe Ser Gly Ser Lys Ser Gly Ser Ser Ala Ser Leu Ala Ile Ser Gly
305                 310                 315                 320

Leu Gln Ser Glu Asp Glu Ala Asp Tyr Tyr Cys Ala Ala Trp Asp Asp
                325                 330                 335
```

-continued

```
Ser Leu Ser Ala Tyr Val Phe Gly Gly Gly Thr Lys Leu Thr Val Leu
            340                 345                 350

Gly Gly Ser Gly Gly Ser Glu Val Gln Leu Val Glu Ser Gly Gly Gly
            355                 360                 365

Leu Val Gln Pro Gly Gly Ser Leu Arg Leu Ser Cys Ala Ala Ser Gly
370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
            405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
            435                 440                 445

Glu Asp Thr Ala Val Tyr Tyr Cys Ala Arg His Gly Asn Phe Gly Asn
450                 455                 460

Ser Tyr Val Ser Tyr Phe Ala Tyr Trp Gly Gln Gly Thr Leu Val Thr
465                 470                 475                 480

Val Ser Ser Ala Ala Ala Gly Ser His His His His His
            485                 490
```

<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 122

```
His His His His His His
1               5
```

<210> SEQ ID NO 123
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 123

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ala Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125
```

```
Lys Pro Gly Ala Ser Val Lys Val Ser Cys Lys Ala Ser Gly Tyr Thr
            130                 135                 140
Phe Thr Ser Tyr Asp Ile Asn Trp Val Arg Gln Ala Pro Gly Gln Gly
145                 150                 155                 160
Leu Glu Trp Met Gly Trp Met Asn Pro Asn Ser Gly Asn Thr Gly Phe
                165                 170                 175
Ala Gln Lys Phe Gln Gly Arg Val Thr Met Thr Arg Asp Thr Ser Thr
            180                 185                 190
Ser Thr Val Tyr Met Glu Leu Ser Ser Leu Arg Ser Glu Asp Thr Ala
                195                 200                 205
Val Tyr Tyr Cys Ala Arg Asp Arg Ala Asn Thr Asp Phe Ser Tyr Gly
            210                 215                 220
Met Asp Val Trp Gly Gln Gly Thr Leu Val Thr Val Ser Ser Gly Gly
225                 230                 235                 240
Ser Gly Gln Ser Val Leu Thr Gln Pro Pro Ser Ala Ser Gly Thr Pro
                245                 250                 255
Gly Gln Arg Val Thr Ile Ser Cys Ser Gly Ser Arg Ser Asn Ile Gly
            260                 265                 270
Ser Asn Thr Val Asn Trp Tyr Gln Gln Leu Pro Gly Thr Ala Pro Lys
            275                 280                 285
Leu Leu Ile Tyr Gly Asn Asn Gln Arg Pro Ser Gly Val Pro Asp Arg
290                 295                 300
Phe Ser Gly Ser Lys Ser Gly Thr Ser Ala Ser Leu Ala Ile Ser Gly
305                 310                 315                 320
Leu Gln Ser Glu Asp Glu Ala Asp Tyr Tyr Cys Ala Thr Trp Asp Asp
                325                 330                 335
Ser Leu Ile Gly Trp Val Phe Gly Gly Gly Thr Lys Leu Thr Val Leu
                340                 345                 350
Gly Gly Ser Gly Gly Ser Glu Val Gln Leu Val Glu Ser Gly Gly Gly
            355                 360                 365
Leu Val Gln Pro Gly Gly Ser Leu Arg Leu Ser Cys Ala Ala Ser Gly
            370                 375                 380
Phe Thr Phe Ser Thr Tyr Ala Met Asn Trp Val Arg Gln Ala Pro Gly
385                 390                 395                 400
Lys Gly Leu Glu Trp Val Gly Arg Ile Arg Ser Lys Tyr Asn Asn Tyr
                405                 410                 415
Ala Thr Tyr Tyr Ala Asp Ser Val Lys Asp Arg Phe Thr Ile Ser Arg
            420                 425                 430
Asp Asp Ser Lys Asn Ser Leu Tyr Leu Gln Met Asn Ser Leu Lys Thr
            435                 440                 445
Glu Asp Thr Ala Val Tyr Tyr Cys Ala Arg His Gly Asn Phe Gly Asn
450                 455                 460
Ser Tyr Val Ser Trp Phe Ala Tyr Trp Gly Gln Gly Thr Leu Val Thr
465                 470                 475                 480
Val Ser Ser

<210> SEQ ID NO 124
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 124

Asp Ile Gln Met Thr Gln Ser Pro Ser Ser Leu Ser Ala Ser Val Gly
```

-continued

```
  1               5                   10                  15
Asp Arg Val Thr Ile Thr Cys Arg Ser Ser Thr Gly Ala Val Thr Thr
                 20                  25                  30

Ser Asn Tyr Ala Asn Trp Val Gln Gln Lys Pro Gly Lys Ala Pro Lys
             35                  40                  45

Gly Leu Ile Gly Gly Thr Asn Lys Arg Ala Pro Gly Val Pro Ala Arg
         50                  55                  60

Phe Ser Gly Ser Gly Ser Gly Thr Asp Phe Thr Leu Thr Ile Ser Ser
 65                  70                  75                  80

Leu Gln Pro Glu Asp Phe Ala Thr Tyr Tyr Cys Ala Leu Trp Tyr Ser
                 85                  90                  95

Asn Leu Trp Val Phe Gly Gln Gly Thr Lys Val Glu Ile Lys Gly Gly
             100                 105                 110

Ser Gly Gly Ser Gln Val Gln Leu Val Gln Ser Gly Ala Glu Val Lys
         115                 120                 125

Lys Pro Gly Ala Ser Val Lys Val Ser Cys Lys Ala Ser Gly Tyr Thr
130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                 165                 170                 175

Ala Gln Lys Phe Gln Gly Arg Val Thr Met Thr Arg Asp Thr Ser Thr
             180                 185                 190

Ser Thr Val Tyr Met Glu Leu Ser Ser Leu Arg Ser Glu Asp Thr Ala
         195                 200                 205

Val Tyr Tyr Cys Ala Arg Asp Arg Ala Val Thr Asp Tyr Tyr Tyr Gly
210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                 245                 250                 255

Gly Gln Arg Val Thr Ile Ser Cys Ser Gly Ser Arg Ser Asn Ile Gly
             260                 265                 270

Ser Asn Thr Val Asn Trp Tyr Gln Gln Leu Pro Gly Thr Ala Pro Lys
         275                 280                 285

Leu Leu Ile Tyr Gly Asn Asn Gln Arg Pro Ser Gly Val Pro Asp Arg
290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                 325                 330                 335

Ser Leu Ile Gly Trp Val Phe Gly Gly Gly Thr Lys Leu Thr Val Leu
             340                 345                 350

Gly Gly Ser Gly Gly Ser Glu Val Gln Leu Val Glu Ser Gly Gly Gly
         355                 360                 365

Leu Val Gln Pro Gly Gly Ser Leu Arg Leu Ser Cys Ala Ala Ser Gly
370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                 405                 410                 415

Ala Thr Tyr Tyr Ala Asp Ser Val Lys Asp Arg Phe Thr Ile Ser Arg
             420                 425                 430
```

```
Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
    450                 455                 460

Ser Tyr Val Ser Trp Phe Ala Tyr Trp Gly Gln Gly Thr Leu Val Thr
465                 470                 475                 480

Val Ser Ser

<210> SEQ ID NO 125
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ala Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
    130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205

Val Tyr Tyr Cys Ala Arg Asp Arg Ala Asn Thr Asp Tyr Ser Phe Gly
    210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
            260                 265                 270

Ser Asn Thr Val Asn Trp Tyr Gln Gln Leu Pro Gly Thr Ala Pro Lys
        275                 280                 285

Leu Leu Ile Tyr Gly Asn Asn Gln Arg Pro Ser Gly Val Pro Asp Arg
    290                 295                 300
```

```
Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
            325                 330                 335

Ser Leu Ile Gly Trp Val Phe Gly Gly Gly Thr Lys Leu Thr Val Leu
            340                 345                 350

Gly Gly Ser Gly Gly Ser Glu Val Gln Leu Val Glu Ser Gly Gly Gly
            355                 360                 365

Leu Val Gln Pro Gly Gly Ser Leu Arg Leu Ser Cys Ala Ala Ser Gly
            370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
            405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
            435                 440                 445

Glu Asp Thr Ala Val Tyr Tyr Cys Ala Arg His Gly Asn Phe Gly Asn
450                 455                 460

Ser Tyr Val Ser Trp Phe Ala Tyr Trp Gly Gln Gly Thr Leu Val Thr
465                 470                 475                 480

Val Ser Ser

<210> SEQ ID NO 126
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ala Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
            85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
    130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
            165                 170                 175

Ala Gln Lys Phe Gln Gly Arg Val Thr Met Thr Arg Asp Thr Ser Thr
```

```
                180             185              190
Ser Thr Val Tyr Met Glu Leu Ser Ser Leu Arg Ser Glu Asp Thr Ala
            195                 200             205

Val Tyr Tyr Cys Ala Arg Asp Arg Ala Asn Thr Asp Tyr Ser Leu Gly
    210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
                260                 265                 270

Ser Asn Thr Val Asn Trp Tyr Gln Gln Leu Pro Gly Thr Ala Pro Lys
            275                 280                 285

Leu Leu Ile Tyr Gly Asn Asn Gln Arg Pro Ser Gly Val Pro Asp Arg
290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Thr Lys Leu Thr Val Leu
            340                 345                 350

Gly Gly Ser Gly Gly Ser Glu Val Gln Leu Val Glu Ser Gly Gly Gly
            355                 360                 365

Leu Val Gln Pro Gly Gly Ser Leu Arg Leu Ser Cys Ala Ala Ser Gly
            370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
                435                 440                 445

Glu Asp Thr Ala Val Tyr Tyr Cys Ala Arg His Gly Asn Phe Gly Asn
            450                 455                 460

Ser Tyr Val Ser Trp Phe Ala Tyr Trp Gly Gln Gly Thr Leu Val Thr
465                 470                 475                 480

Val Ser Ser

<210> SEQ ID NO 127
<211> LENGTH: 484
<212> TYPE: PRT
<213> ORGANISM: Artificial Sequence
<220> FEATURE:
<223> OTHER INFORMATION: Synthetic polypeptide

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ala Arg
    50                  55                  60
```

```
Phe Ser Gly Ser Gly Ser Gly Thr Asp Phe Thr Leu Thr Ile Ser Ser
 65                  70                  75                  80

Leu Gln Pro Glu Asp Phe Ala Thr Tyr Tyr Cys Ala Leu Trp Tyr Ser
             85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205

Val Tyr Tyr Cys Ala Arg Asp Arg Ala Asn Thr Asp Tyr Ser Phe Gly
210                 215                 220

Met Asp Val Trp Gly Gln Gly Thr Leu Val Thr Val Ser Ser Gly Gly
225                 230                 235                 240

Ser Gly Gly Gln Ser Val Leu Thr Gln Pro Pro Ser Ala Ser Gly Thr
            245                 250                 255

Pro Gly Gln Arg Val Thr Ile Ser Cys Ser Gly Ser Arg Ser Asn Ile
            260                 265                 270

Gly Ser Asn Thr Val Asn Trp Tyr Gln Gln Leu Pro Gly Thr Ala Pro
            275                 280                 285

Lys Leu Leu Ile Tyr Gly Asn Asn Gln Arg Pro Ser Gly Val Pro Asp
290                 295                 300

Arg Phe Ser Gly Ser Lys Ser Gly Thr Ser Ala Ser Leu Ala Ile Ser
305                 310                 315                 320

Gly Leu Gln Ser Glu Asp Glu Ala Asp Tyr Tyr Cys Ala Thr Trp Asp
            325                 330                 335

Asp Ser Leu Ile Gly Trp Val Phe Gly Gly Gly Thr Lys Leu Thr Val
            340                 345                 350

Leu Gly Gly Ser Gly Gly Ser Glu Val Gln Leu Val Glu Ser Gly Gly
            355                 360                 365

Gly Leu Val Gln Pro Gly Gly Ser Leu Arg Leu Ser Cys Ala Ala Ser
            370                 375                 380

Gly Phe Thr Phe Ser Thr Tyr Ala Met Asn Trp Val Arg Gln Ala Pro
385                 390                 395                 400

Gly Lys Gly Leu Glu Trp Val Gly Arg Ile Arg Ser Lys Tyr Asn Asn
            405                 410                 415

Tyr Ala Thr Tyr Tyr Ala Asp Ser Val Lys Asp Arg Phe Thr Ile Ser
            420                 425                 430

Arg Asp Asp Ser Lys Asn Ser Leu Tyr Leu Gln Met Asn Ser Leu Lys
            435                 440                 445

Thr Glu Asp Thr Ala Val Tyr Tyr Cys Ala Arg His Gly Asn Phe Gly
            450                 455                 460

Asn Ser Tyr Val Ser Trp Phe Ala Tyr Trp Gly Gln Gly Thr Leu Val
465                 470                 475                 480
```

Thr Val Ser Ser

<210> SEQ ID NO 128
<211> LENGTH: 484
<212> TYPE: PRT
<213> ORGANISM: Artificial Sequence
<220> FEATURE:
<223> OTHER INFORMATION: Synthetic polypeptide

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ala Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205

Val Tyr Tyr Cys Ala Arg Asp Arg Ala Asn Thr Asp Tyr Ser Leu Gly
    210                 215                 220

Met Asp Val Trp Gly Gln Gly Thr Leu Val Thr Val Ser Ser Gly Gly
225                 230                 235                 240

Ser Gly Gly Gln Ser Val Leu Thr Gln Pro Pro Ser Ala Ser Gly Thr
                245                 250                 255

Pro Gly Gln Arg Val Thr Ile Ser Cys Ser Gly Ser Arg Ser Asn Ile
            260                 265                 270

Gly Ser Asn Thr Val Asn Trp Tyr Gln Gln Leu Pro Gly Thr Ala Pro
        275                 280                 285

Lys Leu Leu Ile Tyr Gly Asn Asn Gln Arg Pro Ser Gly Val Pro Asp
    290                 295                 300

Arg Phe Ser Gly Ser Lys Ser Gly Thr Ser Ala Ser Leu Ala Ile Ser
305                 310                 315                 320

Gly Leu Gln Ser Glu Asp Glu Ala Asp Tyr Tyr Cys Ala Thr Trp Asp
                325                 330                 335

Asp Ser Leu Ile Gly Trp Val Phe Gly Gly Gly Thr Lys Leu Thr Val
            340                 345                 350

Leu Gly Gly Ser Gly Gly Ser Glu Val Gln Leu Val Glu Ser Gly Gly

```
                    355                 360                 365

Gly Leu Val Gln Pro Gly Ser Leu Arg Leu Ser Cys Ala Ala Ser
        370                 375                 380

Gly Phe Thr Phe Ser Thr Tyr Ala Met Asn Trp Val Arg Gln Ala Pro
385                 390                 395                 400

Gly Lys Gly Leu Glu Trp Val Gly Arg Ile Arg Ser Lys Tyr Asn Asn
                405                 410                 415

Tyr Ala Thr Tyr Tyr Ala Asp Ser Val Lys Asp Arg Phe Thr Ile Ser
            420                 425                 430

Arg Asp Asp Ser Lys Asn Ser Leu Tyr Leu Gln Met Asn Ser Leu Lys
        435                 440                 445

Thr Glu Asp Thr Ala Val Tyr Tyr Cys Ala Arg His Gly Asn Phe Gly
    450                 455                 460

Asn Ser Tyr Val Ser Trp Phe Ala Tyr Trp Gly Gln Gly Thr Leu Val
465                 470                 475                 480

Thr Val Ser Ser

<210> SEQ ID NO 129
<211> LENGTH: 480
<212> TYPE: PRT
<213> ORGANISM: Artificial Sequence
<220> FEATURE:
<223> OTHER INFORMATION: Synthetic polypeptide

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Ala Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Gln Glu Ser Gly Gly Gly Val Val
        115                 120                 125

Gln Pro Gly Arg Ser Leu Arg Leu Ser Cys Ala Ala Ser Gly Phe Ser
    130                 135                 140

Phe Ser Asn Tyr Gly Ile His Trp Val Arg Gln Ala Pro Gly Lys Gly
145                 150                 155                 160

Leu Glu Trp Val Ala Leu Ile Ser Tyr Asp Gly Asn Lys Lys Phe Tyr
                165                 170                 175

Ala Asp Ser Val Lys Gly Arg Phe Ala Ile Ser Arg Asp Thr Ser Lys
            180                 185                 190

Asn Thr Val Asp Leu Gln Met Thr Ser Leu Arg Pro Glu Asp Thr Ala
        195                 200                 205

Val Tyr Tyr Cys Ala Lys Asp Arg Leu Glu Ser Ala Ala Phe Asp Tyr
    210                 215                 220

Trp Gly Gln Gly Thr Leu Val Thr Val Ser Ser Gly Gly Ser Gly Gly
225                 230                 235                 240
```

```
Ser Ser Tyr Glu Leu Thr Gln Pro Pro Ser Val Ser Val Ala Pro Gly
            245                 250                 255

Gln Thr Ala Met Ile Thr Cys Gly Gly Asn Asn Ile Gly Ser Thr Thr
            260                 265                 270

Val His Trp Tyr Gln Gln Lys Pro Gly Gln Ala Pro Val Leu Val Val
            275                 280                 285

Tyr Asp Asp Asn Glu Arg Pro Ser Gly Ile Pro Glu Arg Phe Ser Gly
            290                 295                 300

Ser Asn Ser Gly Ser Thr Ala Thr Leu Thr Ile Asn Arg Val Glu Ala
305                 310                 315                 320

Gly Asp Glu Ala Asp Tyr Tyr Cys Gln Val Trp Asp Ser Gly Ser Asp
                325                 330                 335

His Val Val Phe Gly Gly Gly Thr Lys Leu Thr Val Leu Gly Gly Ser
                340                 345                 350

Gly Gly Ser Glu Val Gln Leu Val Glu Ser Gly Gly Gly Leu Val Gln
                355                 360                 365

Pro Gly Gly Ser Leu Arg Leu Ser Cys Ala Ala Ser Gly Phe Thr Phe
            370                 375                 380

Ser Thr Tyr Ala Met Asn Trp Val Arg Gln Ala Pro Gly Lys Gly Leu
385                 390                 395                 400

Glu Trp Val Gly Arg Ile Arg Ser Lys Tyr Asn Asn Tyr Ala Thr Tyr
                405                 410                 415

Tyr Ala Asp Ser Val Lys Asp Arg Phe Thr Ile Ser Arg Asp Asp Ser
                420                 425                 430

Lys Asn Ser Leu Tyr Leu Gln Met Asn Ser Leu Lys Thr Glu Asp Thr
            435                 440                 445

Ala Val Tyr Tyr Cys Ala Arg His Gly Asn Phe Gly Asn Ser Tyr Val
450                 455                 460

Ser Tyr Phe Ala Tyr Trp Gly Gln Gly Thr Leu Val Thr Val Ser Ser
465                 470                 475                 480

<210> SEQ ID NO 130
<211> LENGTH: 485
<212> TYPE: PRT
<213> ORGANISM: Artificial Sequence
<220> FEATURE:
<223> OTHER INFORMATION: Synthetic polypeptide

<400> SEQUENCE: 130

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Gly Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Ile Gly Trp Val Phe Gly Gly Gly Thr Lys Leu Thr Val Leu Gly Gly
            100                 105                 110

Ser Gly Gly Ser Glu Val Gln Leu Val Glu Ser Gly Gly Gly Leu Val
        115                 120                 125
```

Gln Pro Gly Gly Ser Leu Arg Leu Ser Cys Ala Ala Ser Gly Phe Thr
            130                 135                 140

Phe Ser Thr Tyr Ala Met Asn Trp Val Arg Gln Ala Pro Gly Lys Gly
145                 150                 155                 160

Leu Glu Trp Val Gly Arg Ile Arg Ser Lys Tyr Asn Asn Tyr Ala Thr
                165                 170                 175

Tyr Tyr Ala Asp Ser Val Lys Asp Arg Phe Thr Ile Ser Arg Asp Asp
            180                 185                 190

Ser Lys Asn Ser Leu Tyr Leu Gln Met Asn Ser Leu Lys Thr Glu Asp
        195                 200                 205

Thr Ala Val Tyr Tyr Cys Ala Arg His Gly Asn Phe Gly Asn Ser Tyr
210                 215                 220

Val Ser Tyr Phe Ala Tyr Trp Gly Gln Gly Thr Leu Val Thr Val Ser
225                 230                 235                 240

Ser Gly Gly Ser Gly Gly Ser Asp Ile Gln Met Thr Gln Ser Pro Ser
                245                 250                 255

Ser Leu Ser Ala Ser Val Gly Asp Arg Val Thr Ile Thr Cys Arg Ser
            260                 265                 270

Ser Thr Gly Ala Val Thr Thr Ser Asn Tyr Ala Asn Trp Val Gln Gln
        275                 280                 285

Lys Pro Gly Lys Ala Pro Lys Ala Leu Ile Gly Gly Thr Asn Lys Arg
290                 295                 300

Ala Pro Gly Val Pro Ser Arg Phe Ser Gly Ser Leu Ile Gly Asp Lys
305                 310                 315                 320

Ala Thr Leu Thr Ile Ser Ser Leu Gln Pro Glu Asp Phe Ala Thr Tyr
                325                 330                 335

Tyr Cys Ala Leu Trp Tyr Ser Asn Leu Trp Val Phe Gly Gln Gly Thr
            340                 345                 350

Lys Val Glu Ile Lys Gly Gly Ser Gly Gly Ser Gln Val Gln Leu Val
        355                 360                 365

Gln Ser Gly Ala Glu Val Lys Lys Pro Gly Ala Ser Val Lys Val Ser
370                 375                 380

Cys Lys Ala Ser Gly Tyr Thr Phe Thr Ser Tyr Asp Ile Asn Trp Val
385                 390                 395                 400

Arg Gln Ala Pro Gly Gln Gly Leu Glu Trp Met Gly Trp Met Asn Pro
                405                 410                 415

Asn Ser Gly Asn Thr Gly Phe Ala Gln Lys Phe Gln Gly Arg Val Thr
            420                 425                 430

Met Thr Arg Asp Thr Ser Thr Ser Thr Val Tyr Met Glu Leu Ser Ser
        435                 440                 445

Leu Arg Ser Glu Asp Thr Ala Val Tyr Tyr Cys Ala Arg Asp Arg Ala
450                 455                 460

Asn Thr Asp Phe Ser Tyr Gly Met Asp Val Trp Gly Gln Gly Thr Leu
465                 470                 475                 480

Val Thr Val Ser Ser
                485

<210> SEQ ID NO 131
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 131

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
            115                 120                 125

Lys Pro Gly Ala Ser Val Lys Val Ser Cys Lys Ala Ser Gly Tyr Thr
    130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
            195                 200                 205

Val Tyr Tyr Cys Ala Arg Asp Arg Ala Asn Thr Asp Phe Ser Tyr Gly
    210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
            260                 265                 270

Ser Asn Thr Val Asn Trp Tyr Gln Gln Leu Pro Gly Thr Ala Pro Lys
            275                 280                 285

Leu Leu Ile Tyr Gly Asn Asn Gln Arg Pro Ser Gly Val Pro Asp Arg
    290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
            340                 345                 350

Gly Gly Ser Gly Gly Ser Glu Val Gln Leu Val Glu Ser Gly Gly Gly
            355                 360                 365

Leu Val Gln Pro Gly Gly Ser Leu Arg Leu Ser Cys Ala Ala Ser Gly
    370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415
```

```
Ala Thr Tyr Tyr Ala Asp Ser Val Lys Asp Arg Phe Thr Ile Ser Arg
                420                 425                 430

Asp Asp Ser Lys Asn Ser Leu Tyr Leu Gln Met Asn Ser Leu Lys Thr
            435                 440                 445

Glu Asp Thr Ala Val Tyr Tyr Cys Ala Arg His Gly Asn Phe Gly Asn
        450                 455                 460

Ser Tyr Val Ser Trp Phe Ala Tyr Trp Gly Gln Gly Thr Leu Val Thr
465                 470                 475                 480

Val Ser Ser

<210> SEQ ID NO 132
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
    130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205

Val Tyr Tyr Cys Ala Arg Asp Arg Ala Asn Thr Asp Tyr Ser Phe Gly
    210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
            260                 265                 270

Ser Asn Thr Val Asn Trp Tyr Gln Gln Leu Pro Gly Thr Ala Pro Lys
        275                 280                 285

Leu Leu Ile Tyr Gly Asn Asn Gln Arg Pro Ser Gly Val Pro Asp Arg
```

```
                290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
                340                 345                 350

Gly Gly Ser Gly Ser Glu Val Gln Leu Val Glu Ser Gly Gly Gly
            355                 360                 365

Leu Val Gln Pro Gly Gly Ser Leu Arg Leu Ser Cys Ala Ala Ser Gly
            370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
                420                 425                 430

Asp Asp Ser Lys Asn Ser Leu Tyr Leu Gln Met Asn Ser Leu Lys Thr
                435                 440                 445

Glu Asp Thr Ala Val Tyr Tyr Cys Ala Arg His Gly Asn Phe Gly Asn
                450                 455                 460

Ser Tyr Val Ser Trp Phe Ala Tyr Trp Gly Gln Gly Thr Leu Val Thr
465                 470                 475                 480

Val Ser Ser

<210> SEQ ID NO 133
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
                20                  25                  30

Ser Asn Tyr Ala Asn Trp Val Gln Gln Lys Pro Gly Lys Ala Pro Lys
                35                  40                  45

Gly Leu Ile Gly Gly Thr Asn Lys Arg Ala Pro Gly Val Pro Ser Arg
            50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
                100                 105                 110

Ser Gly Gly Ser Gln Val Gln Leu Val Gln Ser Gly Ala Glu Val Lys
            115                 120                 125

Lys Pro Gly Ala Ser Val Lys Val Ser Cys Lys Ala Ser Gly Tyr Thr
            130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175
```

```
Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205

Val Tyr Tyr Cys Ala Arg Asp Arg Ala Asn Thr Asp Tyr Ser Leu Gly
    210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
            260                 265                 270

Ser Asn Thr Val Asn Trp Tyr Gln Gln Leu Pro Gly Thr Ala Pro Lys
        275                 280                 285

Leu Leu Ile Tyr Gly Asn Asn Gln Arg Pro Ser Gly Val Pro Asp Arg
    290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
            340                 345                 350

Gly Gly Ser Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
    450                 455                 460

Ser Tyr Val Ser Trp Phe Ala Tyr Trp Gly Gln Gly Thr Leu Val Thr
465                 470                 475                 480

Val Ser Ser

<210> SEQ ID NO 134
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45
```

```
Ala Leu Ile Gly Gly Thr Asn Lys Arg Ala Pro Gly Val Pro Ser Arg
 50                  55                  60

Phe Ser Gly Ser Leu Ile Gly Asp Lys Ala Thr Leu Thr Ile Ser Ser
 65                  70                  75                  80

Leu Gln Pro Glu Asp Phe Ala Thr Tyr Tyr Cys Ala Leu Trp Tyr Ser
                 85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
            115                 120                 125

Lys Pro Gly Ala Ser Val Lys Val Ser Cys Lys Ala Ser Gly Tyr Thr
130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
            195                 200                 205

Val Tyr Tyr Cys Ala Arg Asp Arg Ala Val Thr Asp Tyr Tyr Tyr Gly
210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
            260                 265                 270

Ser Asn Thr Val Asn Trp Tyr Gln Gln Leu Pro Gly Thr Ala Pro Lys
            275                 280                 285

Leu Leu Ile Tyr Gly Asn Asn Gln Arg Pro Ser Gly Val Pro Asp Arg
290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
            340                 345                 350

Gly Gly Ser Gly Gly Ser Glu Val Gln Leu Val Glu Ser Gly Gly Gly
            355                 360                 365

Leu Val Gln Pro Gly Gly Ser Leu Arg Leu Ser Cys Ala Ala Ser Gly
370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
            435                 440                 445

Glu Asp Thr Ala Val Tyr Tyr Cys Ala Arg His Gly Asn Phe Gly Asn
450                 455                 460

Ser Tyr Val Ser Tyr Phe Ala Tyr Trp Gly Gln Gly Thr Leu Val Thr
```

Val Ser Ser

<210> SEQ ID NO 135
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 135

Asp Ile Gln Met Thr Gln Ser Pro Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
            35                  40                  45

Gly Leu Ile Gly Gly Thr Asn Lys Arg Ala Pro Gly Val Pro Ser Arg
        50                  55                  60

Phe Ser Gly Ser Leu Ile Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
        195                 200                 205

Val Tyr Tyr Cys Ala Arg Asp Arg Ala Val Thr Asp Tyr Tyr Gly
        210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
            260                 265                 270

Ser Asn Thr Val Asn Trp Tyr Gln Gln Leu Pro Gly Thr Ala Pro Lys
        275                 280                 285

Leu Leu Ile Tyr Gly Asn Asn Gln Arg Pro Ser Gly Val Pro Asp Arg
        290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
            340                 345                 350

```
Gly Gly Ser Gly Gly Ser Glu Val Gln Leu Val Glu Ser Gly Gly Gly
            355                 360                 365
Leu Val Gln Pro Gly Gly Ser Leu Arg Leu Ser Cys Ala Ala Ser Gly
    370                 375                 380
Phe Thr Phe Ser Thr Tyr Ala Met Asn Trp Val Arg Gln Ala Pro Gly
385                 390                 395                 400
Lys Gly Leu Glu Trp Val Gly Arg Ile Arg Ser Lys Tyr Asn Asn Tyr
                405                 410                 415
Ala Thr Tyr Tyr Ala Asp Ser Val Lys Asp Arg Phe Thr Ile Ser Arg
                420                 425                 430
Asp Asp Ser Lys Asn Ser Leu Tyr Leu Gln Met Asn Ser Leu Lys Thr
            435                 440                 445
Glu Asp Thr Ala Val Tyr Tyr Cys Ala Arg His Gly Asn Phe Gly Asn
            450                 455                 460
Ser Tyr Val Ser Trp Phe Ala Tyr Trp Gly Gln Gly Thr Leu Val Thr
465                 470                 475                 480
Val Ser Ser

<210> SEQ ID NO 136
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 136

Asp Ile Gln Met Thr Gln Ser Pro Ser Ser Leu Ser Ala Ser Val Gly
1               5                   10                  15
Asp Arg Val Thr Ile Thr Cys Arg Ser Ser Thr Gly Ala Val Thr Thr
            20                  25                  30
Ser Asn Tyr Ala Asn Trp Val Gln Gln Lys Pro Gly Lys Ala Pro Lys
        35                  40                  45
Ala Leu Ile Gly Gly Thr Asn Lys Arg Ala Pro Gly Val Pro Ser Arg
    50                  55                  60
Phe Ser Gly Ser Leu Ile Gly Asp Lys Ala Thr Leu Thr Ile Ser Ser
65                  70                  75                  80
Leu Gln Pro Glu Asp Phe Ala Thr Tyr Tyr Cys Ala Leu Trp Tyr Ser
                85                  90                  95
Asn Leu Trp Val Phe Gly Gln Gly Thr Lys Val Glu Ile Lys Gly Gly
                100                 105                 110
Ser Gly Gly Ser Gln Val Gln Leu Val Gln Ser Gly Ala Glu Val Lys
            115                 120                 125
Lys Pro Gly Ala Ser Val Lys Val Ser Cys Lys Ala Ser Gly Tyr Thr
    130                 135                 140
Phe Thr Ser Tyr Asp Ile Asn Trp Val Arg Gln Ala Pro Gly Gln Gly
145                 150                 155                 160
Leu Glu Trp Met Gly Trp Met Asn Pro Asn Ser Gly Asn Thr Gly Phe
                165                 170                 175
Ala Gln Lys Phe Gln Gly Arg Val Thr Met Thr Arg Asp Thr Ser Thr
                180                 185                 190
Ser Thr Val Tyr Met Glu Leu Ser Ser Leu Arg Ser Glu Asp Thr Ala
            195                 200                 205
Val Tyr Tyr Cys Ala Arg Asp Arg Ala Asn Thr Asp Phe Ser Tyr Gly
    210                 215                 220
```

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Arg Ser Asn Ile Gly
                260                 265                 270

Ser Asn Thr Val Asn Trp Tyr Gln Gln Leu Pro Gly Thr Ala Pro Lys
                275                 280                 285

Leu Leu Ile Tyr Gly Asn Asn Gln Arg Pro Ser Gly Val Pro Asp Arg
290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
                325                 330                 335

Ser Leu Ile Gly Trp Val Phe Gly Gly Gly Thr Lys Leu Thr Val Leu
                340                 345                 350

Gly Gly Ser Gly Gly Ser Glu Val Gln Leu Val Glu Ser Gly Gly Gly
                355                 360                 365

Leu Val Gln Pro Gly Gly Ser Leu Arg Leu Ser Cys Ala Ala Ser Gly
                370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
                420                 425                 430

Asp Asp Ser Lys Asn Ser Leu Tyr Leu Gln Met Asn Ser Leu Lys Thr
                435                 440                 445

Glu Asp Thr Ala Val Tyr Tyr Cys Ala Arg His Gly Asn Phe Gly Asn
                450                 455                 460

Ser Tyr Val Ser Tyr Phe Ala Tyr Trp Gly Gln Gly Thr Leu Val Thr
465                 470                 475                 480

Val Ser Ser

<210> SEQ ID NO 137
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
                20                  25                  30

Ser Asn Tyr Ala Asn Trp Val Gln Gln Lys Pro Gly Lys Ala Pro Lys
                35                  40                  45

Ala Leu Ile Gly Gly Thr Asn Lys Arg Ala Pro Gly Val Pro Ser Arg
50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly

Ser Gly Gly Ser Gln Val Gln Leu Val Gln Ser Gly Ala Glu Val Lys
            115                 120                 125

Lys Pro Gly Ala Ser Val Lys Val Ser Cys Lys Ala Ser Gly Tyr Thr
130                 135                 140

Phe Thr Ser Tyr Asp Ile Asn Trp Val Arg Gln Ala Pro Gly Gln Gly
145                 150                 155                 160

Leu Glu Trp Met Gly Trp Met Asn Pro Asn Ser Gly Asn Thr Gly Phe
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
            195                 200                 205

Val Tyr Tyr Cys Ala Arg Asp Arg Ala Asn Thr Asp Tyr Ser Phe Gly
210                 215                 220

Met Asp Val Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
            245                 250                 255

Gly Gln Arg Val Thr Ile Ser Cys Ser Gly Ser Arg Ser Asn Ile Gly
            260                 265                 270

Ser Asn Thr Val Asn Trp Tyr Gln Gln Leu Pro Gly Thr Ala Pro Lys
            275                 280                 285

Leu Leu Ile Tyr Gly Asn Asn Gln Arg Pro Ser Gly Val Pro Asp Arg
290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Thr Trp Asp Asp
            325                 330                 335

Ser Leu Ile Gly Trp Val Phe Gly Gly Gly Thr Lys Leu Thr Val Leu
            340                 345                 350

Gly Gly Ser Gly Gly Ser Glu Val Gln Leu Val Glu Ser Gly Gly Gly
            355                 360                 365

Leu Val Gln Pro Gly Gly Ser Leu Arg Leu Ser Cys Ala Ala Ser Gly
            370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
            435                 440                 445

Glu Asp Thr Ala Val Tyr Tyr Cys Ala Arg His Gly Asn Phe Gly Asn
450                 455                 460

Ser Tyr Val Ser Tyr Phe Ala Tyr Trp Gly Gln Gly Thr Leu Val Thr
465                 470                 475                 480

Val Ser Ser

<210> SEQ ID NO 138
<211> LENGTH: 483
<212> TYPE: PRT
<213> ORGANISM: Artificial Sequence
<220> FEATURE:

<223> OTHER INFORMATION: Synthetic polypeptide

<400> SEQUENCE: 138

Asp Ile Gln Met Thr Gln Ser Pro Ser Ser Leu Ser Ala Ser Val Gly
1               5                   10                  15
Asp Arg Val Thr Ile Thr Cys Arg Ser Ser Thr Gly Ala Val Thr Thr
            20                  25                  30
Ser Asn Tyr Ala Asn Trp Val Gln Gln Lys Pro Gly Lys Ala Pro Lys
        35                  40                  45
Ala Leu Ile Gly Gly Thr Asn Lys Arg Ala Pro Gly Val Pro Ser Arg
    50                  55                  60
Phe Ser Gly Ser Leu Ile Gly Asp Lys Ala Thr Leu Thr Ile Ser Ser
65                  70                  75                  80
Leu Gln Pro Glu Asp Phe Ala Thr Tyr Tyr Cys Ala Leu Trp Tyr Ser
                85                  90                  95
Asn Leu Trp Val Phe Gly Gln Gly Thr Lys Val Glu Ile Lys Gly Gly
            100                 105                 110
Ser Gly Gly Ser Gln Val Gln Leu Val Gln Ser Gly Ala Glu Val Lys
        115                 120                 125
Lys Pro Gly Ala Ser Val Lys Val Ser Cys Lys Ala Ser Gly Tyr Thr
130                 135                 140
Phe Thr Ser Tyr Asp Ile Asn Trp Val Arg Gln Ala Pro Gly Gln Gly
145                 150                 155                 160
Leu Glu Trp Met Gly Trp Met Asn Pro Asn Ser Gly Asn Thr Gly Phe
                165                 170                 175
Ala Gln Lys Phe Gln Gly Arg Val Thr Met Thr Arg Asp Thr Ser Thr
            180                 185                 190
Ser Thr Val Tyr Met Glu Leu Ser Ser Leu Arg Ser Glu Asp Thr Ala
        195                 200                 205
Val Tyr Tyr Cys Ala Arg Asp Arg Ala Asn Thr Asp Tyr Ser Leu Gly
    210                 215                 220
Met Asp Val Trp Gly Gln Gly Thr Leu Val Thr Val Ser Ser Gly Gly
225                 230                 235                 240
Ser Gly Gln Ser Val Leu Thr Gln Pro Pro Ser Ala Ser Gly Thr Pro
                245                 250                 255
Gly Gln Arg Val Thr Ile Ser Cys Ser Gly Ser Arg Ser Asn Ile Gly
            260                 265                 270
Ser Asn Thr Val Asn Trp Tyr Gln Gln Leu Pro Gly Thr Ala Pro Lys
        275                 280                 285
Leu Leu Ile Tyr Gly Asn Asn Gln Arg Pro Ser Gly Val Pro Asp Arg
    290                 295                 300
Phe Ser Gly Ser Lys Ser Gly Thr Ser Ala Ser Leu Ala Ile Ser Gly
305                 310                 315                 320
Leu Gln Ser Glu Asp Glu Ala Asp Tyr Tyr Cys Ala Thr Trp Asp Asp
                325                 330                 335
Ser Leu Ile Gly Trp Val Phe Gly Gly Gly Thr Lys Leu Thr Val Leu
            340                 345                 350
Gly Gly Ser Gly Gly Ser Glu Val Gln Leu Val Glu Ser Gly Gly Gly
        355                 360                 365
Leu Val Gln Pro Gly Gly Ser Leu Arg Leu Ser Cys Ala Ala Ser Gly
    370                 375                 380
Phe Thr Phe Ser Thr Tyr Ala Met Asn Trp Val Arg Gln Ala Pro Gly
385                 390                 395                 400

```
Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
            420                 425                 430

Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
    450                 455                 460

Ser Tyr Val Ser Tyr Phe Ala Tyr Trp Gly Gln Gly Thr Leu Val Thr
465                 470                 475                 480

Val Ser Ser

<210> SEQ ID NO 139
<211> LENGTH: 481
<212> TYPE: PRT
<213> ORGANISM: Artificial Sequence
<220> FEATURE:
<223> OTHER INFORMATION: Synthetic polypeptide

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Ala Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Glu Ser Leu Lys Ile Ser Cys Lys Gly Ser Gly Tyr Ser
    130                 135                 140

Phe Thr Ser Tyr Trp Ile Gly Trp Val Arg Gln Met Pro Gly Lys Gly
145                 150                 155                 160

Leu Glu Trp Met Gly Ile Ile Tyr Pro Gly Asp Ser Asp Thr Arg Tyr
                165                 170                 175

Ser Pro Ser Phe Gln Gly Gln Val Thr Ile Ser Ala Asp Lys Ser Ile
            180                 185                 190

Ser Thr Ala Tyr Leu Gln Trp Ser Ser Leu Lys Ala Ser Asp Thr Ala
        195                 200                 205

Met Tyr Tyr Cys Ala Arg His Lys Arg Gly Ser Asp Ala Phe Asp Ile
    210                 215                 220

Trp Gly Gln Gly Thr Thr Val Thr Val Ser Ser Gly Gly Ser Gly Gln
225                 230                 235                 240

Ser Val Leu Thr Gln Pro Pro Ser Val Ser Gly Ala Pro Gly Gln Arg
                245                 250                 255

Val Thr Ile Ser Cys Thr Gly Ser Ser Ser Asn Ile Gly Ala Gly Tyr
            260                 265                 270

Asp Val His Trp Tyr Gln Gln Leu Pro Gly Thr Ala Pro Lys Leu Leu
```

```
            275                 280                 285
Ile Tyr Gly Asn Ser Asn Arg Pro Ser Gly Val Pro Asp Arg Phe Ser
290                 295                 300

Gly Ser Lys Ser Gly Thr Ser Ala Ser Leu Ala Ile Thr Gly Leu Gln
305                 310                 315                 320

Ala Glu Asp Glu Ala Asp Tyr Tyr Cys Gln Ser Tyr Asp Ser Ser Leu
                325                 330                 335

Ser Asp Val Val Phe Gly Gly Gly Thr Lys Leu Thr Val Leu Gly Gly
            340                 345                 350

Ser Gly Gly Ser Glu Val Gln Leu Val Glu Ser Gly Gly Gly Leu Val
            355                 360                 365

Gln Pro Gly Gly Ser Leu Arg Leu Ser Cys Ala Ala Ser Gly Phe Thr
370                 375                 380

Phe Ser Thr Tyr Ala Met Asn Trp Val Arg Gln Ala Pro Gly Lys Gly
385                 390                 395                 400

Leu Glu Trp Val Gly Arg Ile Arg Ser Lys Tyr Asn Asn Tyr Ala Thr
                405                 410                 415

Tyr Tyr Ala Asp Ser Val Lys Asp Arg Phe Thr Ile Ser Arg Asp Asp
            420                 425                 430

Ser Lys Asn Ser Leu Tyr Leu Gln Met Asn Ser Leu Lys Thr Glu Asp
            435                 440                 445

Thr Ala Val Tyr Tyr Cys Ala Arg His Gly Asn Phe Gly Asn Ser Tyr
450                 455                 460

Val Ser Tyr Phe Ala Tyr Trp Gly Gln Gly Thr Leu Val Thr Val Ser
465                 470                 475                 480

Ser

<210> SEQ ID NO 140
<211> LENGTH: 481
<212> TYPE: PRT
<213> ORGANISM: Artificial Sequence
<220> FEATURE:
<223> OTHER INFORMATION: Synthetic polypeptide

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Tyr Phe
            100                 105                 110

Ala Tyr Trp Gly Gln Gly Thr Leu Val Thr Val Ser Ser Gly Gly Ser
            115                 120                 125

Gly Gly Ser Gln Ser Val Leu Thr Gln Pro Pro Ser Val Ser Gly Ala
        130                 135                 140

Pro Gly Gln Arg Val Thr Ile Ser Cys Thr Gly Ser Ser Ser Asn Ile
145                 150                 155                 160
```

Gly Ala Gly Tyr Asp Val His Trp Tyr Gln Gln Leu Pro Gly Thr Ala
            165                 170                 175

Pro Lys Leu Leu Ile Tyr Gly Asn Ser Asn Arg Pro Ser Gly Val Pro
            180                 185                 190

Asp Arg Phe Ser Gly Ser Lys Ser Gly Thr Ser Ala Ser Leu Ala Ile
            195                 200                 205

Thr Gly Leu Gln Ala Glu Asp Glu Ala Asp Tyr Tyr Cys Gln Ser Tyr
210                 215                 220

Asp Ser Ser Leu Ser Asp Val Val Phe Gly Gly Gly Thr Lys Leu Thr
225                 230                 235                 240

Val Leu Gly Gly Ser Gly Gln Val Gln Leu Val Gln Ser Gly Ala Glu
            245                 250                 255

Val Lys Lys Pro Gly Glu Ser Leu Lys Ile Ser Cys Lys Gly Ser Gly
            260                 265                 270

Tyr Ser Phe Thr Ser Tyr Trp Ile Gly Trp Val Arg Gln Met Pro Gly
            275                 280                 285

Lys Gly Leu Glu Trp Met Gly Ile Ile Tyr Pro Gly Asp Ser Asp Thr
290                 295                 300

Arg Tyr Ser Pro Ser Phe Gln Gly Gln Val Thr Ile Ser Ala Asp Lys
305                 310                 315                 320

Ser Ile Ser Thr Ala Tyr Leu Gln Trp Ser Ser Leu Lys Ala Ser Asp
            325                 330                 335

Thr Ala Met Tyr Tyr Cys Ala Arg His Lys Arg Gly Ser Asp Ala Phe
            340                 345                 350

Asp Ile Trp Gly Gln Gly Thr Thr Val Thr Val Ser Ser Gly Gly Ser
            355                 360                 365

Gly Gly Ser Asp Ile Gln Met Thr Gln Ser Pro Ser Ser Leu Ser Ala
            370                 375                 380

Ser Val Gly Asp Arg Val Thr Ile Thr Cys Arg Ser Ser Thr Gly Ala
385                 390                 395                 400

Val Thr Thr Ser Asn Tyr Ala Asn Trp Val Gln Gln Lys Pro Gly Lys
            405                 410                 415

Ala Pro Lys Ala Leu Ile Gly Gly Thr Asn Lys Arg Ala Pro Gly Val
            420                 425                 430

Pro Ser Arg Phe Ser Gly Ser Leu Ile Gly Asp Lys Ala Thr Leu Thr
            435                 440                 445

Ile Ser Ser Leu Gln Pro Glu Asp Phe Ala Thr Tyr Tyr Cys Ala Leu
            450                 455                 460

Trp Tyr Ser Asn Leu Trp Val Phe Gly Gln Gly Thr Lys Val Glu Ile
465                 470                 475                 480

Lys

<210> SEQ ID NO 141
<211> LENGTH: 484
<212> TYPE: PRT
<213> ORGANISM: Artificial Sequence
<220> FEATURE:
<223> OTHER INFORMATION: Synthetic polypeptide

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
            35                  40                  45

Ala Leu Ile Gly Gly Thr Asn Lys Arg Ala Pro Gly Val Pro Ser Arg
 50                  55                  60

Phe Ser Gly Ser Leu Ile Gly Asp Lys Ala Thr Leu Thr Ile Ser Ser
 65                  70                  75                  80

Leu Gln Pro Glu Asp Phe Ala Thr Tyr Tyr Cys Ala Leu Trp Tyr Ser
                 85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
            115                 120                 125

Lys Pro Gly Ala Ser Val Lys Val Ser Cys Lys Ala Ser Gly Tyr Thr
130                 135                 140

Phe Thr Ser Tyr Tyr Met His Trp Val Arg Gln Ala Pro Gly Gln Gly
145                 150                 155                 160

Leu Glu Trp Met Gly Ile Ile Asn Pro Ser Gly Gly Ser Thr Ser Tyr
                165                 170                 175

Ala Gln Lys Phe Gln Gly Arg Val Thr Met Thr Arg Asp Thr Ser Thr
            180                 185                 190

Ser Thr Val Tyr Met Glu Leu Ser Ser Leu Arg Ser Glu Asp Thr Ala
            195                 200                 205

Val Tyr Tyr Cys Ala Arg Asp Val Val Pro Ala Ala Ile Asp Tyr Tyr
            210                 215                 220

Gly Met Asp Val Trp Gly Gln Gly Thr Thr Val Thr Val Ser Ser Gly
225                 230                 235                 240

Gly Ser Gly Gln Ser Val Leu Thr Gln Pro Pro Ser Ala Ser Gly Thr
                245                 250                 255

Pro Gly Gln Arg Val Thr Ile Ser Cys Ser Gly Ser Ser Ser Asn Ile
            260                 265                 270

Gly Ser Asn Thr Val Asn Trp Tyr Gln Gln Leu Pro Gly Thr Ala Pro
            275                 280                 285

Lys Leu Leu Ile Tyr Ser Asp Asn Gln Arg Pro Ser Gly Val Pro Asp
290                 295                 300

Arg Phe Ser Gly Ser Lys Ser Gly Ser Ser Ala Ser Leu Ala Ile Ser
305                 310                 315                 320

Gly Leu Gln Ser Asp Asp Glu Ala Asp Tyr Tyr Cys Ala Thr Trp Asp
                325                 330                 335

Asp Ser Leu Asn Gly Ala Val Phe Gly Gly Gly Thr Lys Leu Thr Val
            340                 345                 350

Leu Gly Gly Ser Gly Gly Ser Glu Val Gln Leu Val Glu Ser Gly Gly
            355                 360                 365

Gly Leu Val Gln Pro Gly Gly Ser Leu Arg Leu Ser Cys Ala Ala Ser
            370                 375                 380

Gly Phe Thr Phe Ser Thr Tyr Ala Met Asn Trp Val Arg Gln Ala Pro
385                 390                 395                 400

Gly Lys Gly Leu Glu Trp Val Gly Arg Ile Arg Ser Lys Tyr Asn Asn
                405                 410                 415

Tyr Ala Thr Tyr Tyr Ala Asp Ser Val Lys Asp Arg Phe Thr Ile Ser
            420                 425                 430

Arg Asp Asp Ser Lys Asn Ser Leu Tyr Leu Gln Met Asn Ser Leu Lys
            435                 440                 445

Thr Glu Asp Thr Ala Val Tyr Tyr Cys Ala Arg His Gly Asn Phe Gly

```
                  450                 455                 460

Asn Ser Tyr Val Ser Tyr Phe Ala Tyr Trp Gly Gln Gly Thr Leu Val
465                 470                 475                 480

Thr Val Ser Ser

<210> SEQ ID NO 142
<211> LENGTH: 484
<212> TYPE: PRT
<213> ORGANISM: Artificial Sequence
<220> FEATURE:
<223> OTHER INFORMATION: Synthetic polypeptide

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ser Arg
    50                  55                  60

Phe Ser Gly Ser Leu Ile Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
            85                  90                  95

Asn Leu Trp Val Phe Gly Gln Gly Thr Lys Val Glu Ile Lys Gly Gly
        100                 105                 110

Ser Gly Gly Ser Gln Val Gln Leu Val Gln Ser Gly Ala Glu Val Lys
    115                 120                 125

Lys Pro Gly Ala Ser Val Lys Val Ser Cys Lys Ala Ser Gly Tyr Thr
130                 135                 140

Phe Thr Ser Tyr Tyr Met His Trp Val Arg Gln Ala Pro Gly Gln Gly
145                 150                 155                 160

Leu Glu Trp Met Gly Ile Ile Asn Pro Ser Gly Gly Ser Thr Ser Tyr
            165                 170                 175

Ala Gln Lys Phe Gln Gly Arg Val Thr Met Thr Arg Asp Thr Ser Thr
        180                 185                 190

Ser Thr Val Tyr Met Glu Leu Ser Ser Leu Arg Ser Glu Asp Thr Ala
    195                 200                 205

Val Tyr Tyr Cys Ala Arg Asp Val Val Pro Ala Ala Ile Asp Tyr Tyr
210                 215                 220

Gly Met Asp Val Trp Gly Gln Gly Thr Thr Val Thr Val Ser Ser Gly
225                 230                 235                 240

Gly Ser Gly Gln Ser Val Leu Thr Gln Pro Pro Ser Ala Ser Gly Thr
            245                 250                 255

Pro Gly Gln Arg Val Thr Ile Ser Cys Ser Gly Ser Ser Ser Asn Ile
        260                 265                 270

Gly Ser Asn Thr Val Asn Trp Tyr Gln Gln Leu Pro Gly Thr Ala Pro
    275                 280                 285

Lys Leu Leu Ile Tyr Ser Asp Asn Gln Arg Pro Ser Gly Val Pro Asp
290                 295                 300

Arg Phe Ser Gly Ser Lys Ser Gly Ser Ser Ala Ser Leu Ala Ile Ser
305                 310                 315                 320

Gly Leu Gln Ser Asp Asp Glu Ala Asp Tyr Tyr Cys Ala Thr Trp Asp
            325                 330                 335
```

-continued

Asp Ser Leu Asn Gly Ala Val Phe Gly Gly Thr Lys Leu Thr Val
                340                 345                 350

Leu Gly Gly Ser Gly Gly Ser Glu Val Gln Leu Val Glu Ser Gly Gly
            355                 360                 365

Gly Leu Val Gln Pro Gly Gly Ser Leu Arg Leu Ser Cys Ala Ala Ser
370                 375                 380

Gly Phe Thr Phe Ser Thr Tyr Ala Met Asn Trp Val Arg Gln Ala Pro
385                 390                 395                 400

Gly Lys Gly Leu Glu Trp Val Gly Arg Ile Arg Ser Lys Tyr Asn Asn
                405                 410                 415

Tyr Ala Thr Tyr Tyr Ala Asp Ser Val Lys Asp Arg Phe Thr Ile Ser
                420                 425                 430

Arg Asp Asp Ser Lys Asn Ser Leu Tyr Leu Gln Met Asn Ser Leu Lys
                435                 440                 445

Thr Glu Asp Thr Ala Val Tyr Tyr Cys Ala Arg His Gly Asn Phe Gly
                450                 455                 460

Asn Ser Tyr Val Ser Trp Phe Ala Tyr Trp Gly Gln Gly Thr Leu Val
465                 470                 475                 480

Thr Val Ser Ser

<210> SEQ ID NO 143
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
                20                  25                  30

Ser Asn Tyr Ala Asn Trp Val Gln Gln Lys Pro Gly Lys Ala Pro Lys
            35                  40                  45

Ala Leu Ile Gly Gly Thr Asn Lys Arg Ala Pro Gly Val Pro Ser Arg
        50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
                100                 105                 110

Ser Gly Gly Ser Gln Val Gln Leu Val Gln Ser Gly Ala Glu Val Lys
            115                 120                 125

Lys Pro Gly Ser Ser Val Lys Val Ser Cys Lys Ala Ser Gly Gly Thr
        130                 135                 140

Phe Ser Ser Tyr Ala Ile Ser Trp Val Arg Gln Ala Pro Gly Gln Gly
145                 150                 155                 160

Leu Glu Trp Met Gly Gly Ile Tyr Pro Ile Phe Gly Ser Ala Asn Tyr
                165                 170                 175

Ala Gln Lys Phe Gln Gly Arg Val Thr Ile Thr Ala Asp Glu Ser Thr
                180                 185                 190

Ser Thr Ala Tyr Met Glu Leu Ser Ser Leu Arg Ser Glu Asp Thr Ala
            195                 200                 205

```
Val Tyr Tyr Cys Ala Arg Glu Tyr Tyr Tyr Asp Ser Ser Glu Trp Ala
    210                 215                 220

Phe Asp Ile Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Ser Ser Asn Ile Gly
                260                 265                 270

Ser Asn Ile Val Asn Trp Tyr Gln Gln Leu Pro Gly Thr Ala Pro Lys
            275                 280                 285

Leu Leu Ile Tyr Ser Asn Asn Gln Arg Pro Ser Gly Val Pro Asp Arg
290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Ala Trp Asp Asp
                325                 330                 335

Ser Leu Lys Gly Tyr Val Phe Gly Gly Gly Thr Lys Leu Thr Val Leu
                340                 345                 350

Gly Gly Ser Gly Gly Ser Glu Val Gln Leu Val Glu Ser Gly Gly Gly
            355                 360                 365

Leu Val Gln Pro Gly Gly Ser Leu Arg Leu Ser Cys Ala Ala Ser Gly
370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
                420                 425                 430

Asp Asp Ser Lys Asn Ser Leu Tyr Leu Gln Met Asn Ser Leu Lys Thr
            435                 440                 445

Glu Asp Thr Ala Val Tyr Tyr Cys Ala Arg His Gly Asn Phe Gly Asn
        450                 455                 460

Ser Tyr Val Ser Tyr Phe Ala Tyr Trp Gly Gln Gly Thr Leu Val Thr
465                 470                 475                 480

Val Ser Ser

<210> SEQ ID NO 144
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Arg Ser Ser Gly Ala Val Thr Thr
                20                  25                  30

Ser Asn Tyr Ala Asn Trp Val Gln Gln Lys Pro Gly Lys Ala Pro Lys
            35                  40                  45

Ala Leu Ile Gly Gly Thr Asn Lys Arg Ala Pro Gly Val Pro Ser Arg
        50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
```

85                  90                  95
Asn Leu Trp Val Phe Gly Gln Gly Thr Lys Val Glu Ile Lys Gly Gly
                100                 105                 110

Ser Gly Gly Ser Gln Val Gln Leu Val Gln Ser Gly Ala Glu Val Lys
                115                 120                 125

Lys Pro Gly Ser Ser Val Lys Val Ser Cys Lys Ala Ser Gly Gly Thr
130                 135                 140

Phe Ser Ser Tyr Gly Ile Ser Trp Val Arg Gln Ala Pro Gly Gln Gly
145                 150                 155                 160

Leu Glu Trp Met Gly Gly Ile Ile Pro Ile Phe Gly Ser Ala His Tyr
                165                 170                 175

Ala Gln Lys Phe Gln Gly Arg Val Thr Ile Thr Ala Asp Glu Ser Thr
                180                 185                 190

Ser Thr Ala Tyr Met Glu Leu Ser Ser Leu Arg Ser Glu Asp Thr Ala
                195                 200                 205

Val Tyr Tyr Cys Ala Arg Glu Tyr Tyr Asp Ser Ser Glu Trp Ala
                210                 215                 220

Phe Asp Ile Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Ser Asn Ile Gly
                260                 265                 270

Ser Asn Thr Val Lys Trp Tyr Gln Gln Leu Pro Gly Thr Ala Pro Lys
                275                 280                 285

Leu Leu Ile Tyr Ser Asn Asn Gln Arg Ser Ser Gly Val Pro Asp Arg
                290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Ala Trp Asp Asp
                325                 330                 335

Ser Leu Asn Gly Tyr Val Phe Gly Gly Gly Thr Lys Leu Thr Val Leu
                340                 345                 350

Gly Gly Ser Gly Gly Ser Glu Val Gln Leu Val Glu Ser Gly Gly Gly
                355                 360                 365

Leu Val Gln Pro Gly Gly Ser Leu Arg Leu Ser Cys Ala Ala Ser Gly
                370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
                420                 425                 430

Asp Asp Ser Lys Asn Ser Leu Tyr Leu Gln Met Asn Ser Leu Lys Thr
                435                 440                 445

Glu Asp Thr Ala Val Tyr Tyr Cys Ala Arg His Gly Asn Phe Gly Asn
                450                 455                 460

Ser Tyr Val Ser Tyr Phe Ala Tyr Trp Gly Gln Gly Thr Leu Val Thr
465                 470                 475                 480

Val Ser Ser

<210> SEQ ID NO 145
<211> LENGTH: 483

```
<212> TYPE: PRT
<213> ORGANISM: Artificial Sequence
<220> FEATURE:
<223> OTHER INFORMATION: Synthetic polypeptide

<400> SEQUENCE: 145

Asp Ile Gln Met Thr Gln Ser Pro Ser Ser Leu Ser Ala Ser Val Gly
 1               5                  10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Gly Leu Ile Gly Gly Thr Asn Lys Arg Ala Pro Gly Val Pro Ser Arg
    50                  55                  60

Phe Ser Gly Ser Leu Ile Gly Thr Asp Phe Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ser Ser Val Lys Val Ser Cys Lys Ala Ser Gly Gly Thr
    130                 135                 140

Phe Ser Ser Tyr Gly Ile Ser Trp Val Arg Gln Ala Pro Gly Gln Gly
145                 150                 155                 160

Leu Glu Trp Met Gly Gly Ile Ile Pro Ile Phe Gly Ser Ala His Tyr
                165                 170                 175

Ala Gln Lys Phe Gln Gly Arg Val Thr Ile Thr Ala Asp Glu Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Arg Glu Tyr Tyr Tyr Asp Ser Ser Glu Trp Ala
    210                 215                 220

Phe Asp Ile Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Ser Ser Asn Ile Gly
            260                 265                 270

Ser Asn Thr Val Lys Trp Tyr Gln Gln Leu Pro Gly Thr Ala Pro Lys
        275                 280                 285

Leu Leu Ile Tyr Ser Asn Asn Gln Arg Ser Ser Gly Val Pro Asp Arg
    290                 295                 300

Phe Ser Gly Ser Lys Ser Gly Thr Ser Ala Ser Leu Ala Ile Ser Gly
305                 310                 315                 320

Leu Gln Ser Glu Asp Glu Ala Asp Tyr Tyr Cys Ala Ala Trp Asp Asp
                325                 330                 335

Ser Leu Asn Gly Tyr Val Phe Gly Gly Gly Thr Lys Leu Thr Val Leu
            340                 345                 350

Gly Gly Ser Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380
```

```
Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
            405                 410                 415

Ala Thr Tyr Tyr Ala Asp Ser Val Lys Asp Arg Phe Thr Ile Ser Arg
        420                 425                 430

Asp Asp Ser Lys Asn Ser Leu Tyr Leu Gln Met Asn Ser Leu Lys Thr
        435                 440                 445

Glu Asp Thr Ala Val Tyr Tyr Cys Ala Arg His Gly Asn Phe Gly Asn
    450                 455                 460

Ser Tyr Val Ser Trp Phe Ala Tyr Trp Gly Gln Gly Thr Leu Val Thr
465                 470                 475                 480

Val Ser Ser

<210> SEQ ID NO 146
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Ala Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys Gly Gly
            100                 105                 110

Ser Gly Gly Ser Gln Val Gln Leu Val Gln Ser Gly Ala Glu Val Lys
        115                 120                 125

Lys Pro Gly Ser Ser Val Lys Val Ser Cys Lys Ala Ser Gly Gly Thr
    130                 135                 140

Phe Asp Ser Tyr Ala Ile Ser Trp Val Arg Gln Ala Pro Gly Gln Gly
145                 150                 155                 160

Leu Glu Trp Met Gly Gly Ile Ile Pro Ile Phe Gly Ser Ala His Tyr
                165                 170                 175

Ser Gln Lys Phe Gln Gly Arg Val Thr Ile Thr Ala Asp Glu Ser Thr
            180                 185                 190

Ser Thr Ala Tyr Met Glu Leu Ser Leu Arg Ser Glu Asp Thr Ala
        195                 200                 205

Val Tyr Tyr Cys Ala Arg Glu Tyr Tyr Asp Ser Ser Glu Trp Ala
    210                 215                 220

Phe Asp Ile Trp Gly Gln Gly Thr Leu Val Thr Val Ser Ser Gly Gly
225                 230                 235                 240

Ser Gly Gln Ser Val Leu Thr Gln Pro Pro Ser Ala Ser Gly Thr Pro
                245                 250                 255

Gly Gln Arg Val Thr Ile Ser Cys Ser Gly Ser Ser Ser Asn Ile Gly
```

```
            260                 265                 270
Asp Asn Val Val Asn Trp Tyr Gln Gln Leu Pro Gly Thr Ala Pro Lys
            275                 280                 285

Leu Leu Ile Tyr Ser Thr Asn Lys Arg Pro Ser Gly Val Pro Asp Arg
            290                 295                 300

Phe Ser Gly Ser Lys Ser Gly Ser Ser Ala Ser Leu Ala Ile Ser Gly
305                 310                 315                 320

Leu Gln Ser Glu Asp Glu Ala Asp Tyr Tyr Cys Ala Ala Trp Asp Asp
                325                 330                 335

Ser Leu Ser Ala Tyr Val Phe Gly Gly Gly Thr Lys Leu Thr Val Leu
            340                 345                 350

Gly Gly Ser Gly Gly Ser Glu Val Gln Leu Val Glu Ser Gly Gly Gly
            355                 360                 365

Leu Val Gln Pro Gly Gly Ser Leu Arg Leu Ser Cys Ala Ala Ser Gly
        370                 375                 380

Phe Thr Phe Ser Thr Tyr Ala Met Asn Trp Val Arg Gln Ala Pro Gly
385                 390                 395                 400

Lys Gly Leu Glu Trp Val Gly Arg Ile Arg Ser Lys Tyr Asn Asn Tyr
                405                 410                 415

Ala Thr Tyr Tyr Ala Asp Ser Val Lys Asp Arg Phe Thr Ile Ser Arg
                420                 425                 430

Asp Asp Ser Lys Asn Ser Leu Tyr Leu Gln Met Asn Ser Leu Lys Thr
            435                 440                 445

Glu Asp Thr Ala Val Tyr Tyr Cys Ala Arg His Gly Asn Phe Gly Asn
        450                 455                 460

Ser Tyr Val Ser Tyr Phe Ala Tyr Trp Gly Gln Gly Thr Leu Val Thr
465                 470                 475                 480

Val Ser Ser
```